(12) United States Patent
Frost et al.

(10) Patent No.: US 11,738,093 B2
(45) Date of Patent: Aug. 29, 2023

(54) AAV-MEDIATED DELIVERY OF ATP1A3 GENES TO CENTRAL NERVOUS SYSTEM

(71) Applicants: Cure AHC, Inc., Raleigh, NC (US); Hope for Annabel, Washington, DC (US); Alternating Hemiplegia of Childhood Foundation, Southfield, MI (US)

(72) Inventors: Simon Frost, Washington, DC (US); Natalia Morsci, Salt Lake City, UT (US); Neil Hackett, Santa Monica, CA (US); Dolan Sondhi, New York, NY (US)

(73) Assignees: Hope for Annabel, Washington, DC (US); Cure AHC, Inc., Raleigh, NC (US); Alternating Hemiplegia of Childhood Foundation, Southfield, MI (US)

( * ) Notice: Subject to any disclaimer, the term of this patent is extended or adjusted under 35 U.S.C. 154(b) by 607 days.

(21) Appl. No.: 16/379,440

(22) Filed: Apr. 9, 2019

(65) Prior Publication Data
US 2019/0358346 A1    Nov. 28, 2019

Related U.S. Application Data

(60) Provisional application No. 62/654,645, filed on Apr. 9, 2018.

(51) Int. Cl.
*A61K 48/00* (2006.01)

(52) U.S. Cl.
CPC ........ *A61K 48/005* (2013.01); *A61K 48/0075* (2013.01)

(58) Field of Classification Search
CPC .............. A61K 48/005; A61K 48/0075; C07K 14/705; C12N 9/00; C12N 2750/14143; C12N 15/86; A01K 2217/072; A01K 2217/075; A01K 2227/105; A01K 2267/0306; A61P 25/00
See application file for complete search history.

(56) References Cited

U.S. PATENT DOCUMENTS

| | | |
|---|---|---|
| 2012/0308484 A1 | 12/2012 | Szalay et al. |
| 2015/0010578 A1 | 1/2015 | Balazs et al. |
| 2018/0071373 A1 | 3/2018 | Mcivor et al. |

OTHER PUBLICATIONS

Ruegsegger et al. "Aberrant association of misfolded SOD1 with Na+/K+ ATPase-α3 impairs its activity and contributes to motor neuron vulnerability in ALS." Acta neuropathologica 131.3 (2016): 427-451 (Year: 2016).*
Nathanson et al. "Short promoters in viral vectors drive selective expression in mammalian inhibitory neurons, but do not restrict activity to specific inhibitory cell-types." Frontiers in neural circuits 3 (2009): 19 (Year: 2009).*
Guhasarkar et al. "A Walk on the Fine Line Between Reward and Risk: AAV-IFNβ Gene Therapy for Glioblastoma: A Dissertation." (2016) (Year: 2016).*
Gray et al. "Design and construction of functional AAV vectors." Adeno-Associated Virus. Humana Press, 2012. 25-46 (Year: 2012).*
Clapcote, et al., "Mutation I810N in the alpha3 isoform of Na+, K+-ATPase causes impairments in the sodium pump and hyperexcitability in the CNS", Proc Natl Acad Sci USA, Aug. 3, 2009, vol. 106, pp. 14085-14090, entire document.
Henriksen, et al., "Molecular cloning and characterization of porcine Na+/K+-ATPase isoforms a1, a2, a3 and the ATP1A3 promoter", PLoS One, Nov. 13, 2013, vol. 8, e79127, pp. 1-15, entire document.
Kirshenbaum, et al., "Transgenic rescue of phenotypic deficits in a mouse model of alternating hemiplegia of childhood", Neurogenetics, Oct. 13, 2015, vol. 17, pp. 57-63, entire document.

* cited by examiner

*Primary Examiner* — Janet L Epps-Smith
*Assistant Examiner* — Alexander W Nicol
(74) *Attorney, Agent, or Firm* — Jeffrey N. Townes; Cozen O'Connor

(57) ABSTRACT

This invention relates to a transgenic vector for transducing cells of a mammal's CNS and transgenically expressing a protein in the mammal's CNS. The transgenic vector comprises a virus-derived vector, a nucleic acid sequence encoding the protein, and an endogenous ATP1A3 promoter sequence. This invention also relates to a composition comprising a recombinant AAV vector comprising a nucleic acid sequence encoding a ATP1A3 protein, in a form compatible with administration into the CNS. The invention also relates to a method for treating a subject having a neurological disorder associated with mutations in the ATP1A3 gene and a method for delivering a transgenic ATP1A3 DNA to the central nervous system of a mammal by administering the recombinant AAV vector into the mammal's CNS.

13 Claims, 27 Drawing Sheets
Specification includes a Sequence Listing.

SEQUENCE LISTING

<160> NUMBER OF SEQ ID NOS: 7

<210> SEQ ID NO 1
<211> LENGTH: 549
<212> TYPE: DNA
<213> ORGANISM: Mus sp.

<400> SEQUENCE: 1

```
acatactgca agatggtggc actctggggc cctgcattac tgcaattcac tgggcctttc    60
ctcccaccct gtatctaccc cactcccaga aggaggcaga ttccagggtg cctcaccctc   120
aaagcctcgg tccctaagat acctccctat attgaggggg ggtctctgag tccccaccct   180
ggggatgtcc gggatcaccc cccccccccg cactgtgctc agcttctcag tggccgccac   240
tttgcagaaa caaggttgga gcggtgaggg ggggaagggg gagtacagct gcagtactgg   300
gggccgggcc gcaagctgtc cgtctgctca gtactgctcc tgattggccg gagccgcctc   360
ccccgcggg cgcgggcata tgaggaggcg gaggccccgg ccgccgcagc ctctgtgcgg   420
tgggacccac ggaccgacag acgcacgctc ccaccgcggc gcgggcgctg cagaggcccc   480
cagcccgagc ccgcgcctga gcccatcctg cggccaccgc tcatcagtct gaacccgctc   540
ttcccgcgg                                                          549
```

<210> SEQ ID NO 2
<211> LENGTH: 1772
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgca cgcgtacata ctgcaagatg gtggcactct   180
ggggcccctgc attactgcaa ttcactgggc ctttcctccc acctgtatc taccccactc   240
ccagaaggag gcagattcca gggtgcctca ccctcaaagc ctcggtccct aagataccctc   300
cctatattga ggggggtct ctgagtccc accctgggga tgtccgggat caccccccccc   360
ccccgcactg tgctcagctt ctcagtggcc gccactttgc agaaacaagg ttggagcggt   420
gaggggggga agggggagta cagctgcagt actgggggcc gggccgcaag ctgtccgtct   480
gctcagtact gctcctgatt ggccggagcc gcctcccccc gcgggcgcgg gcatatgagg   540
```

| | |
|---|---:|
| aggcggaggc cccggccgcc gcagcctctg tgcggtggga cccacggacc gacagacgca | 600 |
| cgctcccacc gcggcgcggg cgctgcagag gcccccagcc cgagcccgcg cctgagccca | 660 |
| tcctgcggcc accgctcatc agtctgaacg ccgctcttcc cgcggaccgg tgccaccatg | 720 |
| gtgagcaagg gcgaggagga taacatggcc atcatcaagg agttcatgcg cttcaaggtg | 780 |
| cacatggagg gctccgtgaa cggccacgag ttcgagatcg agggcgaggg cgagggccgc | 840 |
| ccctacgagg gcacccagac cgccaagctg aaggtgacca aggtggcccc ctgcccttc | 900 |
| gcctgggaca tcctgtcccc tcagttcatg tacggctcca aggcctacgt gaagcacccc | 960 |
| gccgacatcc ccgactactt gaagctgtcc ttccccgagg gcttcaagtg ggagcgcgtg | 1020 |
| atgaacttcg aggacggcgg cgtggtgacc gtgacccagg actcctccct gcaggacggc | 1080 |
| gagttcatct acaaggtgaa gctgcgcggc accaacttcc cctccgacgg ccccgtaatg | 1140 |
| cagaagaaga ccatgggctg ggaggcctcc tccgagcgga tgtaccccga ggacggcgcc | 1200 |
| ctgaagggcg agatcaagca gaggctgaag ctgaaggacg gcggccacta cgacgctgag | 1260 |
| gtcaagacca cctacaaggc caagaagccc gtgcagctgc ccggcgccta caacgtcaac | 1320 |
| atcaagttgg acatcacctc ccacaacgag gactacacca tcgtggaaca gtacgaacgc | 1380 |
| gccgagggcc gccactccac cggcggcatg gacgagctgt acaagtaagt cgacccgggc | 1440 |
| ggcctcgagg acggggtgaa ctacgcctga ggatccgatc ttttccctc tgccaaaaat | 1500 |
| tatgggggaca tcatgaagcc ccttgagcat ctgacttctg gctaataaag gaaatttatt | 1560 |
| ttcattgcaa tagtgtgttg gaattttttg tgtctctcac tcgtccggac acgtgcggac | 1620 |
| cgagcggccg caggaaccccc tagtgatgga gttggccact ccctctctgc gcgctcgctc | 1680 |
| gctcactgag gccgggcgac caaaggtcgc ccgacgcccg gcttttgccc gggcggcctc | 1740 |
| agtgagcgag cgagcgcgca gctgcctgca gg | 1772 |

<210> SEQ ID NO 3
<211> LENGTH: 3729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---:|
| acatactgca agatggtggc actctggggc cctgcattac tgcaattcac tgggcctttc | 60 |
| ctcccaccct gtatctaccc cactcccaga aggaggcaga ttccagggtg cctcaccctc | 120 |
| aaagcctcgg tccctaagat acctcccttat attgagggggg ggtctctgag tccccaccct | 180 |
| ggggatgtcc gggatcaccc ccccccccg cactgtgctc agcttctcag tggccgccac | 240 |
| tttgcagaaa caaggttgga gcggtgaggg ggggaagggg gagtacagct gcagtactgg | 300 |
| gggccgggcc gcaagctgtc cgtctgctca gtactgctcc tgattggccg gagccgcctc | 360 |
| cccccgcggg cgcgggcata tgaggaggcg gaggcccccgg ccgccgcagc ctctgtgcgg | 420 |
| tgggacccac ggaccgacag acgcacgctc ccaccgcggc gcgggcgctg cagaggcccc | 480 |
| cagcccgagc ccgcgcctga gcccatcctg cggccaccgc tcatcagtct gaacgccgct | 540 |
| cttcccgcgg gccaccatgg gggacaaaaa agatgacaag agctcgccca agaagagcaa | 600 |
| ggccaaagag cgccgggacc tggatgacct caagaaggaa gtggctatga cagagcacaa | 660 |
| gatgtcagta gaagaggtct gccggaaata caatactgac tgcgtgcagg gtctgacaca | 720 |
| cagtaaagcc caggagatcc tagcccggga tgggcctaac gccctcacac caccgcccac | 780 |

```
caccccagaa tgggtcaagt tctgccggca gctgtttggt ggcttctcta tcctgctgtg    840
gatcggggca atccttttgct tcctggccta tggcatccag gcagggacgg aggatgaccc    900
ttccggtgac aatctgtacc tgggcatagt gctggccgca gtcgtgatca tcaccggctg    960
cttctcctac taccaagaag ccaagagttc taagatcatg gagtccttca gaacatggt    1020 cccccagcaa gcccttgtga tccgggaagg tgaaaagatg caggtgaatg cggaggaggt    1080
ggtggtcggg gacctggtgg agatcaaggg tggtgaccgg gtgccagctg acctgcgcat    1140
catctcggcc catggctgca aggtggacaa ctcctccctg actggcgaat ctgagcctca    1200
gacccgctcc ccggactgca cacgcacaa ccccctggag actcggaaca tcaccttctt    1260
ttccaccaac tgcgtggaag gcaccgctcg gggtgtggtg gtagccacag gtgaccgcac    1320
cgtcatgggc cgcattgcca ccctggcctc gggcttggag gtgggcaaga cgcccatcgc    1380
cattgagatt gagcatttca tccagctcat tacgggcgtg gccgtgttcc tgggcgtgtc    1440
cttcttcatc ctctctctca ttctgggtta cacctggctc gaggcagtca tcttcctcat    1500
cggcatcatt gtggccaatg tcccagaggg gctgctggct actgtcacgg tgtgtctgac    1560
gctgaccgcc aagcgcatgg ctcgcaagaa ctgcctggtg aagaacctgg aggcggtgga    1620
gacgctgggc tccacgtcca ccatctgctc ggacaagacc ggcactctca cccagaaccg    1680
catgaccgtc gcccacatgt ggtttgacaa ccagatccac gaggcagaca ccacagagga    1740
tcagtcaggg acctctttcg acaagagctc acacacctgg gtggccctgt cccacatcgc    1800
cgggctctgc aaccgggccg tcttcaaggg cgggcaggac aacatcccag tactcaagag    1860
ggacgtggcc ggtgatgcct ccgagtctgc cctgcttaag tgcattgagc tgtcctcggg    1920
ttccgtaaag ctgatgcgag aacggaacaa gaaagtggct gagattccgt tcaactcgac    1980
caacaaatac cagctatcca tccatggaag tgaggatccc aatgacaacc ggtacctgct    2040
agtgatgaag ggcgccccg aacgcattct ggaccgctgt gccaccatcc tcctgcaggg    2100
caaggagcag cctctggatg aggagatgaa ggaggcctcc cagaatgcct acctggagct    2160
tggtggcctg ggcgagcgtg tgctgggttt ctgccattac tacctgcctg aggaacagtt    2220
ccccaagggc tttgccttttg actgtgatga cgtgaacttc accacagaca accttttgctt    2280 tgtgggtctc atgtccatga ttgaccctcc ccgggcagcc gtccctgacg ctgtgggcaa    2340
atgccgaagc gcaggcatca aggtcatcat ggtcaccggc gatcacccca tcactgccaa    2400
ggccattgcc aagggtgtgg gtatcatctc tgagggtaac gagactgtcg aagacatcgc    2460
tgcccggctc aacatccctg tcagccaggt gaacccagg gatgccaaag cctgtgtgat    2520
tcacggcacc gacctcaagg acttcaccctc ggagcagatt gacgagattc tgcagaacca    2580
caccgagatc gtctttttgccc gaacctcccc tcagcagaag ctcatcatcg tggagggctg    2640
tcagagacag ggagcaattg tggctgtgac tggcgatggt gtgaatgact ccctgctct    2700 gaagaaggct gacatcgggg tggccatggg cattgctggc tctgatgtct ctaagcaggc    2760
tgccgacatg attctgctgg atgacaactt tgcttccatt gtcactggtg tggaggaagg    2820
ccgcctgatc tttgacaacc tgaagaaatc catcgcctac actctgacta gcaacatccc    2880
tgagatcaca cccttcctgc tcttcatcat ggctaacatc ccactgcctc ttggcaccat    2940
caccatcctc tgcattgacc tgggtaccga catggtccct gcaatctccc tggcctacga    3000
ggctgccgag agcgacatca tgaagaggca gcccaggaac ccacgcacag acaaactggt    3060
caacgaaagg ctcatcagca tggcctacgg gcagattggg atgatccagg ccctcggtgg    3120
tttcttctcc tactttgtca tcctggcaga aaatggcttc ttgcccggaa acctggtggg    3180
```

| | |
|---|---|
| catccggctc aactgggatg atcgcactgt caatgaccta gaagacagtt atgggcagca | 3240 |
| gtggacttat gagcagagga aggtggtaga gttcacatgc cacacagcct tctttgtgag | 3300 |
| tatcgtggtg gtccagtggg ctgacctgat catctgcaag accaggagga actccgtctt | 3360 |
| ccagcagggc atgaagaata agatcttgat cttcggcttg tttgaggaga cggccctcgc | 3420 |
| tgccttcctg tcctactgcc aggcatgga tgtggcccctt cgcatgtacc ctctcaagcc | 3480 |
| cagctggtgg ttctgtgcct tcccctacag tttcctcatc ttcgtctatg atgagattcg | 3540 |
| caaactcatc ctgcgcagga accccgggg ttgggtggag aaagagacct actattgaga | 3600 |
| tcttttttccc tctgccaaaa attatgggga catcatgaag ccccttgagc atctgacttc | 3660 |
| tggctaataa aggaaattta ttttcattgc aatagtgtgt tggaattttt tgtgtctctc | 3720 |
| actcggaag | 3729 |

<210> SEQ ID NO 4
<211> LENGTH: 3984
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---|
| cgttacataa cttacggtaa atggcccgcc tggctgaccg cccaacgacc cccgcccatt | 60 |
| gacgtcaata gtaacgccaa tagggacttt ccattgacgt caatgggtgg agtatttacg | 120 |
| gtaaactgcc cacttggcag tacatcaagt gtatcatatg ccaagtacgc ccccctattga | 180 |
| cgtcaatgac ggtaaatggc ccgcctggca ttgtgcccag tacatgacct tatgggactt | 240 |
| tcctacttgg cagtacatct acgtattagt catcgctatt accatggtcg aggtgagccc | 300 |
| cacgttctgc ttcactctcc ccatctcccc cccctcccca cccccaattt tgtatttatt | 360 |
| tattttttaa ttattttgtg cagcgatggg ggcggggggg gggggggggc gcgcgccagg | 420 |
| cggggcgggg cggggcgagg ggcggggcgg ggcgaggcgg agaggtgcgg cggcagccaa | 480 |
| tcagagcggc gcgctccgaa agtttccttt tatggcgagg cggcggcggc ggcggcccta | 540 |
| taaaaagcga agcgcgcggc gggcgggagt cgctgcgacg ctgccttcgc cccgtgcccc | 600 |
| gctccgccgc cgcctcgcgc cgcccgcccc ggctctgact gaccgcgtta ctcccacagg | 660 |
| tgagcgggcg ggacggccct tctcctccgg gctgtaatta gctgagcaag aggtaagggt | 720 |
| ttaagggatg gttggttggt ggggtattaa tgtttaatta cctggagcac ctgcctgaaa | 780 |
| tcactttttt tcaggttgga ccggtgccac catgggggac aaaaaagatg acaagagctc | 840 |
| gcccaagaag agcaaggcca agagcgccg ggacctggat gacctcaaga ggaagtggc | 900 |
| tatgacagag cacaagatgt cagtagaaga ggtctgccgg aaatacaata ctgactgcgt | 960 |
| gcagggtctg acacacagta aagcccagga gatcctagcc cgggatgggc taacgcccct | 1020 |
| cacaccaccg cccaccaccc cagaatgggt caagttctgc cggcagctgt ttggtggctt | 1080 |
| ctctatcctg ctgtggatcg ggcaatcct ttgcttcctg gcctatggca tccaggcagg | 1140 |
| gacggaggat gacccttccg gtgacaatct gtacctgggc atagtgctgg ccgcagtcgt | 1200 |
| gatcatcacc ggctgcttct cctactacca agaagccaag agttctaaga tcatggagtc | 1260 |
| cttcaagaac atggtccccc agcaagccct tgtgatccgg gaaggtgaaa agatgcaggt | 1320 |
| gaatgcggag gaggtggtgg tcgggggacct ggtggagatc aagggtggtg accgggtgcc | 1380 |
| agctgacctg cgcatcatct cggcccatgg ctgcaaggtg gacaactcct ccctgactgg | 1440 |

-continued

```
cgaatctgag cctcagaccc gctccccgga ctgcacacac gacaacccccc tggagactcg    1500 gaacatcacc ttcttttcca ccaactgcgt ggaaggcacc gctcggggtg tggtggtagc    1560
cacaggtgac cgcaccgtca tgggccgcat tgccaccctg gcctcgggct tggaggtggg    1620
caagacgccc atcgccattg agattgagca tttcatccag ctcattacgg gcgtggccgt    1680
gttcctgggc gtgtccttct tcatcctctc tctcattctg ggttacacct ggctcgaggc    1740
agtcatcttc ctcatcggca tcattgtggc caatgtccca gagggctgc tggctactgt     1800 cacggtgtgt ctgacgctga ccgccaagcg catggctcgc aagaactgcc tggtgaagaa    1860
cctggaggcg gtggagacgc tgggctccac gtccaccatc tgctcggaca agaccggcac    1920
tctcacccag aaccgcatga ccgtcgccca catgtggttt gacaaccaga tccacgaggc    1980
agacaccaca gaggatcagt cagggacctc tttcgacaag agctcacaca cctgggtggc    2040
cctgtcccac atcgccgggc tctgcaaccg ggccgtcttc aagggcgggc aggacaacat    2100
cccagtactc aagagggacg tggccggtga tgcctccgag tctgccctgc ttaagtgcat    2160
tgagctgtcc tcgggttccg taaagctgat gcgagaacgg aacaagaaag tggctgagat    2220
tccgttcaac tcgaccaaca aataccagct atccatccat gagactgagg atcccaatga    2280
caaccggtac ctgctagtga tgaagggcgc ccccgaacgc attctggacc gctgtgccac    2340
catcctcctg cagggcaagg agcagcctct ggatgaggag atgaaggagg ccttccagaa    2400
tgcctacctg gagcttggtg gcctgggcga gcgtgtgctg ggtttctgcc attactacct    2460
gcctgaggaa cagttccccca agggctttgc ctttgactgt gatgacgtga acttcaccac    2520
agacaacctt tgctttgtgg gtctcatgtc catgattgac cctccccggg cagccgtccc    2580
tgacgctgtg ggcaaatgcc gaagcgcagg catcaaggtc atcatggtca ccggcgatca    2640
ccccatcact gccaaggcca ttgccaaggg tgtgggtatc atctctgagg gtaacgagac    2700
tgtcgaagac atcgctgccc ggctcaacat ccctgtcagc caggtgaacc ccagggatgc    2760
caaagcctgt gtgattcacg gcaccgacct caaggacttc acctcggagc agattgacga    2820
gattctgcag aaccacaccg agatcgtctt tgcccgaacc tcccctcagc agaagctcat    2880
catcgtggag ggctgtcaga gacagggagc aattgtggct gtgactggcg atggtgtgaa    2940 tgactccccct gctctgaaga aggctgacat cggggtggcc atgggcattg ctggctctga    3000
tgtctctaag caggctgccg acatgattct gctggatgac aactttgctt ccattgtcac    3060
tggtgtggag gaaggccgcc tgatctttga caacctgaag aaatccatcg cctacactct    3120
gactagcaac atccctgaga tcacacccct cctgctcttc atcatggcta acatcccact    3180
gcctcttggc accatcacca tcctctgcat tgacctgggt accgacatgg tccctgcaat    3240
ctccctggcc tacgaggctg ccgagagcga catcatgaag aggcagccca ggaacccacg    3300
cacagacaaa ctggtcaacg aaaggctcat cagcatggcc tacgggcaga ttgggatgat    3360
ccaggccctc ggtggttttct tctcctactt tgtcatcctg gcagaaaatg gcttcttgcc    3420
cggaaacctg gtgggcatcc ggctcaactg ggatgatcgc actgtcaatg acctagaaga    3480
cagttatggg cagcagtgga cttatgagca gaggaaggtg gtagagttca catgccacac    3540
agccttcttt gtgagtatcg tggtggtcca gtgggctgac ctgatcatct gcaagaccag    3600
gaggaactcc gtcttccagc agggcatgaa gaataagatc ttgatcttcg gcttgtttga    3660
ggagacggcc ctcgctgcct tcctgtccta ctgcccaggc atggatgtgg cccttcgcat    3720
gtaccctctc aagcccagct ggtggttctg tgccttcccc tacagtttcc tcatcttcgt    3780
```

| | |
|---|---|
| ctatgatgag attcgcaaac tcatcctgcg caggaacccc ggggggttggg tggagaaaga | 3840 |
| gacctactat tgagatcttt ttccctctgc caaaaattat ggggacatca tgaagcccct | 3900 |
| tgagcatctg acttctggct aataaaggaa atttattttc attgcaatag tgtgttggaa | 3960 |
| tttttttgtgt ctctcactcg gaag | 3984 |

<210> SEQ ID NO 5
<211> LENGTH: 3673
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | |
|---|---|
| ttaattaaac tagacagact gcagagggcc ctgcgtatga gtgcaagtgg gtttttaggac | 60 |
| caggatgagg cggggtgggg gtgcctacct gacgaccgac cccgacccac tggacaagca | 120 |
| cccaaccccc attccccaaa ttgcgcatcc cctatcagag agggggaggg gaaacaggat | 180 |
| gcggcgaggc gcgtcgcgac tgccagcttc agcaccgcgg acagtgcctt cgcccccgcc | 240 |
| tggcggcgcg cgccaccgcc gcctcagcac tgaaggcgcg ctgacgtcac tcgccggtcc | 300 |
| cccgcaaact cccccttcccg gccaccttgg tcgcgtccgc gccgccgccg gcccagccgg | 360 |
| accgcaccac gcgaggcgcg agataggggg cacgggcgc gaccatctgc gctgcggcgc | 420 |
| cggcgactca gcgctgcctc agtctgcggt gggcagcgga ggagtcgtgt cgtgcctgag | 480 |
| agcgcagtcg agaggccacc atgggggaca aaaagatga caagagctcg cccaagaaga | 540 |
| gcaaggccaa agagcgccgg gacctggatg acctcaagaa ggaagtggct atgacagagc | 600 |
| acaagatgtc agtagaagag gtctgccgga atacaatac tgactgcgtg cagggtctga | 660 |
| cacacagtaa agcccaggag atcctagccc gggatgggcc taacgccctc acaccaccgc | 720 |
| ccaccacccc agaatgggtc aagttctgcc ggcagctgtt tggtggcttc tctatcctgc | 780 |
| tgtggatcgg ggcaatcctt tgcttcctgg cctatggcat ccaggcaggg acggaggatg | 840 |
| acccttccgg tgacaatctg tacctgggca tagtgctggc cgcagtcgtg atcatcaccg | 900 |
| gctgcttctc ctactaccaa gaagccaaga gttctaagat catggagtcc ttcaagaaca | 960 |
| tggtcccccca gcaagccctt gtgatccggg aaggtgaaaa gatgcaggtg aatgcggagg | 1020 |
| aggtggtggt cggggacctg gtggagatca aggtggtga ccgggtgcca gctgacctgc | 1080 |
| gcatcatctc ggcccatggc tgcaaggtgg acaactcctc cctgactggc gaatctgagc | 1140 |
| ctcagacccg ctcccccggac tgcacacacg acaacccccct ggagactcgg aacatcacct | 1200 |
| tcttttccac caactgcgtg gaaggcaccg ctcgggtgt ggtggtagcc acaggtgacc | 1260 |
| gcaccgtcat gggccgcatt gccaccctgg cctcgggctt ggaggtgggc aagacgccca | 1320 |
| tcgccattga gattgagcat ttcatccagc tcattacggg cgtggccgtg ttcctgggcg | 1380 |
| tgtccttctt catcctctct ctcattctgg gttacacctg gctcgaggca gtcatcttcc | 1440 |
| tcatcggcat cattgtggcc aatgtcccag aggggctgct ggctactgtc acggtgtgtc | 1500 |
| tgacgctgac cgccaagcgc atggctcgca gaactgcct ggtgaagaac ctggaggcgg | 1560 |
| tggagacgct gggctccacg tccaccatct gctcggacaa gaccggcact ctcacccaga | 1620 |
| accgcatgac cgtcgcccac atgtggtttg acaaccagat ccacgaggca gacaccacag | 1680 |
| aggatcagtc agggacctct ttcgacaaga gctcacacac ctgggtggcc ctgtcccaca | 1740 |
| tcgccgggct ctgcaaccgg gccgtcttca agggcggggca ggacaacatc ccagtactca | 1800 |

-continued

```
agagggacgt ggccggtgat gcctccgagt ctgccctgct taagtgcatt gagctgtcct    1860
cgggttccgt aaagctgatg cgagaacgga caagaaagt ggctgagatt ccgttcaact     1920
cgaccaacaa ataccagcta tccatccatg agactgagga tcccaatgac aaccggtacc    1980
tgctagtgat gaagggcgcc cccgaacgca ttctggaccg ctgtgccacc atcctcctgc    2040
agggcaagga gcagcctctg gatgaggaga tgaaggaggc cttccagaat gcctacctgg    2100
agcttggtgg cctgggcgag cgtgtgctgg gtttctgcca ttactacctg cctgaggaac    2160
agttccccaa gggctttgcc tttgactgtg atgacgtgaa cttcaccaca gacaaccttt    2220
gctttgtggg tctcatgtcc atgattgacc ctccccgggc agccgtccct gacgctgtgg    2280
gcaaatgccg aagcgcaggc atcaaggtca tcatggtcac cggcgatcac cccatcactg    2340
ccaaggccat tgccaagggt gtgggtatca tctctgaggg taacgagact gtcgaagaca    2400
tcgctgcccg gctcaacatc cctgtcagcc aggtgaaccc cagggatgcc aaagcctgtg    2460
tgattcacgg caccgacctc aaggacttca cctcggagca gattgacgag attctgcaga    2520
accacaccga gatcgtcttt gcccgaacct cccctcagca gaagctcatc atcgtggagg    2580
gctgtcagag acaggagca attgtggctg tgactggcga tggtgtgaat gactcccctg    2640
ctctgaagaa ggctgacatc ggggtggcca tgggcattgc tggctctgat gtctctaagc    2700
aggctgccga catgattctg ctggatgaca ctttgcttc cattgtcact ggtgtggagg    2760
aaggccgcct gatctttgac aacctgaaga atccatcgc ctacactctg actagcaaca    2820
tccctgagat cacaccctt ctgctcttca tcatggctaa catcccactg cctcttggca    2880
ccatcaccat cctctgcatt gacctgggta ccgacatggt ccctgcaatc tccctggcct    2940
acgaggctgc cgagagcgac atcatgaaga ggcagcccag gaacccacgc acagacaaac    3000
tggtcaacga aaggctcatc agcatggcct acgggcagat tgggatgatc caggccctcg    3060
gtggtttctt ctcctacttt gtcatcctgg cagaaaatgg cttcttgccc ggaaacctgg    3120
tgggcatccg gctcaactgg gatgatcgca ctgtcaatga cctagaagac agttatgggc    3180
agcagtggac ttatgagcag aggaaggtgg tagagttcac atgccacaca gccttctttg    3240
tgagtatcgt ggtggtccag tgggctgacc tgatcatctg caagaccagg aggaactccg    3300
tcttccagca gggcatgaag aataagatct tgatcttcgg cttgtttgag gagacggccc    3360
tcgctgcctt cctgtcctac tgcccaggca tggatgtggc ccttcgcatg taccctctca    3420
agcccagctg gtggttctgt gccttcccct acagtttcct catcttcgtc tatgatgaga    3480
ttcgcaaact catcctgcgc aggaaccccg ggggttgggg ggagaaagag acctactatt    3540
gagatctttt tccctctgcc aaaaattatg gggacatcat gaagcccctt gagcatctga    3600
cttctggcta ataaaggaaa tttatttca ttgcaatagt gtgttggaat tttttgtgtc    3660
tctcactcgg aag                                                       3673
```

<210> SEQ ID NO 6
<211> LENGTH: 3042
<212> TYPE: DNA
<213> ORGANISM: Homo sapiens

<400> SEQUENCE: 6

```
atgggggaca agaaagatga caaggactca cccaagaaga acaagggcaa ggagcgccgg    60
gacctggatg acctcaagaa ggaggtggct atgacagagc acaagatgtc agtggaagag    120
gtctgccgga atacaacac agactgtgtg cagggtttga cccacagcaa agcccaggag    180
atcctggccc gggatgggcc taacgcactc acgccaccgc ctaccacccc agagtgggtc    240
```

```
aagttttgcc ggcagctctt cgggggcttc tccatcctgc tgtggatcgg ggctatcctc    300
tgcttcctgg cctacggtat ccaggcgggc accgaggacg accectctgg tgacaacctg    360 tacctgggca tcgtgctggc ggccgtggtg atcatcactg gctgcttctc ctactaccag    420
gaggccaaga gctccaagat catggagtcc ttcaagaaca tggtgcccca gcaagccctg    480
gtgatccggg aaggtgagaa gatgcaggtg aacgctgagg aggtggtggt cggggacctg    540
gtggagatca agggtggaga ccgagtgcca gctgacctgc ggatcatctc agcccacggc    600
tgcaaggtgg acaactcctc cctgactggc gaatccgagc cccagactcg ctctcccgac    660
tgcactcacg acaaccccett ggagactcgg aacatcacct tcttttccac caactgtgtg    720
gaaggcacgg ctcggggcgt ggtggtggcc acgggcgacc gcactgtcat gggccgtatc    780
gccaccctgg catcagggct ggaggtgggc aagacgccca tcgccatcga gattgagcac    840
ttcatccagc tcatcaccgg cgtggctgtc ttcctgggtg tctccttctt catcctctcc    900
ctcattctcg gatacacctg gcttgaggct gtcatcttcc tcatcggcat catcgtggcc    960
aatgtcccag agggtctgct ggccactgtc actgtgtgtc tgacgctgac cgccaagcgc   1020
atggcccgga gaactgcctt ggtgaagaac ctggaggctg tagaaaccct gggctccacg   1080
tccaccatct gctcagataa gacagggacc ctcactcaga accgcatgac agtcgcccac   1140
atgtggtttg acaaccagat ccacgaggct gacaccactg aggaccagtc agggacctca   1200
tttgacaaga gttcgcacac ctgggtggcc ctgtctcaca tcgctgggct ctgcaatcgc   1260
gctgtcttca agggtggtca ggacaacatc cctgtgctca gagggatgt ggctggggat    1320 gcgtctgagt ctgccctgct caagtgcatc gagctgtcct ctggctccgt gaagctgatg   1380
cgtgaacgca acaagaaagt ggctgagatt cccttcaatt ccaccaacaa ataccagctc   1440
tccatccatg agaccgagga ccccaacgac aaccgatacc tgctggtgat gaagggtgcc   1500
cccgagcgca tcctggaccg ctgctccacc atcctgctac agggcaagga gcagcctctg   1560
gacgaggaaa tgaaggaggc cttccagaat gcctaccttg agctcggtgg cctgggcgag   1620
cgcgtgcttg gtttctgcca ttattacctg cccgaggagc agttcccccaa gggctttgcc   1680 ttcgactgtg atgacgtgaa cttcaccacg gacaacctct gctttgtggg cctcatgtcc   1740
atgatcgacc cacccgggc agccgtccct gacgcggtgg gcaagtgtcg cagcgcaggc   1800
atcaaggtca tcatggtcac cggcgatcac cccatcacgg ccaaggccat gccaagggt    1860 gtgggcatca tctctgaggg caacgagact gtggaggaca tcgccgcccg gctcaacatt   1920
cccgtcagcc aggttaaccc ccgggatgcc aaggcctgcg tgatccacgg caccgacctc   1980
aaggacttca cctccgagca aatcgacgag atcctgcaga atcacaccga tcgtcttc    2040 gcccgcacat cccccccagca gaagctcatc attgtggagg gctgtcagag acagggtgca   2100
attgtggctg tgaccgggga tggtgtgaac gactccccccg ctctgaagaa ggccgacatt   2160
ggggtggcca tgggcatcgc tggctctgac gtctccaagc aggcagctga catgatcctg   2220
ctggacgaca actttgcctc catcgtcaca ggggtggagg agggccgcct gatcttcgac   2280
aacctaaaga gtccattgc ctacacccctg accagcaata tcccggagat cacgcccttc    2340
ctgctgttca tcatggccaa catcccgctg cccctgggca ccatcaccat cctctgcatc   2400
gatctgggca ctgacatggt ccctgccatc tcactggcgt acgaggctgc cgaaagcgac   2460
atcatgaaga gacagcccag gaaccgcgcg acggacaaat ggtcaatga gagactcatc    2520 agcatggcct acgggcagat tggaatgatc caggctctcg gtggcttctt ctcttacttt   2580
```

```
gtgatcctgg cagaaaatgg cttcttgccc ggcaacctgg tgggcatccg gctgaactgg    2640
gatgaccgca ccgtcaatga cctggaagac agttacgggc agcagtggac atacgagcag    2700
aggaaggtgg tggagttcac ctgccacacg gccttctttg tgagcatcgt tgtcgtccag    2760
tgggccgatc tgatcatctg caagacccgg aggaactcgg tcttccagca gggcatgaag    2820
aacaagatcc tgatcttcgg gctgtttgag gagacggccc tggctgcctt cctgtcctac    2880
tgccccggca tggacgtggc cctgcgcatg taccctctca agcccagctg gtggttctgt    2940
gccttcccct acagtttcct catcttcgtc tacgacgaaa tccgcaaact catcctgcgc    3000
aggaacccag ggggttgggt ggagaaggaa acctactact ga                      3042

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
accggagcca cc                                                         12
```

AAV-MEDIATED DELIVERY OF ATP1A3 GENES TO CENTRAL NERVOUS SYSTEM

This application claims priority, under 35 U.S.C. § 119(e) to U.S. Provisional Application No. 62/654,645, filed on Apr. 9, 2018, which is herein incorporated by reference in its entirety.

SEQUENCE LISTING

The instant application contains a Sequence Listing which has been filed electronically in ASCII format and is hereby incorporated by reference in its entirety. Said ASCII copy, created on Jul. 24, 2019, is named 24892_0200-US_SL.txt and is 23,427 bytes in size.

FIELD OF THE INVENTION

The present invention relates to the delivery and expression of ATP1A3 genes in the central nervous system.

BACKGROUND OF THE INVENTION

Alternating Hemiplegia of Childhood (AHC) is a serious and rare neurodevelopmental disorder, affecting approximately 1 in 1,000,000 children. AHC is caused by de novo loss-of-function mutations in the ATP 1A3 gene (Heinzen et al., 2012; Rosewich et al., 2012). The gene encodes the α3 subunit of the Na+, K+ ATPase, one of two pumps that establish and maintain electrochemical gradients required for the propagation of action potentials in neurons. AHC-associated mutations do not affect expression of ATP 1A3 gene or levels of its protein, but significantly reduce α3 protein functionality (Heinzen et al., 2012; Li et al., 2015). Two most common AHC-associated alleles of ATP1A3 cause D801N and E815K missense substitutions (Heinzen et al., 2012; Rosewich et al., 2012; Sasaki et al., 2014; Viollet et al., 2015).

ATP1A3 gene is expressed in the central nervous system (CNS) and heart of all mammals studied. Brain expression of ATP 1A3 is enriched in high frequency GABAergic interneurons of the cerebellum, pons, basal ganglia, thalamus, cortex and hippocampus (Bøttger et al., 2011; Hieber et al., 1991; McGrail et al., 1991; Pietrini et al., 1992; Richards et al., 2007). While most neurons of the CNS also express ATP1A1 gene that can partially compensate for the loss of ATP1A3 functionality, some neuron types, most notably Purkinje cells of the cerebellum and certain inhibitory interneurons with high-frequency firing rate, do not express ATP1A1, leaving them especially vulnerable to ATP1A3 dysfunction. Clinical symptoms of cerebellar, hippocampal, basal ganglia, and motor cortex dysfunction largely correlate with persistent symptoms of AHC. In line with clinical symptoms, brains of AHC patients show progressive frontal dominant cerebral, severe hippocampal, and diffuse cerebellar atrophy (Sasaki et al., 2017). Paroxysmal symptoms of AHC likely originate in Purkinje cells and spread through the afferent networks of the cerebellum by spreading depolarization ("spreading depression").

AHC symptoms appear before 18 months of age, and often shortly after birth. AHC causes severe morbidity and increased mortality. Patients often suffer severe neurodevelopmental impairments, episodes of paralysis, severe dystonia, ataxia, swallowing problems, epilepsy, status epilepticus, sudden unexpected death, and episodes of developmental regression (Mikati et al., 2000; Panagiotakaki et al., 2015). Currently, there is no effective on-target treatment, although certain off-target drugs like Flunarizine have been reported to have some limited effect on certain symptoms.

Besides AHC, mutations in ATP1A3 gene are associated with at least eight other distinct, but clinically overlapping neurological disorders (Dard et al., 2015; de Carvalho Aguiar et al., 2004; Demos et al., 2014; Heinzen et al., 2014; Paciorkowski et al., 2015; Smedemark-Margulies et al., 2016; Sweadner et al., 2016; Sweney et al., 2015; Yano et al., 2017). The clinical symptoms of these diseases partly intersect and range from mild to severe. The number of patients with pathogenic ATP1A3 alleles is likely to increase if ATP1A3 is included in gene panels for epilepsy-like disorders, as these patients are often misdiagnosed (Algahtani et al., 2017).

There thus remains a need in the art to develop an on-target delivery of ATP1A3 genes and an effective gene therapy treatment of neurological disorders associated with loss-of-function mutations in ATP1A3. This invention answers this need.

SUMMARY OF THE INVENTION

One aspect of the invention relates to a transgenic vector for transducing cells of the central nervous system of a mammal and transgenically expressing a protein in the central nervous system of the mammal. The transgenic vector comprises a virus-derived vector, a nucleic acid sequence encoding the protein, and an endogenous ATP1A3 promoter ($P_{ATP1A3}$) sequence.

One aspect of the invention relates to a composition comprising a recombinant adeno-associated virus (AAV) vector comprising a nucleic acid sequence encoding a ATP1A3 (sodium/potassium-transporting ATPase subunit alpha-3) protein, in a form compatible with administration into the central nervous system.

Another aspect of the invention relates to a method for treating a subject having a neurological disorder associated with mutations in the ATP1A3 gene. The method comprises administering into the central nervous system (CNS) of the subject a recombinant adeno-associated virus (AAV) vector comprising a nucleic acid sequence encoding a ATP1A3 protein, thereby restoring some degree of neurological function in said subject.

Another aspect of the invention relates to a method for delivering to the central nervous system of a mammal, a ATP1A3 DNA that is expressed in a cell of the central nervous system. The method comprises administering into the central nervous system of the mammalian a recombinant AAV vector comprising a nucleic acid sequence encoding a ATP1A3 protein, wherein said vector transduces the cell.

Additional aspects, advantages and features of the invention are set forth in this specification, and in part will become apparent to those skilled in the art on examination of the following, or may be learned by practice of the invention. The inventions disclosed in this application are not limited to any particular set of or combination of aspects, advantages and features. It is contemplated that various combinations of the stated aspects, advantages and features make up the inventions disclosed in this application.

DETAILED DESCRIPTION OF THE INVENTION

Figure 1:
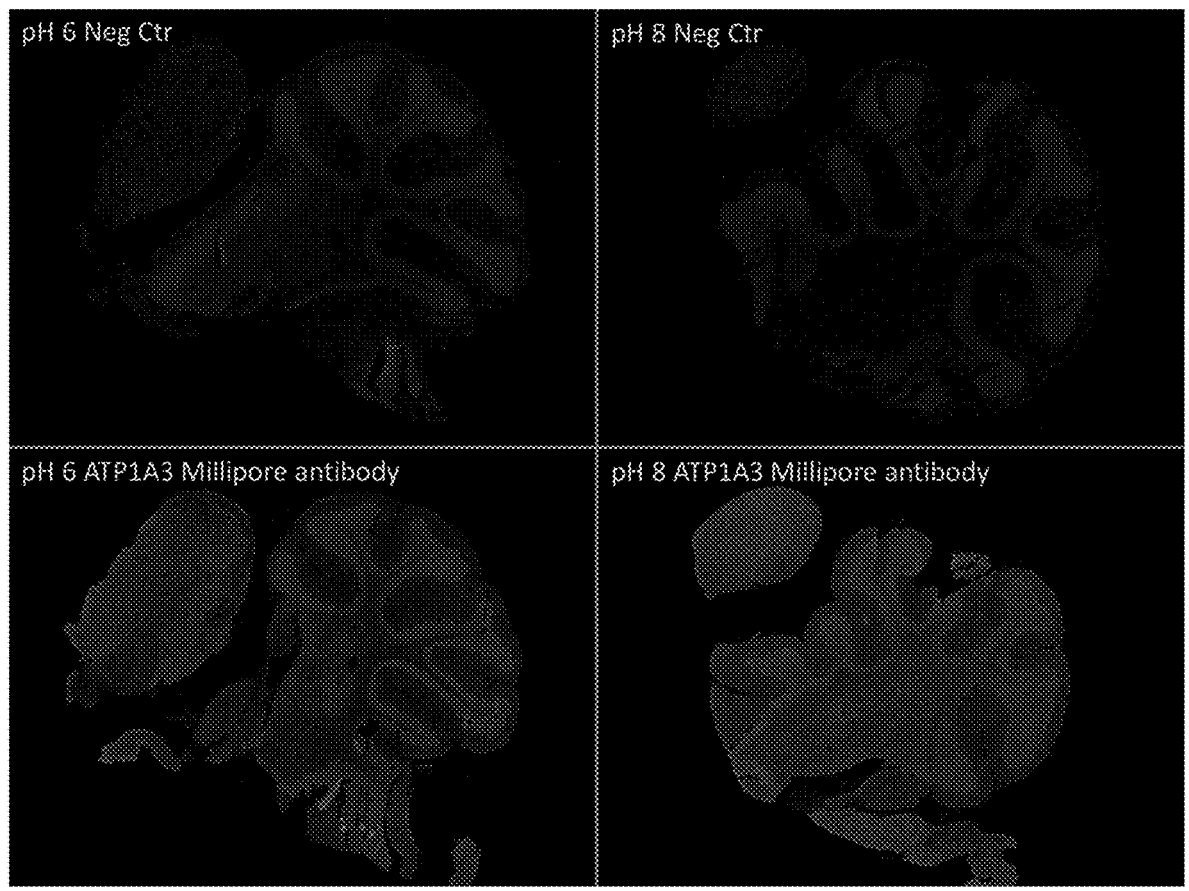
FIG. 1 depicts ATP1A3 (Millipore #06-172-1) staining in a mouse cerebellum. All images were acquired with the same microscope settings (exposure time, image dynamic range).

One aspect of the invention relates to a transgenic vector for transducing cells of the central nervous system of a mammal and transgenically expressing a protein in the central nervous system of the mammal. The transgenic vector comprises a virus-derived vector, a nucleic acid sequence encoding the protein, and an endogenous ATP1A3 promoter $P_{ATP1A3}$) sequence.

Suitable viral vectors include those neurotrophic viral vectors, including, but not limited to, adeno-associated viral vectors (AAV), herpes simplex viral vectors and lentiviral vectors. More discussions about the herpes simplex viral vectors may be found in U.S. Pat. No. 5,672,344, which is incorporated herein by reference in its entirety.

All the descriptions and embodiments relating to the AAV vectors discussed in a different aspect of the invention, infra, are suitable for this aspect of the invention.

The transgenic vector also comprises a nucleic acid sequence encoding a protein (DNA encoding the protein, e.g., cDNA of protein), the transgene. The transgene encodes a biologically active protein which is transgenically expressed in the central nervous system of a mammal. The transgene may be ATP1A3 (sodium/potassium-transporting ATPase subunit alpha-3). The transgenes may also be insulin growth factor-1 (IGF-1), calbindin D28, parvalbumin, HIF1-alpha, SIRT-2, VEGF, SMN-1, SMN-2, CNTF (Ciliary neurotrophic factor), sonic hedgehog (shh), erythropoietin (EPO), lysyl oxidase (LOX), progranulin, prolactin, ghrelin, neuroserpin, or placenta lactogen.

The protein-coding nucleic acid may be an DNA sequence, an "exogenous DNA" that is exogenous to both AAV and to the target cell. The DNA may be synthetic DNA, complementary DNA, genomic DNA, or a combination thereof. The DNA may be of any sequence or length, provided that it may be incorporated into the vector and delivered to target cells. Typically, because of the packaging limitations of AAV, the exogenous DNA will have a length of up to 4,400 bases.

More than one transgene can be delivered by the transgenic vector, e.g., via more than one virus-derived vector. For instance, the transgenic vector comprises multiple AAV vectors and each AAV vector comprises a transgene operably linked to a promoter.

The protein-coding nucleic acid is operably linked to a promoter sequence to enable the expression of the trangene from a single AAV vector. For the gene to be expressible, the protein-coding nucleic acid shall be operably linked to a promoter sequence so that when the promoter is activated, the coding sequence is transcribed. The protein-coding nucleic acid is operably linked if the linkage does not cause an error in the reading of the downstream sequence. To be "operably linked," it is not necessary that two sequences be immediately adjacent to one another.

The promoter sequence drives transcription of the transgene and defines the cellular specificity of its expression. The promoter sequence is an endogenous ATP1A3 promoter $P_{ATP1A3}$) sequence. In one embodiment, the $P_{ATP1A3}$ promoter comprises a mouse promoter sequence, SEQ ID NO: 1. In one embodiment, the $P_{ATP1A3}$ promoter comprises a homologous human sequence.

The transgenic vector may further comprise one or more nucleic acid regulatory sequence, linked directly or indirectly to the protein-coding nucleic acid sequence. For instance, a promoter specific to the gene may be incorporated into the transgenic vector. In certain embodiments, the nucleic acid regulatory sequence comprises a sequence to regulate ribosome binding and/or translation efficiency of the ATP1A3 gene. In certain embodiments, the nucleic acid regulatory sequence comprises a 3'-UTR sequence that contains a polyadenylation sequence.

All the descriptions and embodiments relating to the nucleic acid regulatory sequences discussed in a different aspect of the invention, infra, are suitable for this aspect of the invention.

In certain embodiments, the transgenic vector comprises an AAV vector (e.g., a recombinant AAV vector), a $P_{ATP1A3}$ promoter, and a mCherry transgene.

In certain embodiments, the transgenic vector comprises AAV9 vector (e.g., recombinant AAV9 vector), a $P_{ATP1A3}$ promoter, a mCherry transgene, a sequence to regulate ribosome binding and/or translation efficiency, and a 3'-UTR sequence that contains a polyadenylation sequence. In one embodiment, the transgenic vector comprises SEQ ID NO: 2.

In certain embodiments, the transgenic vector comprises an AAV vector (e.g., a recombinant AAV vector), a $P_{ATP1A3}$ promoter, and a ATP1A3 transgene.

In certain embodiments, the transgenic vector comprises AAV9 vector (e.g., recombinant AAV9 vector), a $P_{ATP1A3}$ promoter, a ATP1A3 transgene, a sequence to regulate ribosome binding and/or translation efficiency, and a 3'-UTR sequence that contains a polyadenylation sequence. In one embodiment, the transgenic vector comprises SEQ ID NO: 3.

Also disclosed herein are compositions and methods for intracisternal or intrathecal administration of recombinant AAV comprising a gene that affects neurological function. The embodiments of the invention illustrate that some neurological disorders associated with loss-of-function mutations of ATP1A3 genes (e.g., alternating hemiplegia of childhood, "AHC") can be better addressed with a more targeted delivery of the gene therapy. For instance, the phenotype of an AHC mouse model has been rescued by transgenesis. Inclusion of extra-chromosomal copies of ATP1A3 by transgenesis has been shown to be sufficient to increase Na+, K+ ATPase activity in the brain and confer significant phenotypic improvements compared to non-transgenic mice with the same AHC associated mutation. This demonstrates that the presence of additional copies of functional ATP1A3 genes can compensate for lack of function in a disease-associated genomic allele of ATP1A3 and rescue the associated phenotypes.

One aspect of the invention relates to a composition comprising a recombinant adeno-associated virus (AAV) vector comprising a nucleic acid sequence encoding a ATP1A3 (sodium/potassium-transporting ATPase subunit alpha-3) protein, in a form compatible with administration into the central nervous system.

AAV vector

The composition contains an adeno-associated virus (AAV) vector. The vector may be a derivative of the adeno-associated virus, into which exogenous DNA is introduced.

One purpose is to rescue the phenotypes caused by ATP1A3 insufficiency by delivering additional copies of functional ATP1A3 cDNA to the neurons of the CNS. AAV vector is used herein as a carrier to deliver ATP1A3 cDNA.

AAV is a replication-defective, non-enveloped parvovirus, present in humans and some other primate species but not associated with any pathology. Recombinant AAV vectors are used for the development of human therapeutics because they can infect quiescent non-dividing cells (like neurons), mediate long-term gene expression, and, unlike retroviruses, persist in an extrachromosomal state without integrating into the genome of the host cell. Since AAV does not integrate into the host genome, the use of this viral vector mitigates risks associated with unintended off-target effects of genomic editing (Schaefer et al., 2017; Zhang et al., 2015).

AAV vectors are derived from single-stranded (ss) DNA parvoviruses that are nonpathogenic for mammals. Briefly, recombinant AAV-based vectors have two open reading frames, the rep and cap viral genes that account for 96% of the viral genome removed, leaving the two flanking 145-basepair (bp) inverted terminal repeats (ITRs), which are used to initiate viral DNA replication, packaging and integration. These ITRs allow for synthesis of the complementary DNA strand. Rep and Cap are translated to produce multiple distinct proteins. When constructing an AAV transfer plasmid, the transgene is placed between the two ITRs, and Rep and Cap are supplied in trans. In the absence of helper virus, wild-type AAV is typically maintained episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, which is incorporated herein by reference in its entirety, may nearly double this limit.

In one embodiment, small (4.8 kb) ssDNA AAV genome having ITR sequences flanking the insert are of ITR2 serotype.

AAV vector of any serotype can be used. Particular useful serotypes are those that are particularly suitable for nervous cells, e.g., AAV1, AAV2, AAV4, AAV5, AAV8, AAV9, AAV-PHP.B, or AAVrh10. Several of these AAV serotypes have been utilized in clinical Phase I and II studies for diseases that require CNS delivery (reviewed in (Naso et al., 2017)). Initial testing of AAV2-based RPE65 delivery has been done in canine culture. Other serotype besides those listed herein can be used. Furthermore, pseudotyped AAV vectors may also be used herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5, capsid and the AAV 2 genome.

Those skilled in the art will be familiar with the preparation of functional AAV-based gene therapy vectors. Methods of AAV production, purification, and preparation for administration to human subjects can also be found in the art (see, e.g., Viral Vectors for Gene Therapy: Methods and Protocols, ed. Machida, Humana Press, 2003, which is incorporated herein by reference in its entirety).

Additionally, AAV-based gene therapy targeted to cells of the CNS has been described in U.S. Pat. Nos. 6,180,613 and 6,503,888, which are incorporated by reference in their entirety.

Exemplary AAV vectors are recombinant AAV vectors encoding human protein.

In certain embodiments, the AAV vector is AAV9 vector. In these embodiments, AAV9 vector is used to deliver a rescue gene to the CNS neurons (e.g., in a mammal, such as mouse, primate, human). Cell-specificity of AAV infection is determined by the capsid serotype. AAV serotype 9 (AAV9) has natural tropism for neurons and was successfully applied to rescue adult mouse models of diseases such as mucopolysaccharidosis (Fu et al., 2010; Hinderer et al., 2016; Watson et al., 2006) and diabetic neuropathy (Homs et al., 2014). Injection of AAV9 into cerebrospinal fluid has been highly efficient in targeting the CNS in adult mice (Bey et al., 2017; Fu et al., 2010) and pigs (Federici et al., 2012). Large comparative analysis of AAV serotypes 1, 2, 5, 8 and 9 in mouse and macaque brains showed that AAV9 exhibited high efficiency cortical neuron transduction (>70%) when used in conjunction with neuron-specific promoter (Watakabe et al., 2015). AAV9 vectors showed preferentially higher selectivity of neuronal transduction in adult non-human primate compared to other serotypes (El-Shamayleh et al., 2017).

In an illustrative embodiment, the gene therapy is conducted in various mouse models (that phenocopy many clinical symptoms of AHC) by injecting ATP1A3 DNA-carrying AAV9 capsids into cerebrospinal fluid (via injection into cisterna magna), using a similar method used to rescue adult mouse models of Mucopolysaccharidosis (Hinderer et al., 2016; Watson et al., 2006; DiRosario et al., 2010) and diabetic neuropathy(J. Homs et al., 2014).

ATP1A3 Coding Sequence

The ATP1A3-coding nucleic acid may be a DNA sequence, an "exogenous DNA" that is exogenous to both AAV and to the target cell. For gene therapy of any genetically-based or genetically-acquired neurological disorder in a subject, DNA delivered to that subject may be considered exogenous even though it is identical to a gene native to that subject's species, provided it differs in the regulatory or coding region from the cognate gene of the subject to whom it is delivered, and therefore encodes a different gene product or is expressed to a different degree and/or in different cells, under at least some conditions.

The DNA may be synthetic DNA, complementary DNA, genomic DNA, or a combination thereof. The DNA may be of any sequence or length, provided that it may be incorporated into the vector and delivered to target cells. Typically, because of the packaging limitations of AAV, the exogenous DNA will have a length of about 10-5,000 bases, e.g., 100 to 4,000 bases. The size of a typical ATP1A3 cDNA (~3 kb) fits within the carrying capacity of AAV vectors (4.4 kb). In one embodiment, a mouse ATP1A3 cDNA sequence is used in ATP1A3-AAV9 vector for gene therapy used in mouse for compatibility. For instance, a sequence of the most common transcript isoform of mouse ATP1A3 gene, NCBI reference sequence NM_001290469.1, may be used. In this embodiment, only the ORF portion of the mRNA is included: from ATG start to TGA stop codons (including the latter).

In one embodiment, a human ATP1A3 cDNA sequence is used in ATP1A3-AAV9 vector for gene therapy used in human for compatibility. For instance, a sequence of the most abundant transcript of human ATP1A3 gene, NCBI reference sequence NM_152296.4 (SEQ ID NO: 6), may be used.

In one embodiment, no tags are added to its coding sequence in order not to interfere with transgenic ATP1A3 protein translation, folding, transport and function.

Regulatory Sequences

In the CNS gene therapy applications, it is necessary to control transcriptional activity. Pharmacological regulation of gene expression with the viral vectors can been obtained by including various regulatory elements as described below. The precise nature of regulatory regions needed for gene expression may vary from organism to organism.

In certain embodiments, the composition further comprises one or more nucleic acid regulatory sequences, linked directly or indirectly to the ATP1A3-coding nucleic acid sequence.

Promoter

In certain embodiments, the nucleic acid regulatory sequence comprises a promoter sequence that renders the expression of the ATP1A3-coding nucleic acid sequence CNS-specific. The promoters have the ability to drive the ATP1A3 expression in target areas in central nervous system. The promoter sequence can be neuron-specific or glia-specific.

In some embodiments, a promoter specific to the gene is incorporated into the AAV construct. Inclusion of gene-specific promoters in recombinant AAVs for gene delivery provides the desired specificity for neuronal transduction and expression within particular target cells in the brain that is not possible with promoters with non-specific expression profile, like CMV (Watakabe et al., 2015). The use of specific promoters to restrict transgene expression was utilized successfully in several gene delivery studies on non-human primates. A 300bp TH promoter in AAV vector was used to drive expression in dopaminergic neurons of macaques, achieving a specificity of 95% (Stauffer et al., 2016). Similarly, short 530bp enhancer sequence Dlx was used to drive GFP expression in GABAergic neurons of marmosets, achieving a specificity of 93% (Dimidschstein et al., 2016). 1 kb-long L7/Pcp2 promoter was used to drive ChR2 expression in Purkinje neurons with 96% selectivity (El-Shamayleh et al., 2017).

In certain embodiments, the promoter sequence comprises an endogenous ATP1A3 promoter $P_{ATP1A3}$); a human neuron-specific promoter with a strong bias towards inhibitory neuron ($P_{hSyn}$); or an artificial composite promoter comprising CMV enhancer, chicken β-actin promoter, and MVM intron ($P_{CBh}$).

In some embodiments, an endogenous ATP1A3 promoter is employed. In one embodiment, a pig ATP1A3 promoter is employed. In one embodiment, a mouse ATP1A3 promoter is employed (see, e.g., SEQ ID NO: 1). In one embodiment, a primate ATP1A3 promoter is employed. In one embodiment, a human ATP1A3 promoter is employed.

In an illustrative embodiment, the promoter sequence comprises an endogenous ATP1A3 promoter $P_{ATP1A3}$) consisting of −407/+143 of mouse genomic sequence where "/" indicates the transcription start site. Mouse ATP1A3 −407/+143 promoter sequence is based on minimal pig and rat ATP1A3 promoters that were sufficient for neuronal expression in vivo (Benfante et al., 2005; Henriksen et al., 2013; Pathak et al., 1994). To avoid redundancy in having two ribosome binding sites in the constructs, the promoter is shortened to +143 to exclude endogenous Kozak sequence immediately adjacent to the start codon. This minor shortening may not have a significant negative effect on transgene expression, because −210/+77 rat sequence of ATP1A3 promoter was sufficient to drive brain-specific transgene expression in mice in vivo (Pathak et al., 1994).

In another illustrative embodiment, the promoter sequence comprises 488bp-long promoter of porcine ATP1A3 closely homologous to human, which was sufficient to drive GFP expression in Zebrafish brain and spinal cord (Henriksen et al., 2013). Because porcine ATP1A3 promoter was sufficient to drive expression in evolutionarily-distant Zebrafish, it may be sufficient to drive expression on closer-related mammal, like the mouse. In total, 550 nt promoter +3 kb cDNA −133nt rabbit beta globin polyA sequence totals 3,683nt and thus fits within the 4.4 kb payload capacity of AAV.

Alternatively, in some embodiments, a 530bp enhancer sequence Dlx upstream of the promoter may be additionally included (Dimidschstein et al., 2016).

In other embodiments, the cytomegalovirus CMV promoter is employed to drive mouse ATP1A3 cDNA expression.

In another illustrative embodiment, the promoter sequence comprises an artificial composite promoter ($P_{CBh}$) consisting of CMV enhancer, chicken β-actin promoter, and MVM intron (Gray et al., 2011). This promoter can drive strong, albeit not cell-specific, expression in mammalian cells.

In another illustrative embodiment, the promoter sequence comprises a human neuron-specific promoter ($P_{hSyn}$) with "strong, but not exclusive bias towards inhibitory neurons" (Nathanson et al., 2009). Because endogenous ATP1A3 is preferentially expressed in GABAergic (inhibitory) neurons, this promoter may be a safe choice to drive ATP1A3 expression in clinically relevant neurons of the AHC mice.

Ribosome Binding Site

In certain embodiments, the nucleic acid regulatory sequence comprises a sequence to regulate ribosome binding and/or translation efficiency of the ATP1A3 gene. For instance, a Kozak sequence is included to maximize the ribosome binding and translation efficiency of the supplied transgenic ATP1A3.

In certain embodiments, GCCACC sequence was included. This sequence represents the most common conserved RBS (ribosome binding site). In certain embodiments, aCCGGAgccacc sequence (SEQ ID NO: 7) was included. In one embodiment, the sequence to regulate ribosome binding and/or translation efficiency of the ATP1A3 gene is included at the 3' end of the promoters immediately in front of the ATG start codon of the subsequence ATP1A3 ORF.

3' UTR and Poly (A) Signal

The non-coding region 3' to the protein-coding sequence may be retained for its transcriptional termination regulatory sequences, such as those which provide for termination and polyadenlylation. By retaining the 3'-region naturally contiguous to the coding sequence, the transcriptional termination signals may be provided. Where the transcriptional termination signals natively associated with the coding sequence are not satisfactorily functional in the expression host cell, then a different 3' region, functional in the host cell, may be substituted.

In certain embodiments, the nucleic acid regulatory sequence comprises a 3'-UTR sequence that contains a polyadenylation sequence. In one embodiment, the 3'-UTR sequence is a rabbit beta globin polyadenylation sequence (rBGpA). For instance, 127-bp rabbit beta globin polyadenylation (rBGpA) sequence is employed as the 3'UTR due to its small size and proven effectiveness.

In certain embodiments, the recombinant AAV vector comprises an AAV vector, a $P_{ATP1A3}$ promoter, and a ATP1A3 cDNA. In certain embodiments, the recombinant AAV vector comprises an AAV9 vector, a $P_{ATP1A3}$ promoter, a ATP1A3 cDNA, a sequence to regulate ribosome binding and/or translation efficiency, and a 3'-UTR sequence that contains a polyadenylation sequence.

In one embodiment, the recombinant AAV vector comprises AAV9/$P_{ATP1A3}$-ATP1A3 cDNA-rBGpA.

In one embodiment, the recombinant AAV vector comprises SEQ ID NO: 3.

In certain embodiments, the recombinant AAV vector comprises an AAV vector, a $P_{hSyn}$ promoter, and a ATP1A3 cDNA. In certain embodiments, the recombinant AAV vector comprises an AAV9 vector, a $P_{hSyn}$ n promoter, a ATP1A3 cDNA, a sequence to regulate ribosome binding and/or translation efficiency, and a 3'-UTR sequence that contains a polyadenylation sequence.

In one embodiment, the recombinant AAV vector comprises AAV9/$P_{hSyn}$-ATP1A3 cDNA-rBGpA.

In one embodiment, the recombinant AAV vector comprises SEQ ID NO: 4.

In certain embodiments, the recombinant AAV vector comprises an AAV vector, a $P_{CBh}$ promoter, and a ATP1A3 cDNA. In certain embodiments, the recombinant AAV vector comprises an AAV9 vector, a $P_{CBh}$ promoter, a ATP1A3 cDNA, a sequence to regulate ribosome binding and/or translation efficiency, and a 3'-UTR sequence that contains a polyadenylation sequence.

In one embodiment, the recombinant AAV vector comprises AAV9/$P_{CBh}$-ATP1A3 cDNA-rBGpA.

In one embodiment, the recombinant AAV vector comprises SEQ ID NO: 5.

Another aspect of the invention relates to a method for treating a subject having a neurological disorder associated with mutations in the ATP1A3 gene. The method comprises administering into the central nervous system (CNS) of the subject a recombinant adeno-associated virus (AAV) vector comprising a nucleic acid sequence encoding a ATP1A3 protein, thereby restoring some degree of neurological function in said subject.

Mutations in the ATP1A3 gene alone account for nine different neurological disorders. The neurological disorder may be selected from the group consisting of alternating hemiplegia of childhood (AHC); rapid-onset dystonia-parkinsonism (RDP); cerebellar ataxia, areflexia, pes cavus, optic atrophy, and sensorineural hearing loss (CAPOS); early infantile epileptic encephalopathy (EIEE); relapsing encephalopathy with cerebellar ataxia (RECA); dystonia, dysmorphism, encephalopathy, MRI abnormalities, no hemiplegia (D-DEMO); familial hemiplegic migraine (FHM); childhood onset schizophrenia (COS); childhood rapid onset ataxia (CROA); and auditory neuropathy spectrum disorder (ANSD). All patients with loss-of-function ATP1A3 mutations can benefit directly from the ATP1A3-based gene therapy.

The method can restore alpha-3-specific NaK-ATPase activity in the central nervous system, thereby restoring some degree of neurological function in symptomatic mammals (animals or humans) with mutations in ATP1A3 gene. The method can restore ATP1A3 function in GABAergic neurons in the CNS, which includes Purkinje neurons of the cerebellum.

Another aspect of the invention relates to a method for delivering to the central nervous system of a mammal, a ATP1A3 DNA that is expressed in a cell of the central nervous system. The method comprises administering into the central nervous system of the mammalian a recombinant AAV vector comprising a nucleic acid sequence encoding a ATP1A3 protein, wherein said vector transduces the cell.

A "subject," "individual," or "patient" is used interchangeably herein, which refers to a vertebrate, e.g., a mammal. Mammals include, but are not limited to, mice, rats, simians, humans, farm animals, sport animals, and pets. In certain embodiments, the subject is human.

In certain embodiments, the intended developmental stage (age) of the administration into the subject is neonate, pediatric, or juvenile (pre-adult).

All the descriptions and embodiments relating to the recombinant AAV vectors, including various AAV vectors, various ATP1A3-coding nucleic acid sequences, and various types of regulator sequences (including promoters, sequences to regulate ribosome binding, and 3'-UTR sequences), discussed in the above aspect of the invention relating to a composition, are applicable for these aspects of the invention relating to a method of treatment or a method of delivery.

This gene therapy/delivery method has been tested in various available AHC mouse models by injecting ATP1A3 cDNA-carrying AAV capsids into CSF (via intrathecal or intracisternal injection), using a similar method used to rescue adult mouse models of Mucopolysaccharidosis and diabetic neuropathy. This approach provides a safer and more imminently testable approach than genomic editing, and a targeted and rapid path to long-term treatment. Because AAV does not integrate into the genome, the methods described herein also mitigate risks associated with unintended off-target effects of genomic editing.

Administration/Delivery

In these aspects of the invention relating to a method of treatment or a method of delivery, the recombinant AAV vector may be administered to one or more CNS components selected from the group consisting of cerebrospinal fluid (CSF), cisterna magna (cerebellomedullaris cistern), the spinal cord, brainstem (medulla, pons, and midbrain), hippocampus, cerebellum, diencephalon (thalamus, hypothalamus), and telencephalon (corpus striatum, cerebral cortex, or, within the cortex, the occipital, temporal, parietal or frontal lobes).

The recombinant AAV vector may be delivered to one or more of these CNS components via intracisternal, intrathecal, or intracerebroventricular injection.

One purpose is to maximize distribution of the recombinant AAV vector throughout neurons of the CNS. The AAV vector injection can be optimized for cerebellar (Purkinje neuron) targeting.

Sites of AAV injection can include intravenous, intrathecal (IT), intra-cisterna magna (ICM), intraparenchymal, intraventricular, and intracerebroventricular. Intravenous administration of AAV is associated with severe hepatotoxicity risk, immunological response, and is least efficient in CNS penetration due to the blood-brain barrier (Hinderer et al., 2018). Additionally, both intraventricular and intraparenchymal routes require invasive intracranial surgery, and the latter has shown very limited distribution of transduction (Hardcastle et al., 2018).

Administration of recombinant AAV vector directly into the cerebrospinal fluid (CSF) can deliver the vector directly to the CNS (bypassing the blood brain barrier), distribute it around and throughout the nervous system, and result in wide pattern of neuronal transduction without transfecting internal organs (Federici et al., 2012), thus bypassing immunological response and eliminating the risk of hepatic cytotoxicity associated with intravenous administration (Hinderer et al., 2018). CSF delivery of AAV9 is proven safe and highly efficient in targeting the CNS in various mammals, such as adult mice and pigs.

Additionally, direct injection into CSF requires 100x lower dosage than intravenous delivery (Guo et al., 2016). Since transduction rates are highest near the site of delivery, injection of the recombinant vector at the level of cisterna magna (cerebellomedullary cistern, ICM) below the cerebellum can ensure direct and maximal exposure of the vector to cerebellar, hippocampal, brain stem, and cortical regions that show high levels of ATP1A3 expression and are responsible for locomotor and memory impairments in AHC patients.

The intra-cisterna magna (ICM) route of the AAV injection results in superior CNS distribution of AAV vectors compared with other routes of CSF access (Hinderer et al., 2014).

Administration of AAV directly into the CSF fluid through an intrathecal (IT) route circulates AAVs throughout the CNS and results in widespread CNS transduction. For example, IT administration of $2 \times 10^{11}$ vg of AAV9 in pigs resulted in broad spinal motor neuron and extensive cerebellum transduction, with undetectable levels of peripheral organ transduction (Federici et al., 2011). Intrathecal delivery of contrast media, anesthetics, chemotherapeutic agents and drugs for dystonia, spasticity or pain is routinely performed in human medicine. Alternatively, even less invasive IT injection into lumbar cistern was sufficient to achieve broad and efficient transfection of the spinal cord, pons, cerebellum and other CNS parts in mice (Guo et al., 2016).

Intrathecal injection is desirable for AAV delivery because it is:

a) less surgically invasive than intracranial delivery method;
b) more direct and efficient for cerebellar targeting compared to an intravenous method;
c) less likely to cause peripheral organ toxicity than intravenous method (requires lower 1OOx lower dosage (Guo et al., 2016));
d) familiar to medical personnel and widely practiced in human medicine (for other purposes); and
e) already tested and shown effective for gene delivery into CNS in mice, pigs, and non-human primates.

The injection dosage for the intracerebroventricular, IT, or IV administration into the CSF fluid of a mammal should be an effective dose, or effective multiple doses, of the composition comprising the recombinant AAV vector. A single dose may range from $1 \times 10^9$ vg (vector genomes)/kg dose to $1 \times 10^{15}$ vg/kg, for instance, from $0.5 \times 10^{10}$ vg dose to $5 \times 10^{11}$ vg/kg, from $1 \times 10^{10}$ vg/kg to $5 \times 10^{11}$ vg/kg, or from $1 \times 10^{12}$ vg/kg to $1 \times 10^{14}$ vg/kg. For instance, a single dose injected into a mouse brain (via intracisternal or intraventricular injection) may range from $1 \times 10^9$ vg/kg to $1 \times 10^{12}$ vg/kg.

In experimental mice, the total volume of injected AAV solution is, for example, between 1 to 20 µl. For other mammals, including the human brain, volumes and delivery rates are appropriately scaled. For example, it has been demonstrated that volumes of 150 µl can be safely injected in the primate brain (Janson et al. (2002) Hunt. Gene Ther. 13:1391-1412). Treatment may consist of a single injection per target site, or may be repeated in one or more target sites. Injections can be single or multiple, unilateral or bilateral.

In an illustrative embodiment, experimental results have proven that the gene-coding AAV9 vectors are capable of transducing cerebellum and increasing a protein and activity levels. For instance, an endogenous mouse ATP1A3 promoter $P_{ATP1A3}$) was used in AAV9 vector, and the results show that expression of mCherry protein in the neurons of ventral cerebellum was detected in mice injected with the AAV9 vector with mouse $P_{ATP1A3}$ promoter driving mCherry. The sequence of such recombinant AAV9 is shown in SEQ ID NO: 2.

In another illustrative embodiment, experimental results have proven that the gene-coding AAV9 vectors are capable of transducing brainstem and increasing a protein levels. The results show the presence of mCherry protein in mouse brainstem following injection of a recombinant vector comprising AAV9/$P_{ATP1A3}$-mCherry cDNA-rBGp(A): there were visible quantity of mCherry protein in cross-sections of the six brain stems of injected mice. The sequence of such recombinant AAV9 is shown in SEQ ID NO: 2.

These results indicate that the endogenous $P_{ATP1A3}$ promoter-containing AAV9 vector can transduce neurons of the CNS in mouse in vivo. The results also indicate that the $P_{ATP1A3}$ promoter supports protein expression in neurons of the brainstem in vivo after 4 weeks. Additionally, the results suggest that the endogenous $P_{ATP1A3}$ promoter-containing AAV9 vector would be able to drive expression (transcription and translation) of the protein code it carries in Purkinje neurons.

The presence of mCherry protein in mouse brainstem following the injection of AAV9/$P_{ATP1A3}$-mCherry cDNA-rBGp(A) is significant. This is because for a transgenic protein to be present in detectable amounts in the tissue, a sequential series of processes have to occur:
  Membrane receptor binding and internalization of the AAV vector from the extracellular space into the intracellular neuronal space.
  Synthesis of the second (complementary) strand on the viral DNA (the injected vector's DNA is single-stranded).
  Transcription: recognition and binding of the expression cassette's regulatory elements by the endogenous transcription machinery, RNA Polymerase and cis-acting transcription factors, in order to synthesize messenger RNA (mRNA) from the DNA.
  Translation: recognition and binding of the regulatory elements in the mRNA by the endogenous translation machinery (ribosome and associated proteins) to synthesize and fold protein based on the mRNA.
The successful completion of each of these processes is critical; if any of these processes is not working, there is no protein expression at the end. Each of these processes requires separate elements to initiate, support, and terminate each process. Therefore, the whole design process is very unpredictable, because there are lots of elements for errors and lots of steps where the process can fail.

Successful design of a DNA cassette that supports all these processes and that still fits into a AAV9 capsid is therefore significant, because it needs to include not only the coding sequence for the desired protein, but also has all the necessary regulatory elements to support DNA synthesis (second strand) and transcription (mRNA synthesis) and translation processes (protein synthesis and folding).

In this illustrative example, assembled together was an exogenous DNA construct from mouse ($P_{ATP1A3}$ promoter), rabbit (rBGp(A) sequence), jellyfish (mCherry), some generic eukaryotic elements (Kozak sequence), and viral AAV2 DNA (ITR elements). To generate such an exogenous DNA construct that would be recognized by the endogenous cellular machinery in the mouse CNS to drive the various processes to produce new protein in vivo in an amount that, when distributed throughout the expressing neuron, would be visible in a cross-section of the brainstem—this was a very challenging task, particularly in combination with the another factor that all these elements of the DNA construct need to fit within very stringent size constraints of the DNA load that an AAV vector can carry.

Therefore, this is a surprising success, even if some DNA elements may have been shown to work elsewhere in other constructs. This is true even though AAV9 serotype is known to have affinity for transfecting neurons (as compared to other AAV types), because the cellular specificity of AAV9 transduction and protein expression is very influenced by the promoter it carries in its DNA (Watakabe et al., 2015). In fact, the specific AAV9 assembly of the parts is new and unique and there is no predictability that all the individual parts would work together (be sufficient to do their job without interfering with the others'). It is the combination of specific capsid serotype and the promoter together that results in the transduction efficiency and cellular tropism (specificity) of transgenic construct expression. The risk factor increases when the DNA construct contains untested components (in this case, the endogenous mouse $P_{ATP1A3}$ promoter).

EXAMPLES

The following examples are given as particular embodiments of the invention and to demonstrate the practice and advantages thereof. It is to be understood that the examples are given by way of illustration and are not intended to limit the specification or the claims that follow in any manner.

```
Exemplary rAAV9 sequences:
An exemplary mouse promoter P_ATP1A3 sequence
                                       (SEQ ID NO: 1)
acatactgcaagatggtggcactctggggccctgcattactgcaat tcactgggcctttcctcccaccctgtatctaccccactcccagaag gaggcagattccagggtgcctcaccctcaaagcctcggtccctaag atacctccctatattgaggggggtctctgagtccccaccctgggg atgtccgggatcaccccccccccgcactgtgctcagcttctcag tggccgccactttgcagaaacaaggttggagcggtgaggggggaa gggggagtacagctgcagtactggggccgggccgcaagctgtccg tctgctcagtactgctcctgattggccggagccgcctcccccgcg ggcgcgggcatatgaggaggeggaggccccggccgccgcAgcctct gtgcggtgggacccacggaccgacagacgcacgctcccaccgcggc gcgggcgctgcagaggcccccagcccgagcccgcgcctgagcccat cctgcggccaccgctcatcagtctgaacccgctcttcccgcgg
```

An exemplary AVV9/P$_{ATP1A3}$-mCherry cDNA-rBGpA sequence (SEQ ID NO: 2).

ITR2-Patp1a3- *mCherry* rBGp(A) - ITR2
GCCACC = Kozak sequence
Cctgcaggcagctgcgcgctcgctcgctcactgaggccgcccgggca
aagcccgggcgtcgggcgacctttggtcgcccggcctcagtgagcga
gcgagcgcgcagagagggagtggccaactccatcactaggggttcct gcggccgcaCGCGT acatactgcaagatggtggcactctggggccctgcattactgcaattcactgggcctttcctcccacc
ctgtatctaccccactcccagaaggaggcagattccagggtgcctcaccctcaaagcctcggtcccta
agataccctcctatattgaggggggtctctgagtccccaccctggggatgtccgggatcaccccccc
ccccgcactgtgctcagcttctcagtggccgccactttgcagaaacaaggttggagcggtgaggggg
ggaaggggagtacagctgcagtactgggggccgggccgcaagctgtccgtctgctcagtactgctcc
tgattggccggagccgcctcccccgcgggcgcgggcatatgaggaggcggaggccccggccgccgcA
gcctctgtgcggtgggacccacggaccgacagacgcacgctcccaccgcggcgcgggcgctgcagagg
ccccagcccgagcccgcgcctgagcccatcctgcggccaccgctcatcagtctgaacgccgctcttc
ccgcgg ACCGGTGCCACCatggtgagcaagggcgaggaggataacatggccatcatcaaggagtt-
catgcgcttc
aaggtgcacatggagggctccgtgaacggc-
cacgagttcgagatcgagggcgagggcgagggccgcccc
tacgagggcacccagaccgccaagctgaaggtgac-
caagggtggccccctgcccttcgcctgggacatc
ctgtcccctcagttcatgtacggctccaaggcctacgtgaagcaccccgccga-
catccccgactacttg
aagctgtccttccccgagggcttcaagtgggagcgcgtgat-
gaacttcgaggacggcggcgtggtgacc
gtgacccaggactcctccctgcaggacggcgagttcatctacaaggt-
gaagctgcgcggcaccaacttc
ccctccgacggccccgtaatgcagaagaagaccatgggctgggaggcctcctccgagcg-
gatgtacccc
gaggacggcgcccctgaagggcgagatcaagcagaggctgaagctgaaggacggcggccac-
tacgctgag
gtcaagacccacctacaaggccaagaagcccgtgcagctgcccggcgcctacaacgtcaa-
catcaagttg
gacatcacctcccacaacgaggatcacaccatcgtg-
gaacagtacgaacgcgccgagggccgccactcc
accggcggcatggacgagctgtacaagtaaGTCGACCCGGGCGGCCTCGAGGACGGGGT-
GAACTACGCC
TGAGGATCCGATCTTTTTCCCTCTGCCAAAAATTATGGGGACATCATGAAGCCCCTTGAG-
CATCTGACT
TCTGGCTAATAAAGGAAATTTATTTTCATTGCAATAGTGTGTTGGAAT-
TTTTTGTGTCTCTCACTCGTc
cggacacgtgcggaccgagcggccgc aggaaccctagtgatggagttggccactccctctctgcgcgctcgctcgctcact-
gaggccgggcgac
caaaggtcgcccgacgcccgggctttgcccgggcggcctcagt-
gagcgagcgagcgcgcagctgcctgc
agg An exemplary P$_{ATP1A3}$-ATP1A3 cDNA-rBGpA sequence (SEQ ID NO: 3).

>Mmu-407 + 143 Atp1a3 Promoter = 550 bp total
>mATP$_1$A$_3$ cDNA in capital letters = 3042 bp
>rBG poly(A) signal = 131 bp
**acatactgcaagatggtggcactctggggccctgcattactgcaattcactgggcctttc
ctcccaccctgtatctaccccactcccagaaggaggcagattccagggtgcctcaccctc
aaagcctcggtccctaagataccctcctatattgaggggggtctctgagtccccaccct
ggggatgtccgggatcacccccccccccgcactgtgctcagcttctcagtggccgccac
tttgcagaaacaaggttggagcggtgagggggggaaggggagtacagctgcagtactgg
gggccgggccgcaagctgtccgtctgctcagtactgctcctgattggccggagccgcctc
ccccgcgggcgcgggcatatgaggaggcggaggccccggccgccgAgcctctgtgcgg
tgggacccacggaccgacagacgcacgctcccaccgcggcgcgggcgctgcagaggcccc
cagcccgagcccgcgcctgagcccatcctgcggccaccgctcatcagtctgaacgccgct
cttcccgcgg**_RE_*gccacc***ATGGGGGACAAAAAAGATGACAAGAGCTCGCC-
CAAGAAGAGCAAGGCCA
AAGAGCGCCGGGACCTGGATGACCTCAAGAAGGAAGTGGCTATGACAGAGCACAAGATGTCAGTAG
AAGAGGTCTGCCGGAAATACAATACTGACTGCGTGCAGGGTCTGACACACAGTAAAGCCCAGGAGA
TCCTAGCCCGGGATGGGCCTAACGCCCTCACACCACCGCCCACCACCCCAGAATGGGTCAAGTTCT
GCCGGCAGCTGTTTGGTGGCTTCTCTATCCTGCTGTGGATCGGGGCAATCCTTTGCTTCCTGGCCTA
TGGCATCCAGGCAGGGACGGAGGATGACCCTTCCGGTGACAATCTGTACCTGGGCATAGTGCTGGC
CGCAGTCGTGATCATCACCGGCTGCTTCTCCTACTACCAAGAAGCCAAGAGTTCTAAGATCATGGAG
TCCTTCAAGAACATGGTCCCCCAGCAAGCCCTTGTGATCCGGGAAGGTGAAAAGATGCAGGTGAAT
GCGGAGGAGGTGGTGGTCGGGGACCTGGTGGAGATCAAGGGTGGTGACCGGGTGCCAGCTGACC
TGCGCATCATCTCGGCCCATGGCTGCAAGGTGGACAACTCCTCCCTGACTGGCGAATCTGAGCCTC
AGACCCGCTCCCCGGACTGCACACACGACAACCCCCTGGAGACTCGGAACATCACCTTCTTTTCCA
CCAACTGCGTGGAAGGCACCGCTCGGGGTGTGGTGGTAGCCACAGGTGACCGCACCGTCATGGGC
CGCATTGCCACCCTGGCCTCGGGCTTGGAGGTGGGCAAGACGCCCATCGCCATTGAGATTGAGCAT
TTCATCCAGCTCATTACGGGCGTGGCCGTGTTCCTGGGCGTGTCCTTCTTCATCCTCTCTCTCATTCT

```
GGGTTACACCTGGCTCGAGGCAGTCATCTTCCTCATCGGCATCATTGTGGCCAATGTCCCAGAGGG
GCTGCTGGCTACTGTCACGGTGTGTCTGACGCTGACCGCCAAGCGCATGGCTCGCAAGAACTGCCT
GGTGAAGAACCTGGAGGCGGTGGAGACGCTGGGCTCCACGTCCACCATCTGCTCGGACAAGACCG
GCACTCTCACCCAGAACCGCATGACCGTCGCCCACATGTGGTTTGACAACCAGATCCACGAGGCAG
ACACCACAGAGGATCAGTCAGGGACCTCTTTCGACAAGAGCTCACACACCTGGGTGGCCCTGTCCC
ACATCGCCGGGCTCTGCAACCGGGCCGTCTTCAAGGGCGGGCAGGACAACATCCCAGTACTCAAG
AGGGACGTGGCCGGTGATGCCTCCGAGTCTGCCCTGCTTAAGTGCATTGAGCTGTCCTCGGGTTCC
GTAAAGCTGATGCGAGAACGGAACAAGAAAGTGGCTGAGATTCCGTTCAACTCGACCAACAAATACC
AGCTATCCATCCATGAGACTGAGGATCCCAATGACAACCGGTACCTGCTAGTGATGAAGGGCGCCC
CCGAACGCATTCTGGACCGCTGTGCCACCATCCTCCTGCAGGGCAAGGAGCAGCCTCTGGATGAG
GAGATGAAGGAGGCCTTCCAGAATGCCTACCTGGAGCTTGGTGGCCTGGGCGAGCGTGTGCTGGG
TTTCTGCCATTACTACCTGCCTGAGGAACAGTTCCCCAAGGGCTTTGCCTTTGACTGTGATGACGTG
AACTTCACCACAGACAACCTTTGCTTTGTGGGTCTCATGTCCATGATTGACCCTCCCCGGGCAGCCG
TCCCTGACGCTGTGGGCAAATGCCGAAGCGCAGGCATCAAGGTCATCATGGTCACCGGCGATCACC
CCATCACTGCCAAGGCCATTGCCAAGGGTGTGGGTATCATCTCTGAGGGTAACGAGACTGTCGAAG
ACATCGCTGCCCGGCTCAACATCCCTGTCAGCCAGGTGAACCCCAGGGATGCCAAAGCCTGTGTGA
TTCACGGCACCGACCTCAAGGACTTCACCTCGGAGCAGATTGACGAGATTCTGCAGAACCACACCG
AGATCGTCTTTGCCCGAACCTCCCCTCAGCAGAAGCTCATCATCGTGGAGGGCTGTCAGAGACAGG
GAGCAATTGTGGCTGTGACTGGCGATGGTGTGAATGACTCCCCTGCTCTGAAGAAGGCTGACATCG
GGGTGGCCATGGGCATTGCTGGCTCTGATGTCTCTAAGCAGGCTGCCGACATGATTCTGCTGGATG
ACAACTTTGCTTCCATTGTCACTGGTGTGGAGGAAGGCCGCCTGATCTTTGACAACCTGAAGAAATC
CATCGCCTACACTCTGACTAGCAACATCCCTGAGATCACACCCTTCCTGCTCTTCATCATGCTAACA
TCCCACTGCCTCTTGGCACCATCACCATCCTCTGCATTGACCTGGGTACCGACATGGTCCCTGCAAT
CTCCCTGGCCTACGAGGCTGCCGAGAGCGACATCATGAAGAGGCAGCCCAGGAACCCACGCACAG
ACAAACTGGTCAACGAAAGGCTCATCAGCATGGCCTACGGGCAGATTGGGATGATCCAGGCCCTCG
GTGGTTTCTTCTCCTACTTTGTCATCCTGGCAGAAAATGGCTTCTTGCCCGGAAACCTGGTGGGCAT
CCGGCTCAACTGGGATGATCGCACTGTCAATGACCTAGAAGACAGTTATGGGCAGCAGTGGACTTAT
GAGCAGAGGAAGGTGGTAGAGTTCACATGCCACACAGCCTTCTTTGTGAGTATCGTGGTGGTCCAG
TGGGCTGACCTGATCATCTGCAAGACCAGGAGGAACTCCGTCTTCCAGCAGGGCATGAAGAATAAG
ATCTTGATCTTCGGCTTGTTTGAGGAGACGGCCCTCGCTGCCTTCCTGTCCTACTGCCCAGGCATGG
ATGTGGCCCTTCGCATGTACCCTCTCAAGCCCAGCTGGTGGTTCTGTGCCTTCCCCTACAGTTTCCT
CATCTTCGTCTATGATGAGATTCGCAAACTCATCCTGCGCAGGAACCCCGGGGGTTGGGTGGAGAA
AGAGACCTACTATTGA RE gatcttttttccctctgccaaaaattatggggacatcatgaagcccct
tgagcatctgacttctggctaataaaggaaattattttcattgcaatagtgtgttggaattttt
tgtgtctctcactcggaag
```

An exemplary P<sub>CBh</sub>-ATP1A3 cDNA-rBGpA sequence (SEQ ID NO: 4).

```
>CBH promoter + Kozak sequence = 811 bp
>mATP1A3 cDNA in capital letters = 3042 bp
>rBG poly(A) signal = 131 bp
cgttacataaacttacggtaaatggcccgcctggctgaccgcccaacgacccccgcccattgacgtca
atagtaacgccaatagggactttccattgacgtcaatgggtggagtatttacggtaaactgcccact
tggcagtacatcaagtgtatcatatgccaagtacgccccctattgacgtcaatgacggtaaatggcc
cgcctggcattgtgcccagtacatgaccttatgggactttcctacttggcagtacatctacgtatta
gtcatcgctattaccatggtcgaggtgagccccacgttctgcttcactctccccatctcccccccct
cccaccccaattttgtatttatttattttttaattattttgtgcagcgatgggggcggggggggggg
gggggggcgcgcgccaggcggggcggggcggggcgagggcggggcggggcgagcggagaggtgcg
gcggcagccaatcagagcggcgcgctccgaaagtttccttttatggcgaggcggcggcggcggcggc
cctataaaaagcgaagcgcgcggcgggcgggagtcgctgcgacgctgccttcgccccgtgccccgct
ccgccgccgcctcgcgccgcccgccccggctctgactgaccgcgttactcccacaggtgagcgggcg
ggacggcccttctcctccgggctgtaattagctgagcaagaggtaagggtttaagggatggttggtt
ggtggggtattaatgtttaattacctggagcacctgcctgaaatcacttttttttcaggttggaccgg
t_RE_gccaccATGGGGGACAAAAAAGATGACAAGAGCTCGCCCAAGAAGAGCAAGGCCAAAGA
GCGCCGGGACCTGGATGACCTCAAGAAGGAAGTGGCTATGACAGAGCACAAGATGTCAGTAGAAGA
GGTCTGCCGGAAATACAATACTGACTGCGTGCAGGGTCTGACACACAGTAAAGCCCAGGAGATCCT
AGCCCGGGATGGGCCTAACGCCCTCACACCACCGCCCACCACCCCAGAATGGGTCAAGTTCTGCC
GGCAGCTGTTTGGTGGCTTCTCTATCCTGCTGTGGATCGGGGCAATCCTTTGCTTCCTGGCCTATGG
CATCCAGGCAGGGACGGAGGATGACCCTTCCGGTGACAATCTGTACCTGGGCATAGTGCTGGCCG
CAGTCGTGATCATCACCGGCTGCTTCTCCTACTACCAAGAAGCCAAGAGTTCTAAGATCATGGAGTC
CTTCAAGAACATGGTCCCCCAGCAAGCCCTTGTGATCCGGGAAGGTGAAAAGATGCAGGTGAATGC
GGAGGAGGTGGTGGTCGGGGACCTGGTGGAGATCAAGGGTGGTGACCGGGTGCCAGCTGACCTG
CGCATCATCTCGGCCCATGGCTGCAAGGTGGACAACTCCTCCCTGACTGGCGAATCTGAGCCTCAG
ACCCGCTCCCCGGACTGCACACACGACAACCCCCTGGAGACTCGGAACATCACCTTCTTTTCCACC
AACTGCGTGGAAGGCACCGCTCGGGGTGTGGTGGTAGCCACAGGTGACCGCACCGTCATGGGCCG
CATTGCCACCCTGGCCTCGGGCTTGGAGGTGGGCAAGACGCCCATCGCCATTGAGATTGAGCATTT
CATCCAGCTCATTACGGGCGTGGCCGTGTTCCTGGGCGTGTCCTTCTTCATCCTCTCTCTCATTCTG
GGTTACACCTGGCTCGAGGCAGTCATCTTCCTCATCGGCATCATTGTGGCCAATGTCCCAGAGGGG
CTGCTGGCTACTGTCACGGTGTGTCTGACGCTGACCGCCAAGCGCATGGCTCGCAAGAACTGCCTG
GTGAAGAACCTGGAGGCGGTGGAGACGCTGGGCTCCACGTCCACCATCTGCTCGGACAAGACCGG
CACTCTCACCCAGAACCGCATGACCGTCGCCCACATGTGGTTTGACAACCAGATCCACGAGGCAGA
CACCACAGAGGATCAGTCAGGGACCTCTTTCGACAAGAGCTCACACACCTGGGTGGCCCTGTCCCA
CATCGCCGGGCTCTGCAACCGGGCCGTCTTCAAGGGCGGGCAGGACAACATCCCAGTACTCAAGA
GGGACGTGGCCGGTGATGCCTCCGAGTCTGCCCTGCTTAAGTGCATTGAGCTGTCCTCGGGTTCCG
TAAAGCTGATGCGAGAACGGAACAAGAAAGTGGCTGAGATTCCGTTCAACTCGACCAACAAATACCA
GCTATCCATCCATGAGACTGAGGATCCCAATGACAACCGGTACCTGCTAGTGATGAAGGGCGCCCC
CGAACGCATTCTGGACCGCTGTGCCACCATCCTCCTGCAGGGCAAGGAGCAGCCTCTGGATGAGGA
GATGAAGGAGGCCTTCCAGAATGCCTACCTGGAGCTTGGTGGCCTGGGCGAGCGTGTGCTGGGTTT
CTGCCATTACTACCTGCCTGAGGAACAGTTCCCCAAGGGCTTTGCCTTTGACTGTGATGACGTGAAC
```

-continued

```
TTCACCACAGACAACCTTTGCTTTGTGGGTCTCATGTCCATGATTGACCCTCCCCGGGCAGCCGTCC
CTGACGCTGTGGGCAAATGCCGAAGCGCAGGCATCAAGGTCATCATGGTCACCGGCGATCACCCCA
TCACTGCCAAGGCCATTGCCAAGGGTGTGGGTATCATCTCTGAGGGTAACGAGACTGTCGAAGACA
TCGCTGCCCGGCTCAACATCCCTGTCAGCCAGGTGAACCCCAGGGATGCCAAAGCCTGTGTGATTC
ACGGCACCGACCTCAAGGACTTCACCTCGGAGCAGATTGACGAGATTCTGCAGAACCACACCGAGA
TCGTCTTTGCCCGAACCTCCCCTCAGCAGAAGCTCATCATCGTGGAGGGCTGTCAGAGACAGGGAG
CAATTGTGGCTGTGACTGGCGATGGTGTGAATGACTCCCCTGCTCTGAAGAAGGCTGACATCGGGG
TGGCCATGGGCATTGCTGGCTCTGATGTCTCTAAGCAGGCTGCCGACATGATTCTGCTGGATGACAA
CTTTGCTTCCATTGTCACTGGTGTGGAGGAAGGCCGCCTGATCTTTGACAACCTGAAGAAATCCATC
GCCTACACTCTGACTAGCAACATCCCTGAGATCACACCCTTCCTGCTCTTCATCATGGCTAACATCCC
ACTGCCTCTTGGCACCATCACCATCCTCTGCATTGACCTGGGTACCGACATGGTCCCTGCAATCTCC
CTGGCCTACGAGGCTGCCGAGAGCGACATCATGAAGAGGCAGCCCAGGAACCCACGCACAGACAA
ACTGGTCAACGAAAGGCTCATCAGCATGGCCTACGGGCAGATTGGGATGATCCAGGCCCTCGGTGG
TTTCTTCTCCTACTTTGTCATCCTGGCAGAAAATGGCTTCTTGCCCGGAAACCTGGTGGGCATCCGG
CTCAACTGGGATGATCGCACTGTCAATGACCTAGAAGACAGTTATGGGCAGCAGTGGACTTATGAGC
AGAGGAAGGTGGTAGAGTTCACATGCCACACAGCCTTCTTTGTGAGTATCGTGGTGGTCCAGTGGG
CTGACCTGATCATCTGCAAGACCAGGAGGAACTCCGTCTTCCAGCAGGGCATGAAGAATAAGATCTT
GATCTTCGGCTTGTTTGAGGAGACGGCCCTCGCTGCCTTCCTGTCCTACTGCCCAGGCATGGATGT
GGCCCTTCGCATGTACCCTCTCAAGCCCAGCTGGTGGTTCTGTGCCTTCCCCTACAGTTTCCTCATC
TTCGTCTATGATGAGATTCGCAAACTCATCCTGCGCAGGAACCCCGGGGGTTGGGTGGAGAAAGAG
ACCTACTATTGA_RE_gatcttttccctctgccaaaaattatggggacatcatgaagcccttgag
catctgacttctggctaataaaggaaatttattttcattgcaatagtgtgttggaattttttgtgtc
tctcactcggaag
```

An exemplary P$_{hSyn}$-ATP1A3 cDNA-rBGpA sequence (SEQ ID NO: 5).

```
>hSyn Promoter = 500 bp total (includes Kozak sequence)
>mATP₁A₃ cDNA in capital letters = 3042 bp
>rBG poly(A) signal = 131 bp
ttaattaaaactagacagactgcagagggccctgcgtatgagtgcaagtgggttt-
taggaccaggatgag
gcggggtggggtgcctacctgacgaccgaccccgacccactggacaagcacccaacccc-
cattcccca
aattgcgcatcccctatcagagagggggaggggaaacag-
gatgcggcgaggcgcgtcgcgactgccagc
ttcagcaccgcggacagtgccttcgcccccgcctggcggcgcgcgc-
caccgccgcctcagcactgaagg
cgcgctgacgtcactcgccggtccccgcaaactccccttcccggc-
caccttggtcgcgtccgcgccgc
cgccggcccagccggaccgcaccacgcgcgaggcgcgagatagggggggcacgggcgcgac-
catctgcgctg
cggcgccggcgactcagcgctgcctcagtctgcggtgggcagcggag-
gagtcgtgtcgtgcctgagagc
gcagtcgagag_RE_gccaccATGG
GGGACAAAAAAGATGACAAGAGCTCGCCCAAGAAGAGCAAGGCCAAAGAGCGCCGGGACCTGGAT
GACCTCAAGAAGGAAGTGGCTATGACAGAGCACAAGATGTCAGTAGAAGAGGTCTGCCGGAAATAC
AATACTGACTGCGTGCAGGGTCTGACACACAGTAAAGCCCAGGAGATCCTAGCCCGGGATGGGCCT
AACGCCCTCACACCACCGCCCACCACCCCAGAATGGGTCAAGTTCTGCCGGCAGCTGTTTGGTGGC
TTCTCTATCCTGCTCGTGGATCGGGCAATCCTTTGCTTCCTGGCCTATGGCATCCAGGCAGGGACG
GAGGATGACCCTTCCGGTGACAATCTGTACCTGGGCATAGTGCTGGCCGCAGTCGTGATCATCACC
GGCTGCTTCTCCTACTACCAAGAAGCCAAGAGTTCTAAGATCATGGAGTCCTTCAAGAACATGGTCC
CCCAGCAAGCCCTTGTGATCCGGGAAGGTGAAAAGATGCAGGTGAATGCGGAGGAGGTGGTGGTGA
GGGGACCTGGTGGAGATCAAGGGTGGTGACCGGGTGCCAGCTGACCTGCGCATCATCTCGGCCCA
TGGCTGCAAGGTGGACAACTCCTCCCTGACTGGCGAATCTGAGCCTCAGACCCGCTCCCCGACTG
CACACACGACAACCCCCTGGAGACTCGGAACATCACCTTCTTTTCCACCAACTGCGTGGAAGGCAC
CGCTCGGGGTGTGGTGGTAGCCACAGGTGACCGCACCGTCATGGGCCGCATTGCCACCCTGGCCT
CGGGCTTGGAGGTGGGCAAGACGCCCATCGCCATTGAGATTGAGCATTTCATCCAGTCATTACGG
GCGTGGCCGTGTTCCTGGGCGTGTCCTTCTTCATCCTCTCTCTCATTCTGGGTTACACCTGGCTCGA
GGCAGTCATCTTCCTCATCGGCATCATTGTGGCCAATGTCCCAGAGGGGCTGCTGGCTACTGTCAC
GGTGTGTCTGACGCTGACCGCCAAGCGCATGGCTCGCAAGAACTGCCTGGTGAAGAACCTGGAGG
CGGTGGAGACGCTGGGCTCCACGTCCACCATCTGCTCGGACAAGACCGGCACTCTCACCCAGAAC
CGCATGACCGTCGCCCACATGTGGTTTGACAACCAGATCCACGAGGCAGACACCACAGAGGATCAG
TCAGGGACCTCTTTCGACAAGAGCTCACACACCTGGGTGGCCCTGTCCCACATCGCCGGGCTCTGC
AACCGGGCCGTCTTCAAGGGCGGGCAGGACAACATCCCAGTACTCAAGAGGGACGTGGCCGGTGA
TGCCTCCGAGTCTGCCCTGCTTAAGTGCATTGAGCTGTCCTCGGGTTCCGTAAAGCTGATGCGAGAA
CGGAACAAGAAAGTGGCTGAGATTCCGTTCAACTCGACCAACAAATACCAGCTATCCATCCATGAGA
CTGAGGATCCCAATGACAACCGGTACCTGCTAGTGATGAAGGGCGCCCCCGAACGCATTCTGGACC
GCTGTGCCACCATCCTCCTGCAGGGCAAGGAGCAGCCTCTGGATGAGGAGATGAAGGAGGCCTTC
CAGAATGCCTACCTGGAGCTTGGTGGCCTGGGCGAGCGTGTGCTGGGTTTCTGCCATTACTACCTG
CCTGAGGAACAGTTCCCCAAGGGCTTTGCCTTTGACTGTGATGACGTGAACTTCACCACAGACAACC
TTTGCTTTGTGGGTCTCATGTCCATGATTGACCCTCCCCGGGCAGCCGTCCCTGACGCTGTGGGCA
AATGCCGAAGCGCAGGCATCAAGGTCATCATGGTCACCGGCGATCACCCCATCACTGCCAAGGCCA
TTGCCAAGGGTGTGGGTATCATCTCTGAGGGTAACGAGACTGTCGAAGACATCGCTGCCCGGCTCA
ACATCCCTGTCAGCCAGGTGAACCCCAGGGATGCCAAAGCCTGTGTGATTCACGGCACCGACCTCA
AGGACTTCACCTCGGAGCAGATTGACGAGATTCTGCAGAACCACACCGAGATCGTCTTTGCCCGAA
CCTCCCCTCAGCAGAAGCTCATCATCGTGGAGGGCTGTCAGAGACAGGGCAATTGTGGCTGTGA
CTGGCGATGGTGTGAATGACTCCCCTGCTCTGAAGAAGGCTGACATCGGGGTGGCCATGGGCATTG
CTGGCTCTGATGTCTCTAAGCAGGCTGCCGACATGATTCTGCTGGATGACAACTTTGCTTCCATTGT
CACTGGTGTGGAGGAAGGCCGCCTGATCTTTGACAACCTGAAGAAATCCATCGCCTACACTCTGACT
AGCAACATCCCTGAGATCACACCCTTCCTGCTCTTCATCATGGCTAACATCCCACTGCCTCTTGGCA
CCATCACCATCCTCTGCATTGACCTGGGTACCGACATGGTCCCTGCAATCTCCCTGGCCTACGAGG
```

```
CTGCCGAGAGCGACATCATGAAGAGGCAGCCCAGGAACCCACGCACAGACAAACTGGTCAACGAAA
GGCTCATCAGCATGGCCTACGGGCAGATTGGGATGATCCAGGCCCTCGGTGGTTTCTTCTCCTACTT
TGTCATCCTGGCAGAAAATGGCTTCTTGCCCGGAAACCTGGTGGGCATCCGGCTCAACTGGGATGA
TCGCACTGTCAATGACCTAGAAGACAGTTATGGGCAGCAGTGGACTTATGAGCAGAGGAAGGTGGT
AGAGTTCACATGCCACACAGCCTTCTTTGTGAGTATCGTGGTGGTCCAGTGGGCTGACCTGATCATC
TGCAAGACCAGGAGGAACTCCGTCTTCCAGCAGGGCATGAAGAATAAGATCTTGATCTTCGGCTTGT
TTGAGGAGACGGCCCTCGCTGCCTTCCTGTCCTACTGCCCAGGCATGGATGTGGCCCTTCGCATGT
ACCCTCTCAAGCCCAGCTGGTGGTTCTGTGCCTTCCCCTACAGTTTCCTCATCTTCGTCTATGATGA
GATTCGCAAACTCATCCTGCGCAGGAACCCCGGGGGTTGGGTGGAGAAAGAGACCTACTATTGA
RE gatcttttccctctgccaaaaattatggggacatcatgaagcccccttgagcatctgacttc
tggctaataaaggaaatttatttttcattgcaatagtgtgttggaattttttgtgtctctcac
tcggaag
```

In the above three sequences, the promoter sequence is indicated in lower case letters and marked in boldface. This part of the cassette drives transcription of the transgene and defines the cellular specificity of its expression. In the first sequence, mouse promoter Patp1a3 was used, and may be replaced with the corresponding homologous human sequence for human application, the mouse promoter.

Ribosome binding site (=upstream regulatory bit) is indicated in lower case letters and marked in red, and is separated from the promoter sequence by "RE".

3'UTR and poly(A) signal (=downstream regulatory bit) is indicated in lower case letters and marked in green, and is separated from the ATP1A3 protein-coding sequence by "RE".

The ATP1A3 protein-coding sequence is the same in all three sequences, indicated in capital letters, and is represented by the open reading frame (ORF) of the most predominant transcript of mouse ATP1A3 gene.

For human application, this mouse ATP1A3 protein-coding sequence may be replaced with ORF of the corresponding human sequence, which is also the predominant transcript of human ATP1A3 gene. This human ORF sequence is below (SEQ ID NO: 6).

```
>Hsa_ATP1A3_isoform_1_NM_152296.4
ATGGGGGACAAGAAAGATGACAAGGACTCACCCAAGAAGAACAAGGGCAA
GGAGCGCCGGGACCTGGATGACCTCAAGAAGGAGGTGGCTATGACAGAGC
ACAAGATGTCAGTGGAAGAGGTCTGCCGGAAATACAACACAGACTGTGTG
CAGGGTTTGACCCACAGCAAAGCCCAGGAGATCCTGGCCCGGGATGGGCC
TAACGCACTCACGCCACCGCCTACCACCCCAGAGTGGGTCAAGTTTTGCC
GGCAGCTCTTCGGGGGCTTCTCCATCCTGCTGTGGATCGGGGCTATCCTC
TGCTTCCTGGCCTACGGTATCCAGGCGGGCACCGAGGACGACCCCTCTGG
TGACAACCTGTACCTGGGCATCGTGCTGGCGGCCGTGGTGATCATCACTG
GCTGCTTCTCCTACTACCAGGAGGCCAAGAGCTCCAAGATCATGGAGTCC
TTCAAGAACATGGTGCCCCAGCAAGCCCTGGTGATCCGGGAAGGTGAGAA
GATGCAGGTGAACGCTGAGGAGGTGGTGGTCGGGGACCTGGTGGAGATCA
AGGGTGGAGACCGAGTGCCAGCTGACCTGCGGATCATCTCAGCCCACGGC
TGCAAGGTGGACAACTCCTCCCTGACTGGCGAATCCGAGCCCCAGACTCG
CTCTCCCGACTGCACTCACGACAACCCCTTGGAGACTCGGAACATCACCT
TCTTTTCCACCAACTGTGTGGAAGGCACGGCTCGGGGCGTGGTGGTGGCC
ACGGGCGACCGCACTGTCATGGGCCGTATCGCCACCCTGGCATCAGGGCT
GGAGGTGGGCAAGACGCCCCATCGCCATCGAGATTGAGCACTTCATCCAGC
TCATCACCGGCGTGGCTGTCTTCCTGGGTGTCTCCTTCTTCATCCTCTCC
CTCATTCTCGGATACACCTGGCTTGAGGCTGTCATCTTCCTCATCGGCAT
CATCGTGGCCAATGTCCCAGAGGGTCTGCTGGCCACTGTCACTGTGTGTC
TGACGCTGACCGCCAAGCGCATGGCCCGGAAGAACTGCCTGGTGAAGAAC
CTGGAGGCTGTAGAAACCCTGGGCTCCACGTCCACCATCTGCTCAGATAA
GACAGGGACCCTCACTCAGAACCGCATGACAGTCGCCCACATGTGGTTTG
ACAACCAGATCCACGAGGCTGACACCACTGAGGACCAGTCAGGGACCTCA
TTTGACAAGAGTTCGCACACCTGGGTGGCCCTGTCTCACATCGCTGGGCT
CTGCAATCGCGCTGTCTTCAAGGGTGGTCAGGACAACATCCCTGTGCTCA
AGAGGGATGTGGCTGGGGATGCGTCTGAGTCTGCCCTGCTCAAGTGCATC
GAGCTGTCCTCTGGCTCCGTGAAGCTGATGCGTGAACGCAACAAGAAAGT
GGCTGAGATTCCCTTCAATTCCACCAACAAATACCAGCTCTCCATCCATG
AGACCGAGGACCCCAACGACAACCGATACCTGCTGGTGATGAAGGGTGCC
CCCGAGCGCATCCTGGACCGCTGCTCCACCATCCTGCTACAGGGCAAGGA
GCAGCCTCTGGACGAGGAAATGAAGGAGGCCTTCCAGAATGCCTACCTTG
AGCTCGGTGGCCTGGGCGAGCGCGTGCTTGGTTTCTGCCATTATTACCTG
CCCGAGGAGCAGTTCCCCAAGGGCTTTGCCTTCGACTGTGATGACGTGAA
CTTCACCACGGACAACCTCTGCTTTGTGGGCCTCATGTCCATGATCGACC
CACCCCGGGCAGCCGTCCCTGACGCGGTGGGCAAGTGTCGCAGCGCAGGC
ATCAAGGTCATCATGGTCACCGGCGATCACCCCATCACGGCCAAGGCCAT
TGCCAAGGGTGTGGGCATCATCTCTGAGGGCAACGAGACTGTGGAGGACA
TCGCCGCCCGGCTCAACATTCCCGTCAGCCAGGTTAACCCCCGGGATGCC
AAGGCCTGCGTGATCCACGGCACCGACCTCAAGGACTTCACCTCCGAGCA
AATCGACGAGATCCTGCAGAATCACACCGAGATCGTCTTCGCCCGCACAT
CCCCCCAGCAGAAGCTCATCATTGTGGAGGGCTGTCAGAGACAGGGTGCA
ATTGTGGCTGTGACCGGGGATGGTGTGAACGACTCCCCCGCTCTGAAGAA
GGCCGACATTGGGGTGGCCATGGGCATCGCTGGCTCTGACGTCTCCAAGC
AGGCAGCTGACATGATCCTGCTGGACGACAACTTTGCCTCCATCGTCACA
```

-continued
```
GGGGTGGAGGAGGGCCGCCTGATCTTCGACAACCTAAAGAAGTCCATTGC

CTACACCCTGACCAGCAATATCCCGGAGATCACGCCCTTCCTGCTGTTCA

TCATGGCCAACATCCCGCTGCCCTGGGCACCATCACCATCCTCTGCATC

GATCTGGGCACTGACATGGTCCCTGCCATCTCACTGGCGTACGAGGCTGC

CGAAAGCGACATCATGAAGAGACAGCCCAGGAACCCGCGGACGGACAAAT

TGGTCAATGAGAGACTCATCAGCATGGCCTACGGGCAGATTGGAATGATC

CAGGCTCTCGGTGGCTTCTTCTCTTACTTTGTGATCCTGGCAGAAAATGG

CTTCTTGCCCGGCAACCTGGTGGGCATCCGGCTGAACTGGGATGACCGCA

CCGTCAATGACCTGGAAGACAGTTACGGGCAGCAGTGGACATACGAGCAG

AGGAAGGTGGTGGAGTTCACCTGCCACACGGCCTTCTTTGTGAGCATCGT

TGTCGTCCAGTGGGCCGATCTGATCATCTGCAAGACCCGGAGGAACTCGG

TCTTCCAGCAGGGCATGAAGAACAAGATCCTGATCTTCGGGCTGTTTGAG

GAGACGGCCCTGGCTGCCTTCCTGTCCTACTGCCCCGGCATGGACGTGGC

CCTGCGCATGTACCCTCTCAAGCCCAGCTGGTGGTTCTGTGCCTTCCCCT

ACAGTTTCCTCATCTTCGTCTACGACGAAATCCGCAAACTCATCCTGCGC

AGGAACCCAGGGGGTTGGGTGGAGAAGGAAACCTACTACTGA
```

Example 1

Experiments Using Wild Type Mice/Neuron Culture

Several mouse models of AHC are available for gene therapy testing in vivo. Six distinct mouse strains carrying common AHC-associated ATP1A3 alleles have been generated and characterized. These mouse models phenocopy many clinical symptoms of AHC, demonstrating causality and reproducing the disease severity spectrum observed in AHC patients. These strains thus provide multiple, available, and independent experimental substrates to test the effectiveness of proposed gene delivery in vivo.

D801N/+ mice were generated via CRISPR-based genomic editing. When introduced into mice, the D801N allele (GAC4AAC) also contains the PAM-blocking silent L8202L mutation (CTG→CTA).

I810N/+ frozen embryos were provided by the strain creator, Dr. Steven Clapcote.

To determine vector feasibility, mouse primary cerebellar (Purkinje cell) culture is transfected with AAV vector carrying 500pb mouse ATP1A3 promoter and 3 kb cDNA.

Controls include un-transfected neuron culture, mock transfected neuron culture, and neuron culture transfected with AAV with ATP1A3 promoter-driven GFP.

Levels of ATP1A3 expression are quantified in each using RT-PCR and Western of lysates.

Example 1A

Determining Whether Delivery of Wild Type ATP1A3 Gene via CSF is Sufficient to Rescue Mouse ATP 1 A3 KO model of AHC Inject available KO AHC mice models (DeAndrade, or Ikeda a3+/AE2-6 mice, or Lingrel a3+/KOI4 mice) with ATP1A3 carrying AAV vector. Neonates, 2 week old, and 2 month old mice are tested.

Negative control comprises injection of AHC mice with empty AAV vector.

Positive control comprises injection of wild type mice at same age, with same vector.

Test to measure rescue (Rely on specific known expertise in characterizing the mouse)

Follow-up tests: Harvest brains, check ATP1a3 protein and mRNA levels using immunohistochemistry and/or antisense oligo in target brain areas: cerebellum, DCN, brain stem, PV+ interneurons, hippocampus, basal ganglia, thalamus, corpus callosum, and motor cortex.

TABLE 1

Comparison of clinical features in alternating hemiplegia of childhood and ATP1A3 mouse models

| Symptoms | Clinical disorder AHC | Mouse models with ATP1A3 missense mutations | | | |
|---|---|---|---|---|---|
| | | Mashlool D801N/+ | Myshkin I810N/+ | Matoub E815K/+ | D801Y/+ |
| Hemiplegic episodes | + | + | * | + | − |
| Dystonia | + | + | * | + | + |
| Abnormal motor control/ataxia | + | + | + | + | + |
| Spontaneous seizures | + | + | + | + | − |
| SUDEP | + | + | + | + | |
| Learning and memory impairments | + | + | + | + | + |
| Impulsivity/Increased activity in open field | + | + | + | − | + |
| Abnormal eye movements | + | − | − | − | − |

+, feature usually occurs;
−, feature not described
* Limb clasping, hindlimb splaying and hindlimb dragging

Example 1B

Determining Whether Delivery of Wild Type ATP1A3 Gene to CSF is Sufficient to Rescue Mouse ATP1A3 Missense Model of AHC Inject available missense AHC mouse models (D801N, D801Y, I810N and E815K) at site determined in (1) above with ATP1A3 carrying AAV vector. Neonates, 2 week old, and 2 month old mice are tested. The test for rescue is as described for KO mice above.

Example 2

This example compares specificity and strength of ATP1A3 transgene expression driven by three different AAV9 vectors in mouse brains (AAV vector constructs differ only in their promoter configuration, all the rest of the coding and regulatory DNA sequences are identical among them).

Vector biodistribution and expression specificity was determined by double labeling with antibodies against mouse ATP1A3 protein with specific neuronal markers such as Calbindin for Purkinje neurons and GAD67 for GABAergic neurons.

The first steps consisted of determining the best antibodies and staining conditions to detect ATP1A3 in mouse brain tissues, and in neuronal subtypes: Purkinje cells in the cerebellum and GABAergic neurons in cortex, hippocampus and basal ganglia.

1. Experimental Model

Wild type mouse brain embedded in paraffin, sliced at the level of dorsal hippocampus and in the cerebellum.

Mice injected with mCherry and ATP1A3 expressing AAV viruses, as shown in Table 1, below.

1. 8 brains (4m/4f) injected with AAV9_$P_{ATP1A3}$::mCherry
2. 8 brains (4m/4f) injected with AAV9_$P_{ATP1A3}$::ATP1A3
3. 8 brains (4m/4f) injected with AAV9_$P_{synapsin}$::ATP1A3
4. 8 brains (4m/4f) injected with AAV9_$P_{CBh::ATP}$1A3

TABLE 1

| Animal # | Sex | DOB | Treatment Group | Date Injection |
|---|---|---|---|---|
| 1-1 | F | 30 Oct. 2018 | AAV9_PATP1A3::mCherry | 26 Nov. 2018 |
| 1-2 | F | 30 Oct. 2018 | AAV9_PATP1A3::mCherry | 26 Nov. 2018 |
| 1-3 | F | 30 Oct. 2018 | AAV9_PATP1A3::mCherry | 27 Nov. 2018 |
| 1-4 | F | 30 Oct. 2018 | AAV9_PATP1A3::mCherry | 27 Nov. 2018 |
| 1-5 | M | 30 Oct. 2018 | AAV9_PATP1A3::mCherry | 29 Nov. 2019 |
| 1-6 | M | 30 Oct. 2018 | AAV9_PATP1A3::mCherry | 29 Nov. 2019 |
| 1-7 | M | 30 Oct. 2018 | AAV9_PATP1A3::mCherry | 30 Nov. 2018 |
| 1-8 | M | 30 Oct. 2018 | AAV9_PATP1A3::mCherry | 30 Nov. 2018 |
| 2-1 | F | 30 Oct. 2018 | AAV9_PATP1A3::ATP1A3 | 26 Nov. 2018 |
| 2-2 | F | 30 Oct. 2018 | AAV9_PATP1A3::ATP1A3 | 26 Nov. 2018 |
| 2-3 | F | 30 Oct. 2018 | AAV9_PATP1A3::ATP1A3 | 27 Nov. 2018 |
| 2-4 | F | 30 Oct. 2018 | AAV9_PATP1A3::ATP1A3 | 27 Nov. 2018 |
| 2-5 | M | 30 Oct. 2018 | AAV9_PATP1A3::ATP1A3 | 29 Nov. 2019 |
| 2-6 | M | 30 Oct. 2018 | AAV9_PATP1A3::ATP1A3 | 29 Nov. 2019 |
| 2-7 | M | 30 Oct. 2018 | AAV9_PATP1A3::ATP1A3 | 30 Nov. 2018 |
| 2-8 | M | 30 Oct. 2018 | AAV9_PATP1A3::ATP1A3 | 30 Nov. 2018 |
| 3-1 | F | 30 Oct. 2018 | AAV9_PSyn::ATP1A3 | 26 Nov. 2018 |
| 3-2 | F | 30 Oct. 2018 | AAV9_PSyn::ATP1A3 | 26 Nov. 2018 |
| 3-3 | F | 30 Oct. 2018 | AAV9_PSyn::ATP1A3 | 27 Nov. 2018 |
| 3-4 | F | 30 Oct. 2018 | AAV9_PSyn::ATP1A3 | 27 Nov. 2018 |
| 3-5 | M | 30 Oct. 2018 | AAV9_PSyn::ATP1A3 | 29 Nov. 2019 |
| 3-6 | M | 30 Oct. 2018 | AAV9_PSyn::ATP1A3 | 29 Nov. 2019 |
| 3-7 | M | 30 Oct. 2018 | AAV9_PSyn::ATP1A3 | 30 Nov. 2018 |
| 3-8 | M | 30 Oct. 2018 | AAV9_PSyn::ATP1A3 | 30 Nov. 2018 |
| 4-1 | F | 30 Oct. 2018 | AAV9_PCBh::ATP1A3 | 26 Nov. 2018 |
| 4-2 | F | 30 Oct. 2018 | AAV9_PCBh::ATP1A3 | 26 Nov. 2018 |
| 4-3 | F | 30 Oct. 2018 | AAV9_PCBh::ATP1A3 | 27 Nov. 2018 |
| 4-4 | F | 30 Oct. 2018 | AAV9_PCBh::ATP1A3 | 27 Nov. 2018 |
| 4-5 | M | 30 Oct. 2018 | AAV9_PCBh::ATP1A3 | 29 Nov. 2019 |
| 4-6 | M | 30 Oct. 2018 | AAV9_PCBh::ATP1A3 | 29 Nov. 2019 |
| 4-7 | M | 30 Oct. 2018 | AAV9_PCBh::ATP1A3 | 30 Nov. 2018 |
| 4-8 | M | 30 Oct. 2018 | AAV9_PCBh::ATP1A3 | 30 Nov. 2018 |

2. Experimental Procedure and Treatment Schedule

Brains received by Novaxia were pre-sliced to isolate the cerebellum, which was dehydrated and included in paraffin blocks. 4μm slices were obtained from each cerebellum and put on glass slides.

Fluofarma performed labelings, starting with multiple test conditions of multiple antibodies:

Three ATP1A3 antibodies were tested, all from Rabbits:
Sigma/Atlas antibody reference #HPA056446 at 1:1000
EMD Millipore antibody reference #06-172-1 at 1:250
ProteinTech antibody reference #10868-1-AP at 1:100

One Calbindin antibody was tested (from chicken):
Synaptic Systems reference #214006 at 1:200

Three GAD67 antibodies were tested:
Novusbio #NBP1-02161 at 1:1000 and 1:300
Synaptic Systems #198 006 at 1:200
Millipore #MAB5406 at 1:500

One mCherry antibody was tested (from rat):
Molecular Probes #M11217 at 1:200

ATP1A3 antibodies were tested on hippocampal and cerebellum slices. The calbindin antibody was tested on cerebellum slices and the GAD67 antibody was tested on hippocampal slices.

For each antibody, standard immunofluorescence protocols were performed using a Ventana XT automated platform, with two standard antigen retrieval procedures, at pH 6 or pH 8 to determine the best antigen retrieval condition.

For ATP1A3, a secondary anti-rabbit Alexa 488 antibody was used for detection while for Calbindin and GAD67 and anti-chicken Alexa 594 antibody was used (Invitrogen, 1:400 dilution).

For mCherry detection, as mCherry is a red fluorescent protein, an Alexa 594 anti-rat antibody was chosen for mCherry (1:400 dilution).

Additional slides were labeled without the presence of primary antibody to control for potential background/aspecific stainings.

For labeling mouse cerebella which were injected with AAV viruses, antigen retrieval was performed at pH8 for all antibodies, and slides were labeled with the anti-mCherry antibody (Molecular Probes #M11217) at 1:200 +anti-Calbindin antibody (Synaptic Systems #214006) at 1:200, and anti-ATP1A3 antibody (EMD Millipore antibody #06-172-1) at 1:250 +anti-Calbindin antibody (Synaptic Systems #214006) at 1:200.

Secondary antibodies were Goat anti-rat Alexa 594 (Invitrogen #A11007) +Goat anti-Chicken Alexa 488 (Invitrogen #A11039) for mCherry/Calbindin and Goat anti-rabbit Alexa 488 (Invitrogen #A11008) +Goat anti-Chicken Alexa 594 (Invitrogen #A11042) for ATP1A3/Calbindin, all at 1:400 dilution.

One slice per animal was stained.

3. Results for Staining Development

Staining involved the following categories of antibodies: ATP1A3 antibodies, Calbindin antibodies, GAD67 antibodies, and mCherry antibodies.

ATP1A3 Antibody: Millipore #06-172-1

FIG. 1 depicts ATP1A3 (Millipore #06-172-1) staining in a mouse cerebellum. This ATP1A3 elicitates a good specific signal compared to the signal obtained in the absence of primary antibody, at both antigen retrieval pH. However, a higher signal was obtained with antigen retrieval at pH8. All images were acquired with the same microscope settings (exposure time, image dynamic range).

Figure 2:
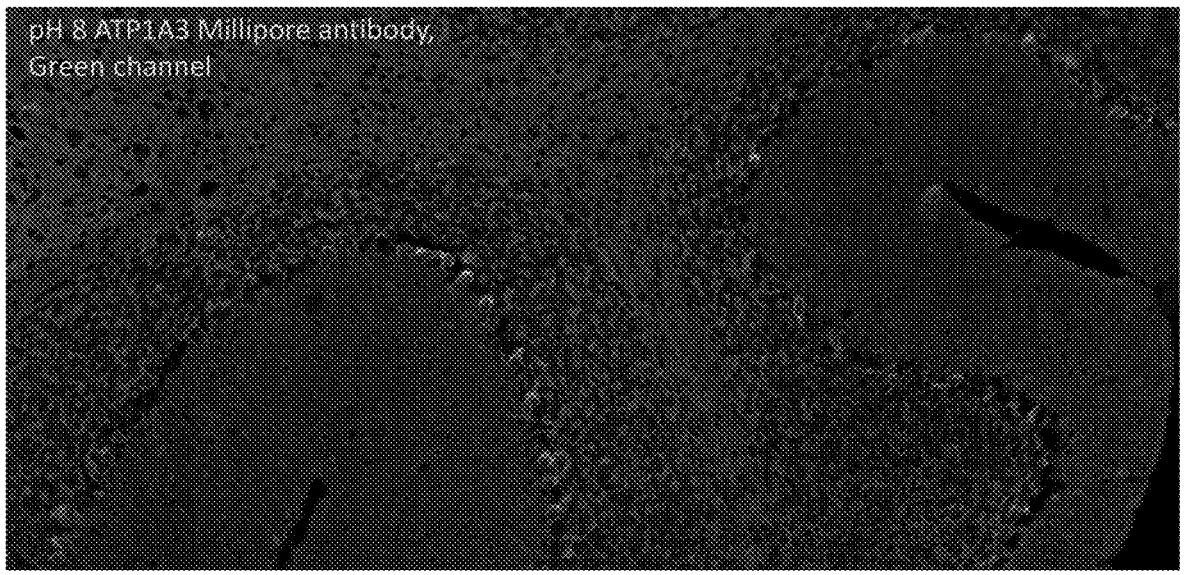
FIG. 2 depicts ATP1A3 (Millipore #06-172-1) staining in a mouse cerebellum, as a zoomed image.

FIG. 2 depicts ATP1A3 (Millipore #06-172-1) staining in mouse cerebellum. The zoomed image shows the ATP1A3 signal (green fluorescence channel) in the best condition, showing the widespread labeling and higher labeling fluorescence in what appears to be Purkinje cells.

Figure 3:
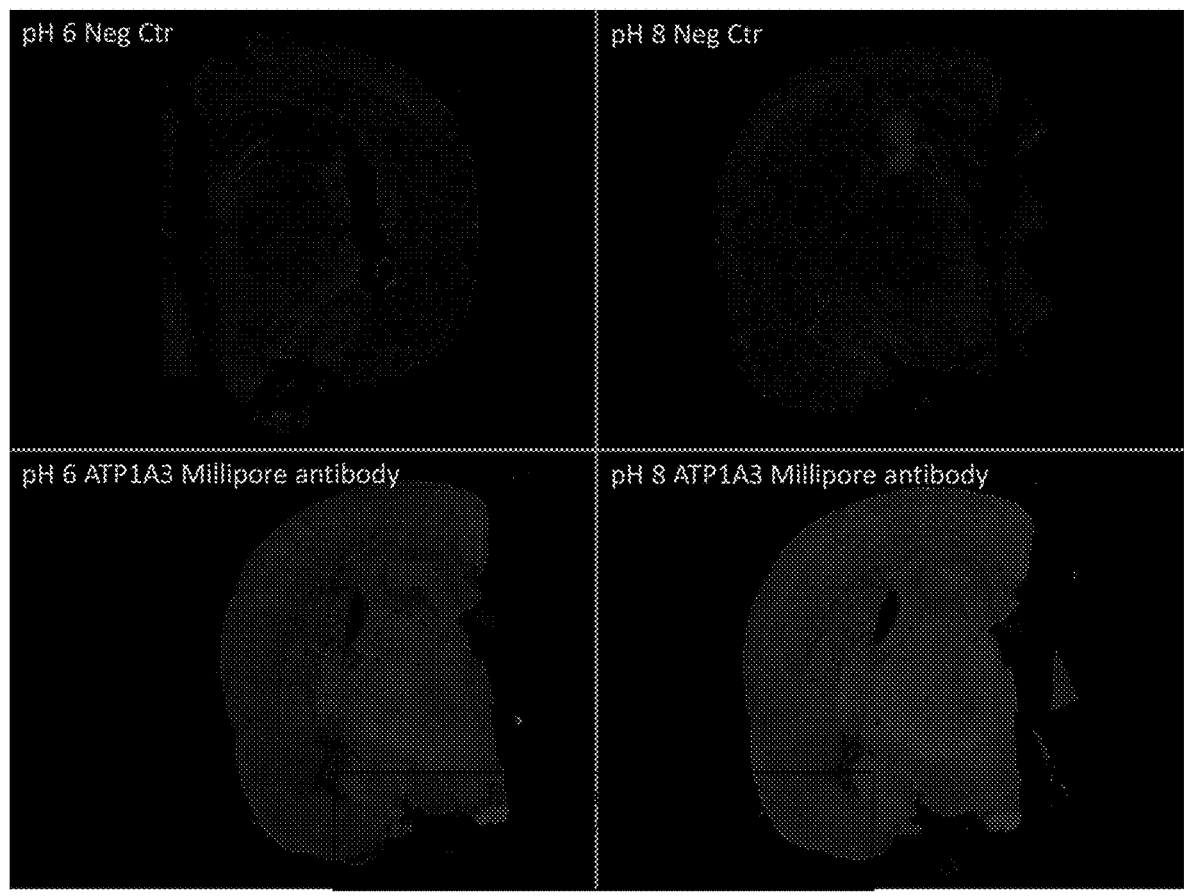
FIG. 3 depicts ATP1A3 (Millipore #06-172-1) staining in a mouse brain at dorsal hippocampus level. All images were acquired with the same microscope settings (exposure time, image dynamic range).

FIG. 3 depicts ATP1A3 (Millipore #06-172-1) staining in mouse brain at dorsal hippocampus level. This ATP1A3 antibody elicitates a good specific signal compared to the signal obtained in the absence of primary antibody, at both antigen retrieval pH. However, a higher signal was obtained with antigen retrieval at pH8. All images were acquired with the same microscope settings (exposure time, image dynamic range).

Figure 4:
FIG. 4 depicts ATP1A3 (Millipore #06-172-1) staining in a mouse brain at dorsal hippocampus level, as a zoomed image.

FIG. 4 depicts ATP1A3 (Millipore #06-172-1) staining in mouse brain at dorsal hippocampus level. The zoomed image shows the ATP1A3 signal (green fluorescence channel) in the best condition, showing the widespread labeling. Some cells appear to have higher perinuclear signals in the parietal cortex and in the hippocampus in CA1, CA2-3 and Dentate Gyms.

Figure 5:
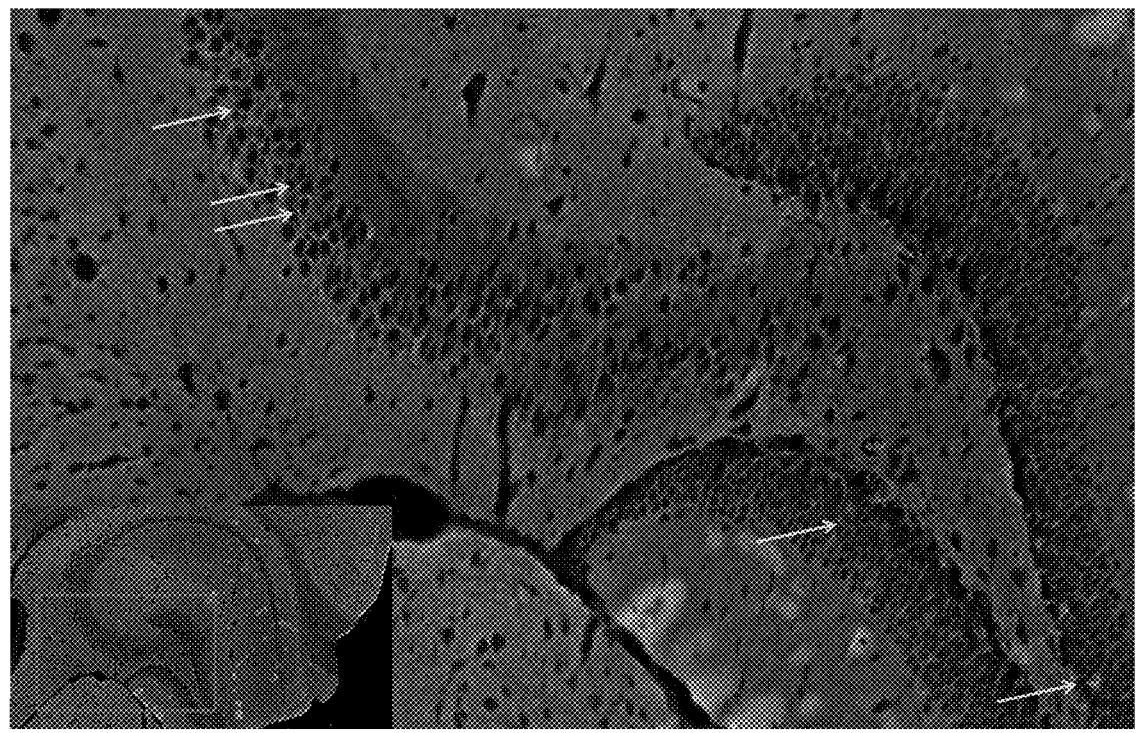
FIG. 5 depicts ATP1A3 (Millipore #06-172-1) staining in the dorsal hippocampus, as zoomed image.

FIG. 5 shows the ATP1A3 (Millipore #06-172-1) staining in the dorsal hippocampus. The zoomed image shows the ATP1A3 signal (green fluorescence channel) in the best condition (pH8 antigen retrieval) in the dorsal hippocampus. Arrows show cells with higher labeling.

Figure 6:
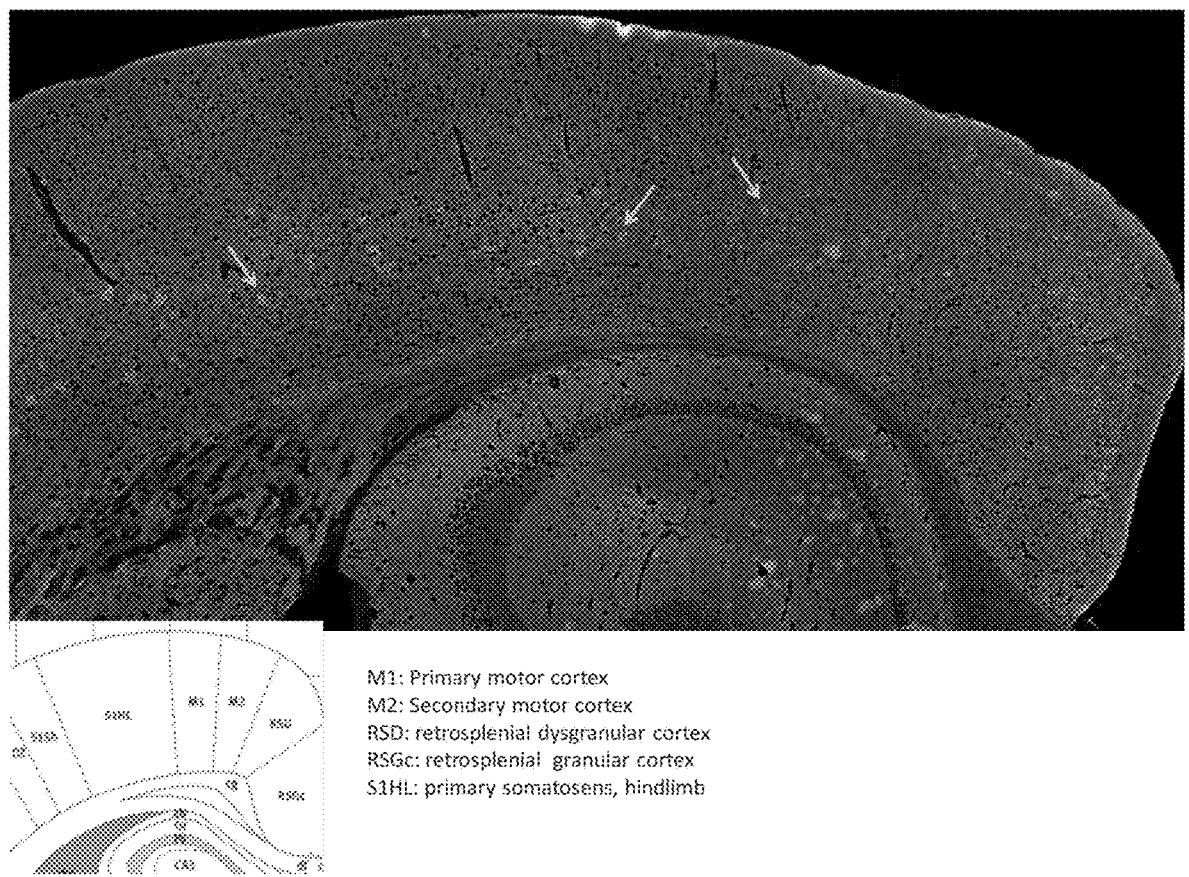
FIG. 6 depicts ATP1A3 (Millipore #06-172-1) staining in the parietal cortex, as a zoomed image.

FIG. 6 shows the ATP1A3 (Millipore #06-172-1) staining in the parietal cortex. The zoomed image shows the ATP1A3 signal (green fluorescence channel) in the best condition (pH8 antigen retrieval), in the parietal cortex. Arrows show examples of cells with higher labeling.

Calbindin Antibody: Synaptic Systems #214006

Figure 7:
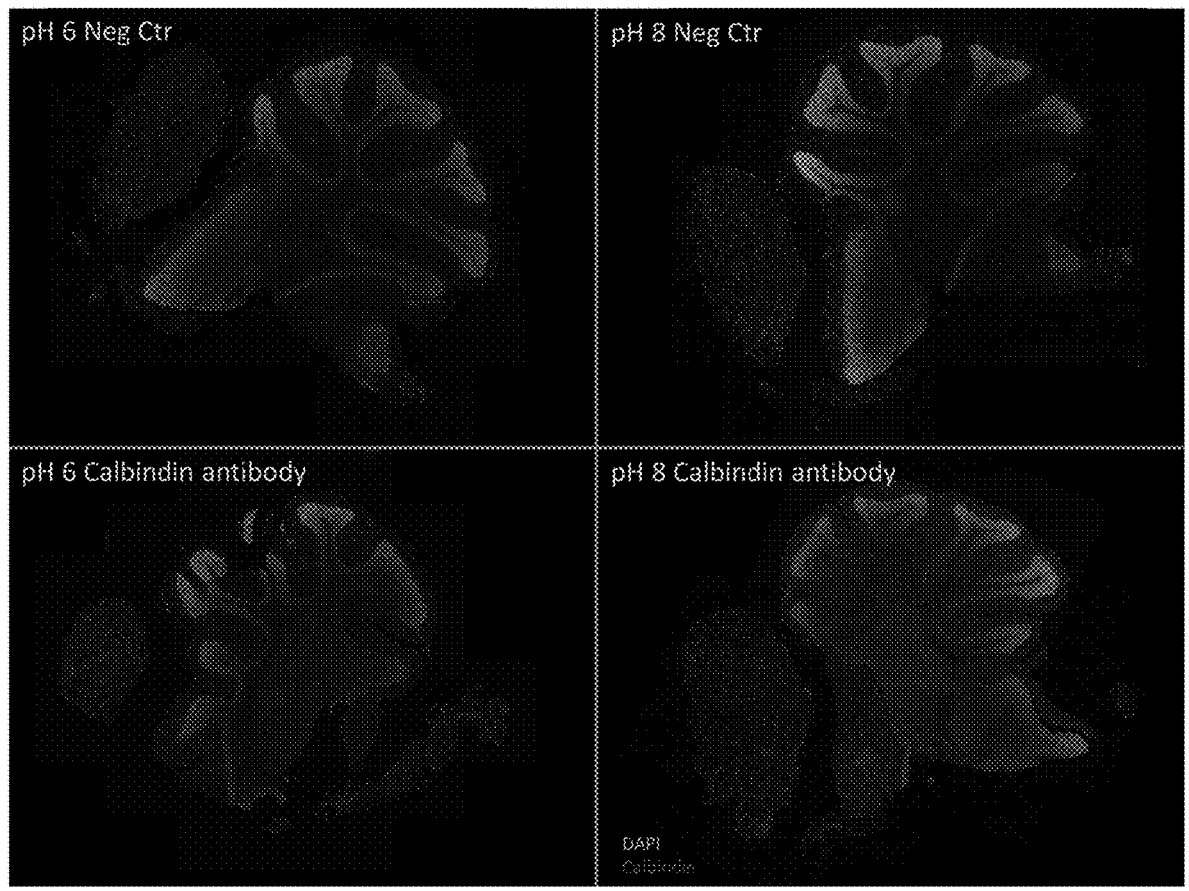
FIG. 7 depicts Calbindin (Synaptic Systems #214006) staining in a mouse cerebellum.

FIG. 7 depicts Calbindin (Synaptic Systems #214006) staining in mouse cerebellum. This antibody elicited the best specific signal over the negative control in the pH8 antigen retrieval condition.

Figure 8:
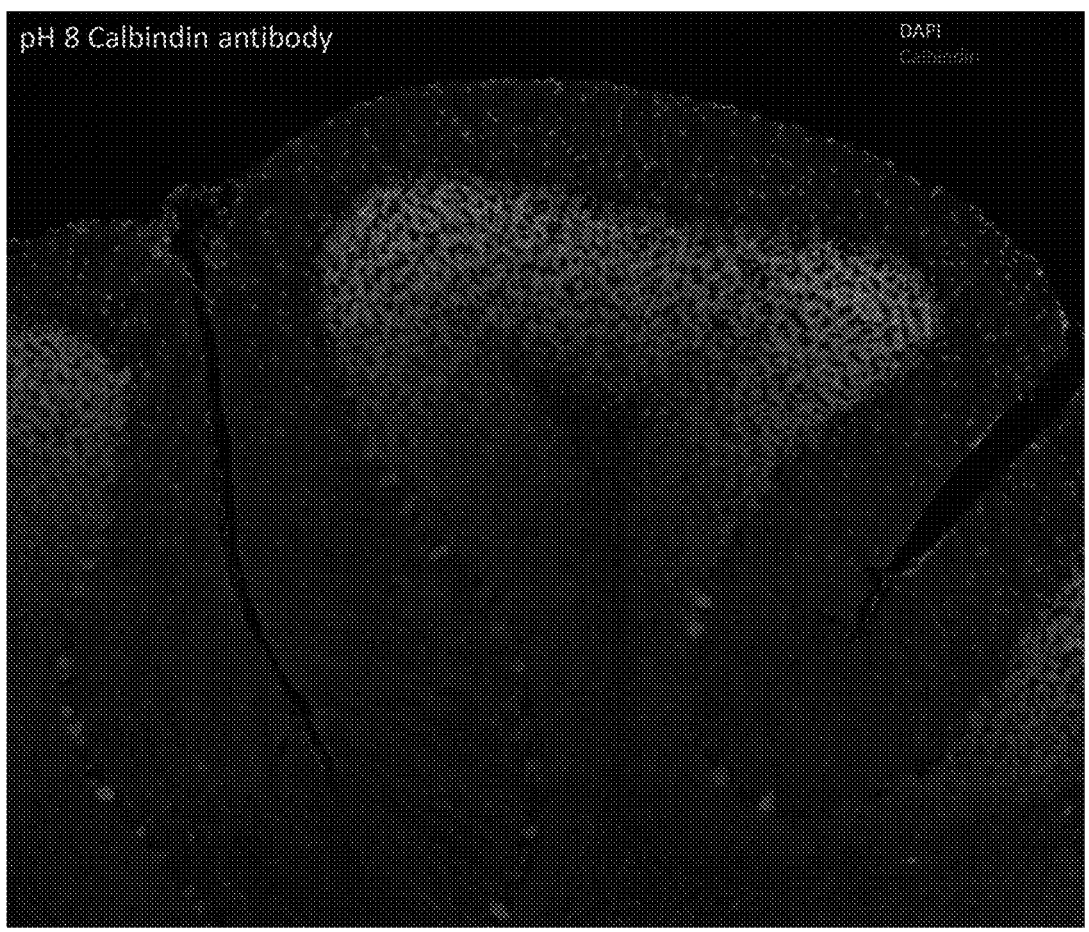
FIG. 8 depicts Calbindin (Synaptic Systems #214006) staining in a mouse cerebellum, as a zoomed image.

FIG. 8 depicts Calbindin (Synaptic Systems #214006) staining in mouse cerebellum. The zoomed image shows Purkinje cells labeled by the calbindin antibody using the pH8 antigen retrieval condition.

GAD67 Antibody: Synaptic Systems #198 006

Figure 9:
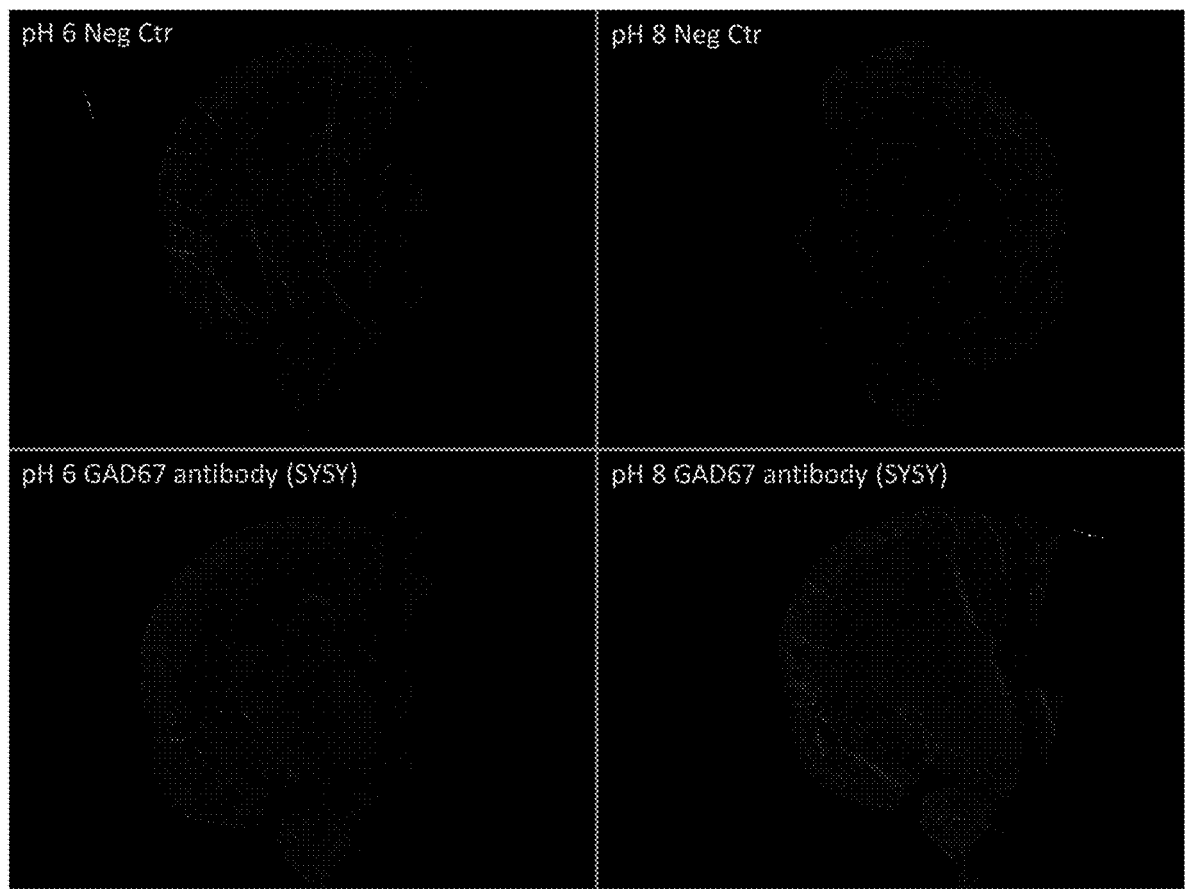
FIG. 9 depicts GAD67 (Synaptic Systems #198 006) staining in a mouse brain at dorsal hippocampus level.

FIG. 9 depicts GAD67 (Synaptic Systems #198 006) staining in mouse brain at dorsal hippocampus level.

Figure 10:
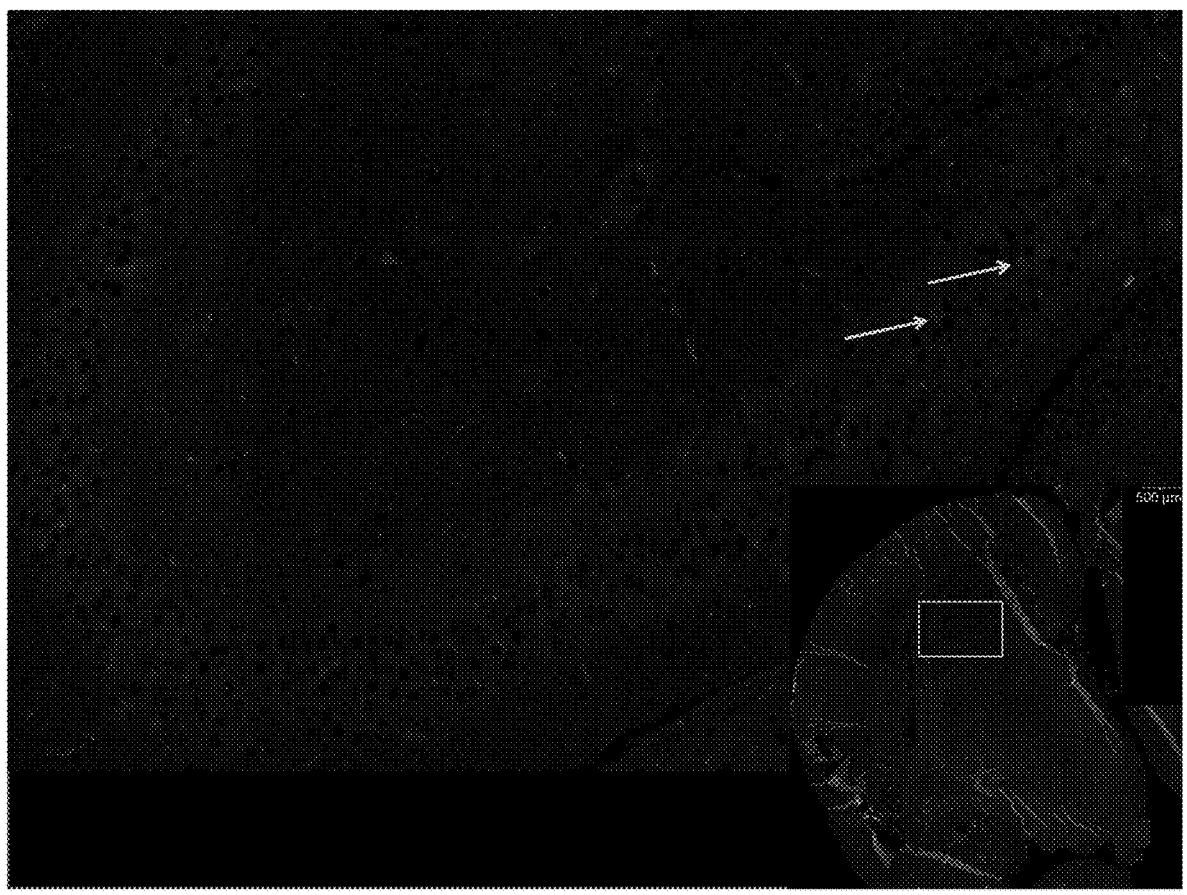
FIG. 10 depicts GAD67 (Synaptic Systems #198 006) staining in mouse brain at dorsal hippocampus level, pH8 antigen retrieval protocol, as a zoomed image over the dorsal hippocampus.

FIG. 10 depicts GAD67 (Synaptic Systems #198 006) staining in mouse brain at dorsal hippocampus level, pH8 antigen retrieval protocol. The zoomed image over the dorsal hippocampus (pH8 antigen retrieval protocol) shows the detection of GABAergic neurons with low fluorescence levels.

GAD67 Antibody: Millipore #MAB5406

Figure 11:
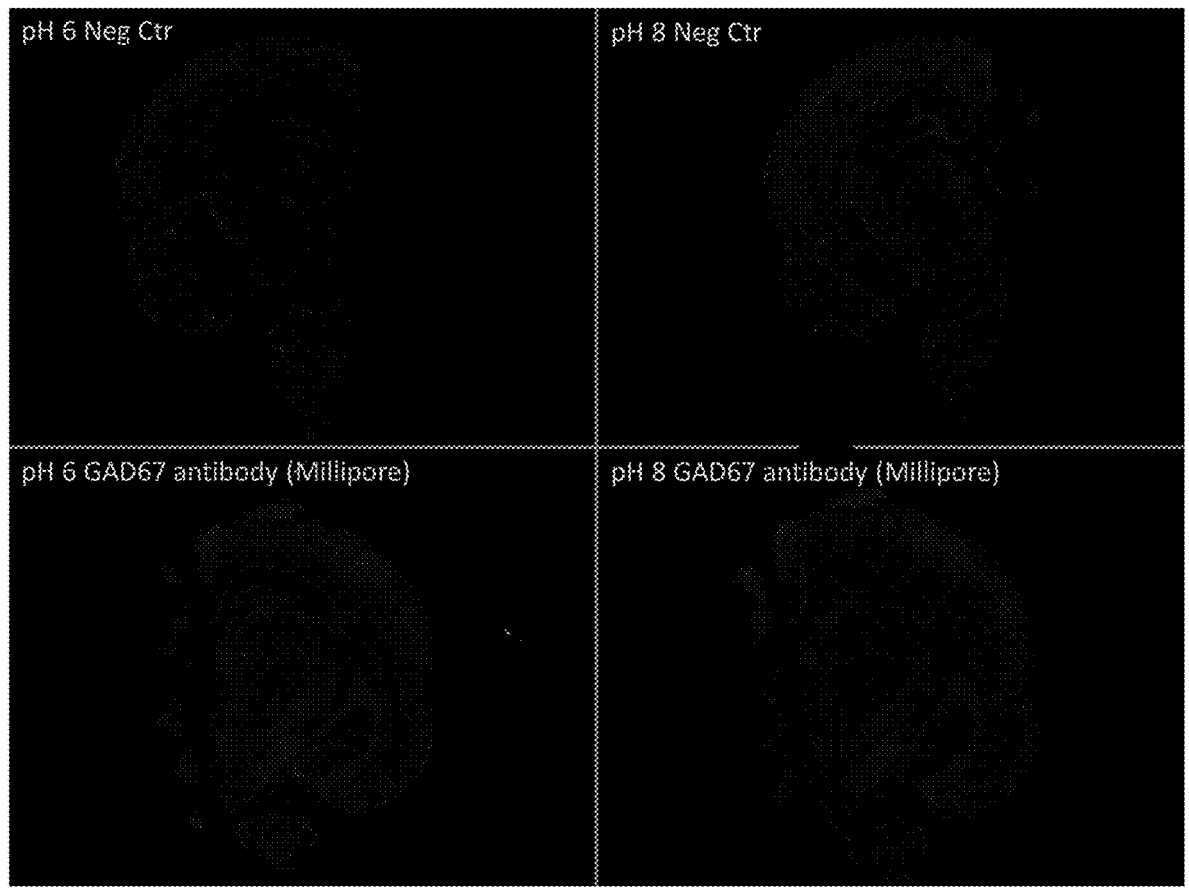
FIG. 11 depicts GAD67 (Millipore #MAB5406) staining in a mouse brain at dorsal hippocampus level.

FIG. 11 depicts GAD67 (Millipore #MAB5406) staining in mouse brain at dorsal hippocampus level.

Figure 12:
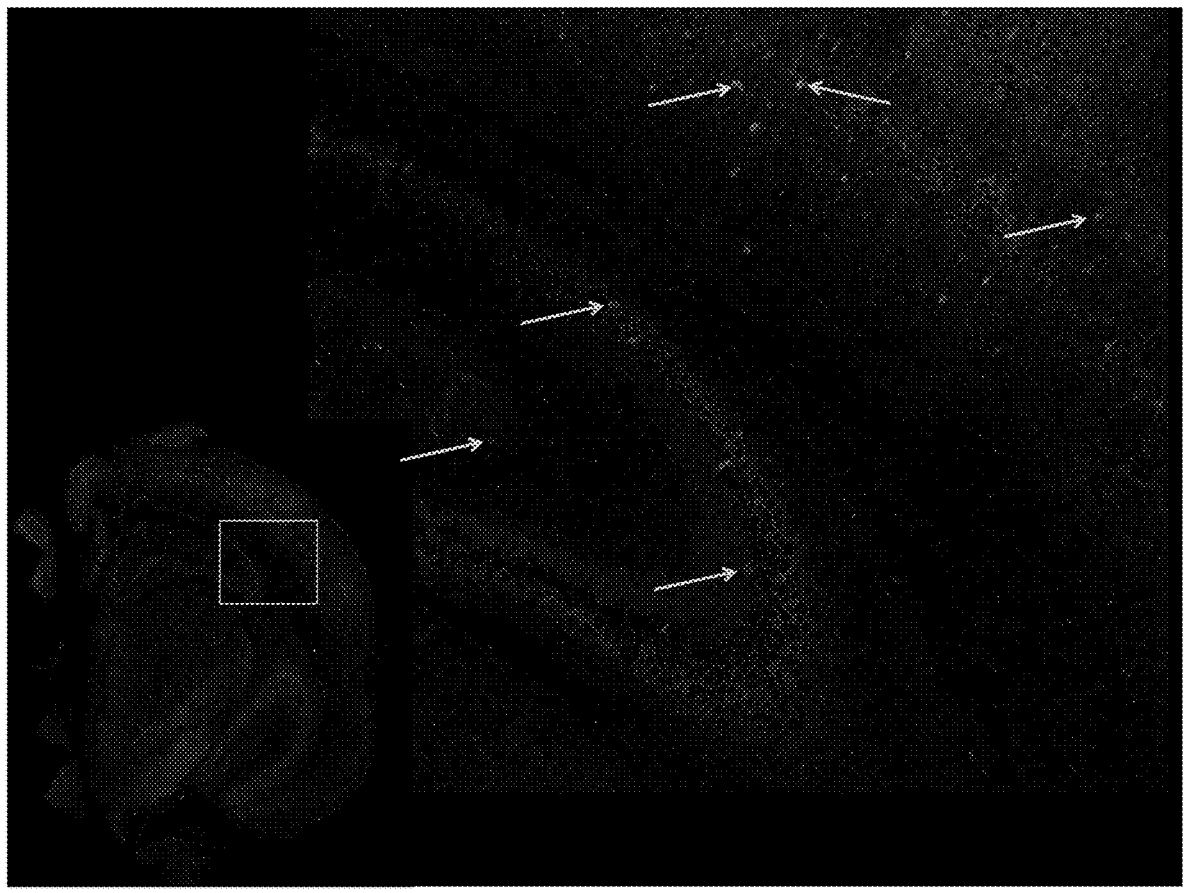
FIG. 12 depicts: GAD67 (Millipore #MAB5406) staining in mouse brain at dorsal hippocampus level, pH8 antigen retrieval protocol.
Zoomed image over the dorsal hippocampus (pH8 antigen retrieval protocol) showing good detection of GABAergic neurons in the hippocampus and in the cortex.

FIG. 12 depicts GAD67 (Millipore #MAB5406) staining in mouse brain at dorsal hippocampus level, pH8 antigen retrieval protocol. The zoomed image over the dorsal hippocampus (pH8 antigen retrieval protocol) shows good detection of GABAergic neurons in the hippocampus and in the cortex.

mCherry Antibody: Molecular Probes #M11217

Figure 13:
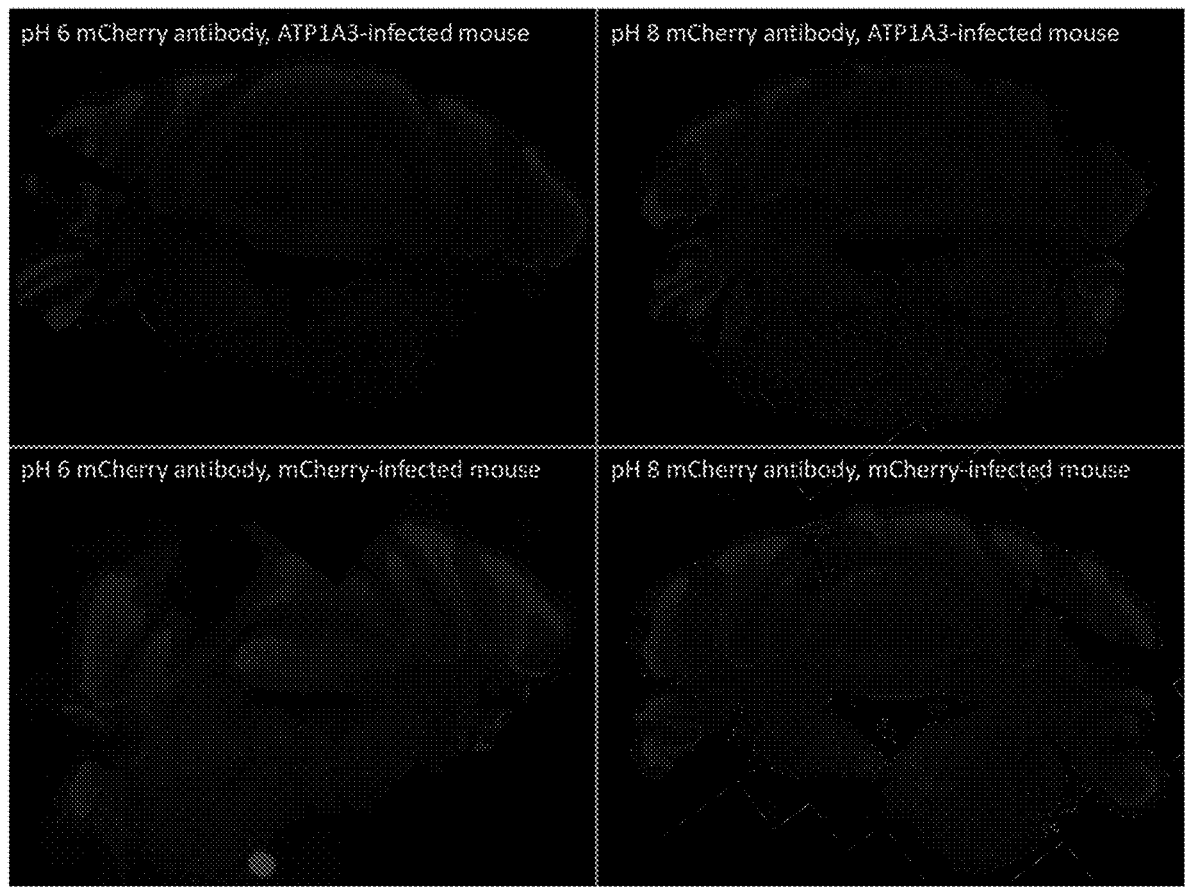
FIG. 13 depicts mCherry staining in a mouse cerebellum.

FIG. 13 depicts mCherry staining in mouse cerebellum. Intense stainings are seen below the fourth ventricle and around this region. In the cerebellum, the staining is more diffuse, but specific staining is observed compared to negative brains (infected with ATP1A3 AAV viruses).

Figure 14:
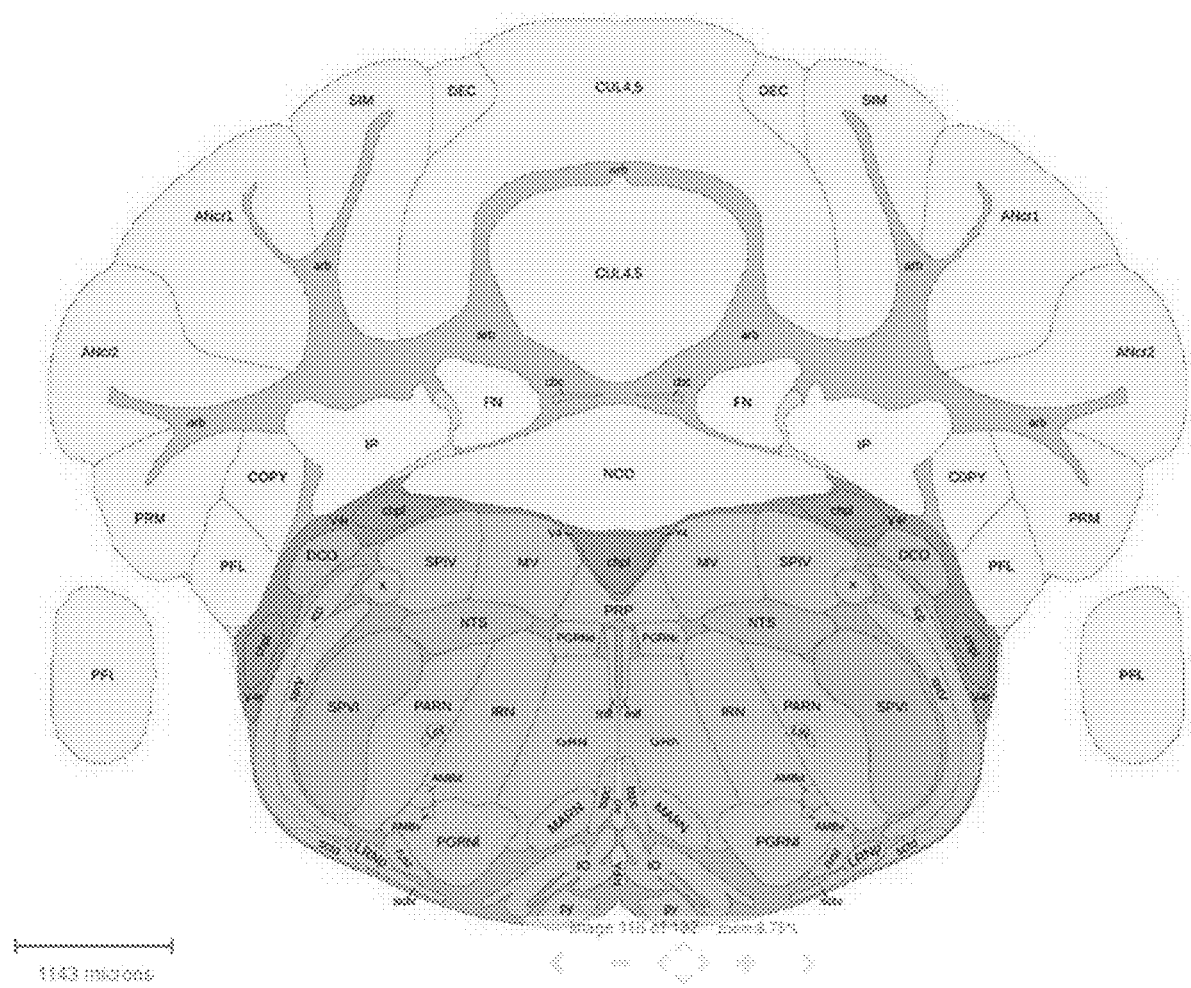
FIG. 14 depicts the mouse cerebellum anatomy.

FIG. 14 depicts the mouse cerebellum anatomy. VERM, indicating the Vermal regions, includes: LING Lingula (I); CENT Central lobule; CUL Culmen; DEC Declive (VI); FOTU Folium-tuber vermis (VII); PYR Pyramus (VIII) ; UVU Uvula (IX); and NOD Nodulus (X). HEM, indicating the Hemispheric regions, includes: SIM Simple lobule; AN Ansiform lobule; PRM Paramedian lobule; COPY Copula pyramidis; PFL Paraflocculus; and FL Flocculus. CBN, indicating Cerebellar nuclei, includes: FN Fastigial nucleus; IP Interposed nucleus; DN Dentate nucleus; and VeCB Vestibulocerebellar nucleus.

Figure 15:
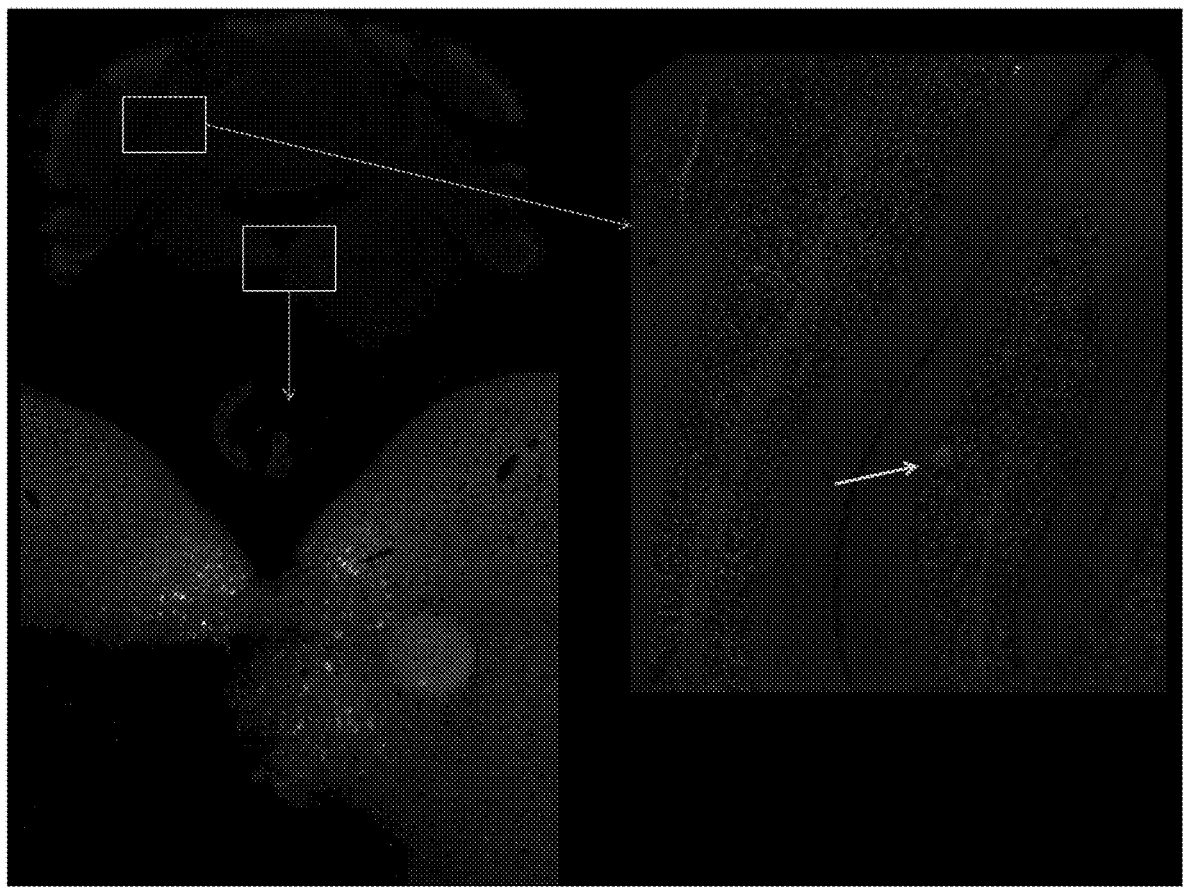
FIG. 15 depicts mCherry staining in mouse cerebellum with pH8 antigen retrieval condition, as zoomed images.

FIG. 15 depicts mCherry staining in mouse cerebellum with pH8 antigen retrieval condition. The zoomed images are of the red channel. Intense stainings are seen below the fourth ventricle and around this region. In the cerebellum, the staining is more diffuse with occasionally a more intense cell that could be a Purkinje cell.

Figure 16:
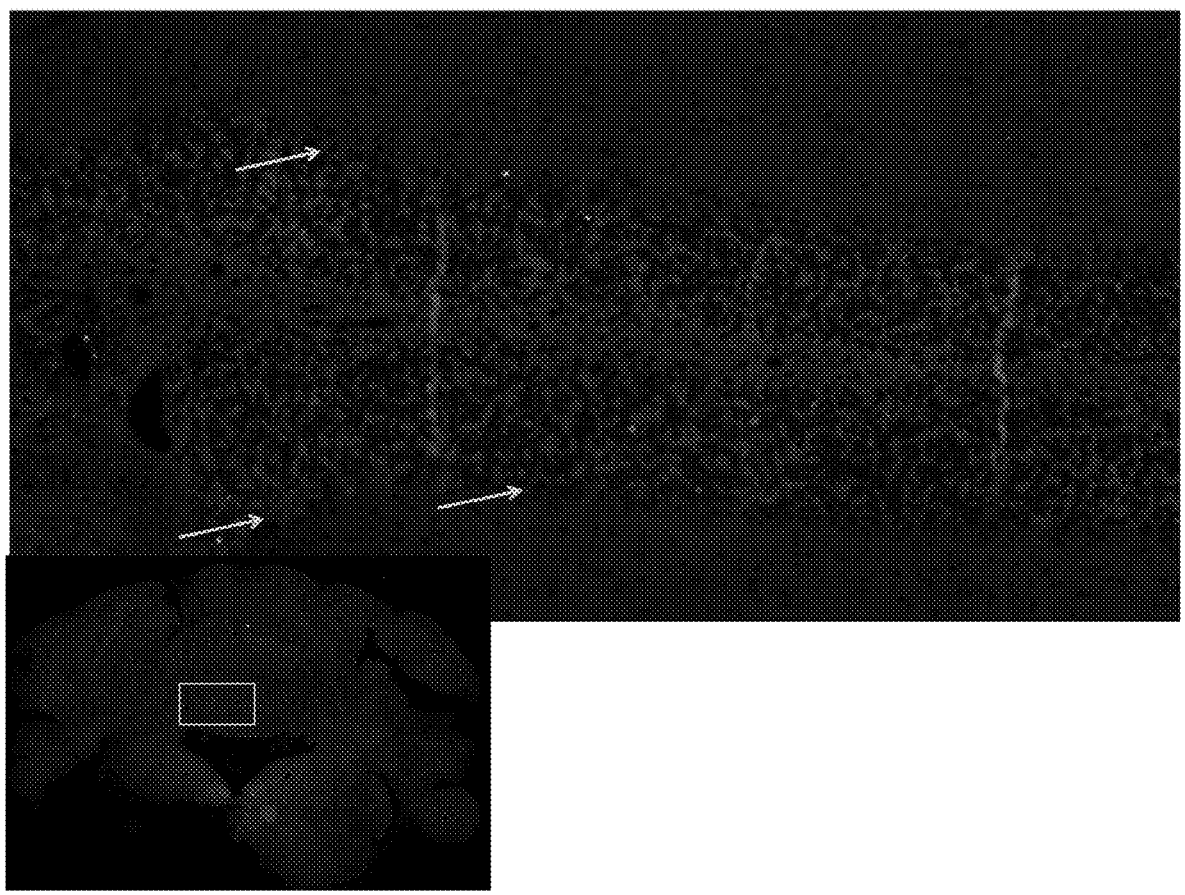
FIG. 16 depicts mCherry staining in mouse cerebellum with pH8 antigen retrieval condition, as zoomed images.

FIG. 16 depicts mCherry staining in mouse cerebellum with pH8 antigen retrieval condition. The zoomed images are of the red channel at levels of Purkinje cell layers. Arrows show examples of Purkinje cells.

4. Conclusions for Staining Development

The Millipore #06-172-1 antibody demonstrated that it was able to detect the target protein, detecting a similar signal as disclosed in the Bottger et al. (2011) publication, in which the specificity of this antibody was shown.

Calbindin was well detecting by the tested antibody, giving signals that can be segmented for Purkinje cell detection. The best condition was to use antigen retrieval at pH8.

The GAD67 antibody from Synaptic Systems (#198 006) allowed detecting some GABAergic neurons but with low fluorescence levels over background.

The GAD67 antibody from Millipore (#MAB5406) allowed detecting GABAergic neurons with good sensitivity and fluorescence levels and can thus be used for further steps of the study plan.

The mCherry antibody allowed detecting positive cells only in the mCherry infected group, with strong signals below the fourth ventricle but also labelings in other regions. Co-labeling with the Calbindin antibody will allow determining if specific signals are measured in Purkinje cells. The signals in Purkinje cells are not as strong as below the fourth ventricle.

5. Cerebellum Staining

ATP1A3 and Calbindin Staining in Cerebellum

Calbindin signals allowed determining the localization of Purkinje neurons. In these, the ATP1A3 signals were peripheral to cells, so once cells were segmented, ATP1A3 was measured in a ring around the calbindin signal.

Figure 17:
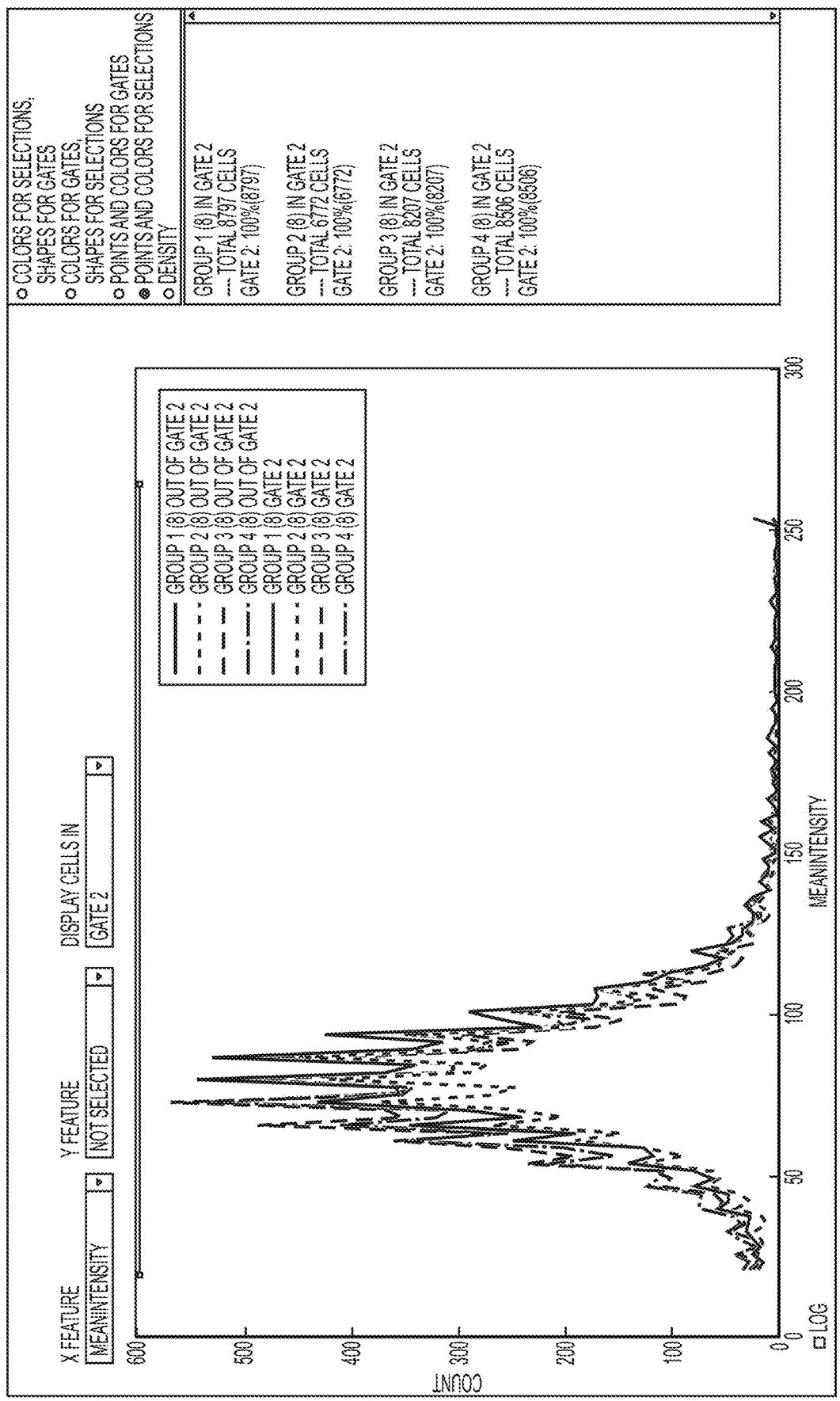
FIG. 17 depicts histograms of the mean intensity of ATP1A3 in the 4 experimental groups. Histograms are well superposed.
Figure 18:
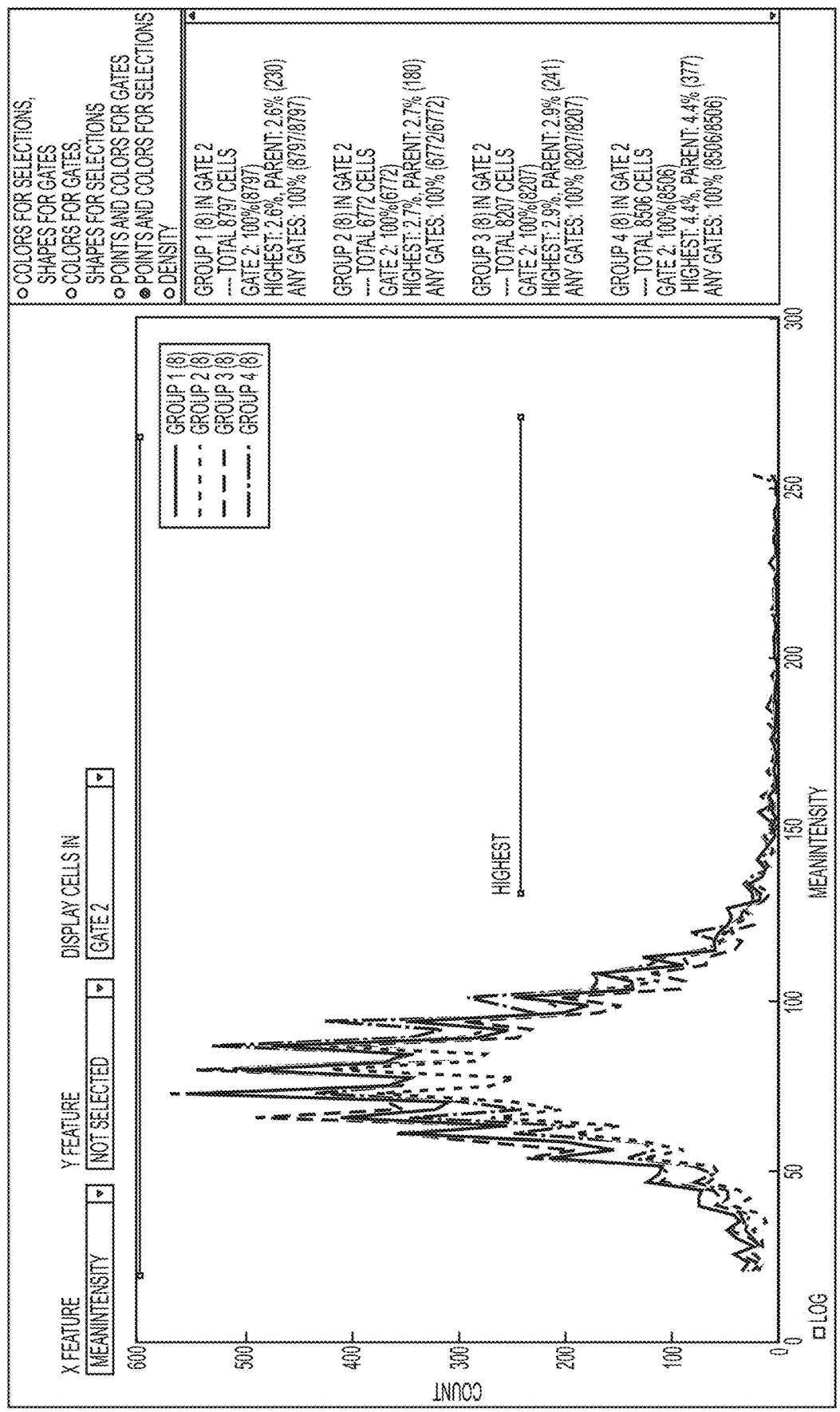
FIG. 18 depicts histograms of the mean intensity of ATP1A3 in the 4 experimental groups with the gate for highest fluorescence levels.
Figure 19:
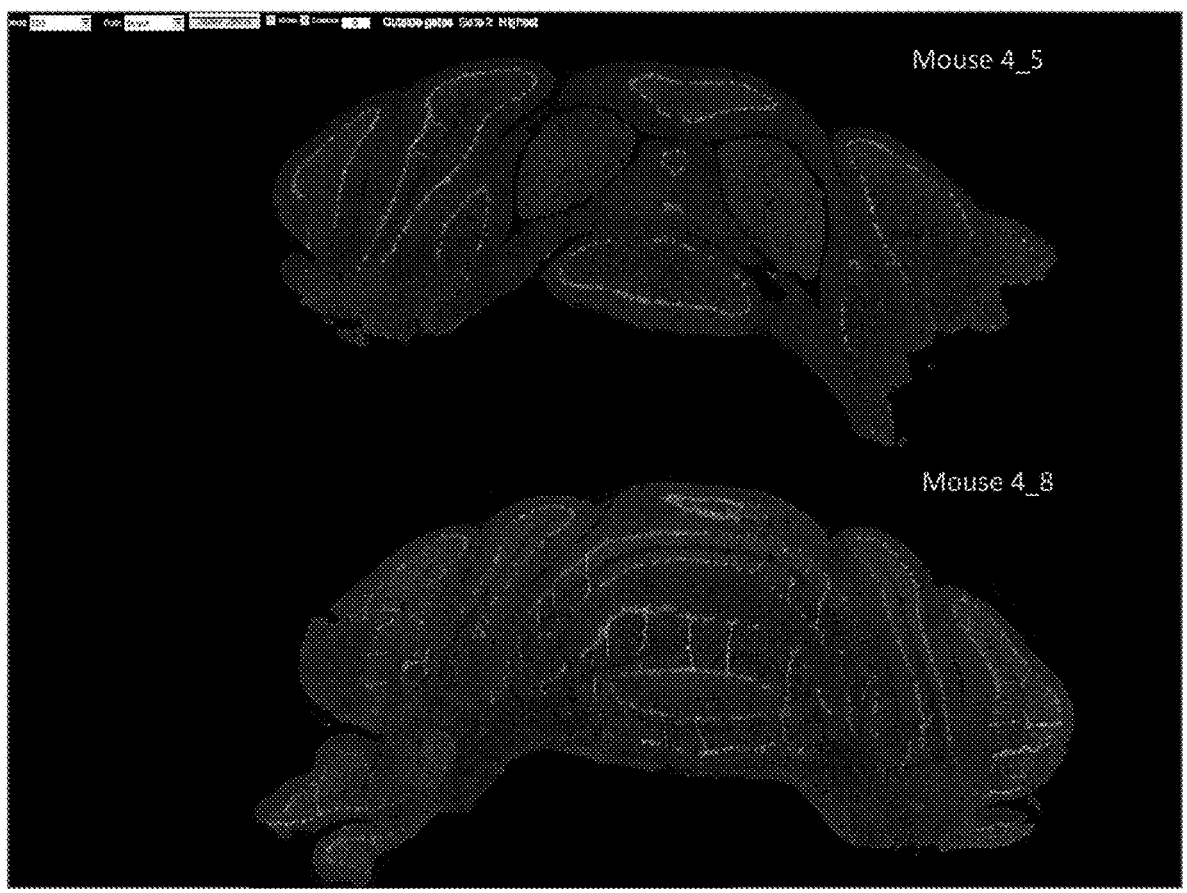
FIG. 19 depicts an example of Purkinje cell detection. Contours of detected cells are shown.
Figure 20:
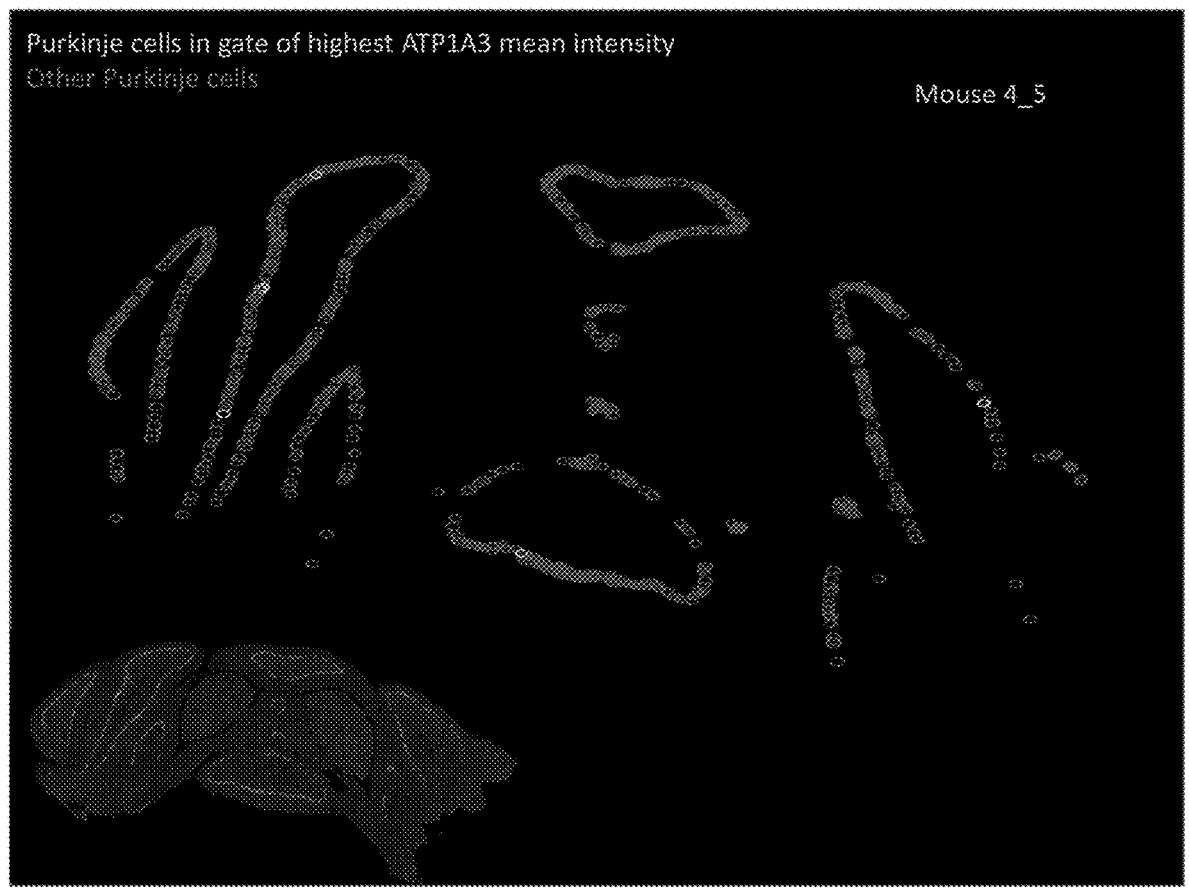
FIG. 20 depicts an example of Purkinje cell detection showing cells with higher ATP1A3 levels. Contours of detected cells are shown in dark shading, and cells in gate are shown in light shading.
Figure 21:
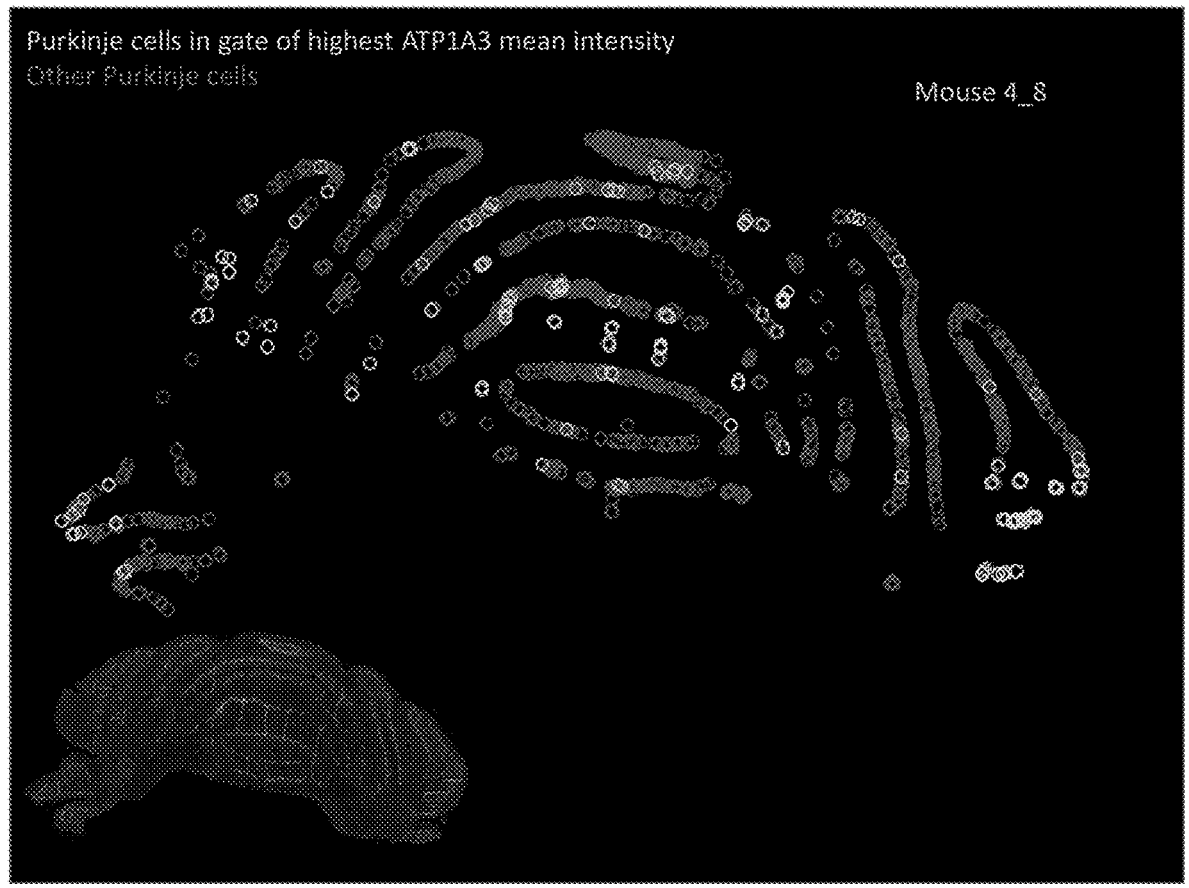
FIG. 21 depicts an example of Purkinje cell detection showing cells with higher ATP1A3 levels. Contours of detected cells are shown in dark shading, and cells in gate are shown in light shading.

Cell-by-cell data was fed into the proprietary Cytosurfer software to make cytometric analyses. The mean ATP1A3 fluorescence was plotted against cell count (FIG. 17) and the cells from the same groups displayed group by group. The intensity histograms were well superposed. A gate was chosen to detect Purkinje cells with higher ATP1A3 intensity (FIG. 18) which should appear if ATP13 intensity is increased. FIGS. 19, 20, and 21 show the detected Purkinje neurons and the localization of cells with higher mean intensity. These cells are anatomically regularly spread and do not present a gradient from the cisterna magna. Moreover, in FIG. 21, most of the cells detected with increased ATP1A3 are false positive due to creases in the cerebellum slice which induces a higher green fluorescence signal.

Figure 22:
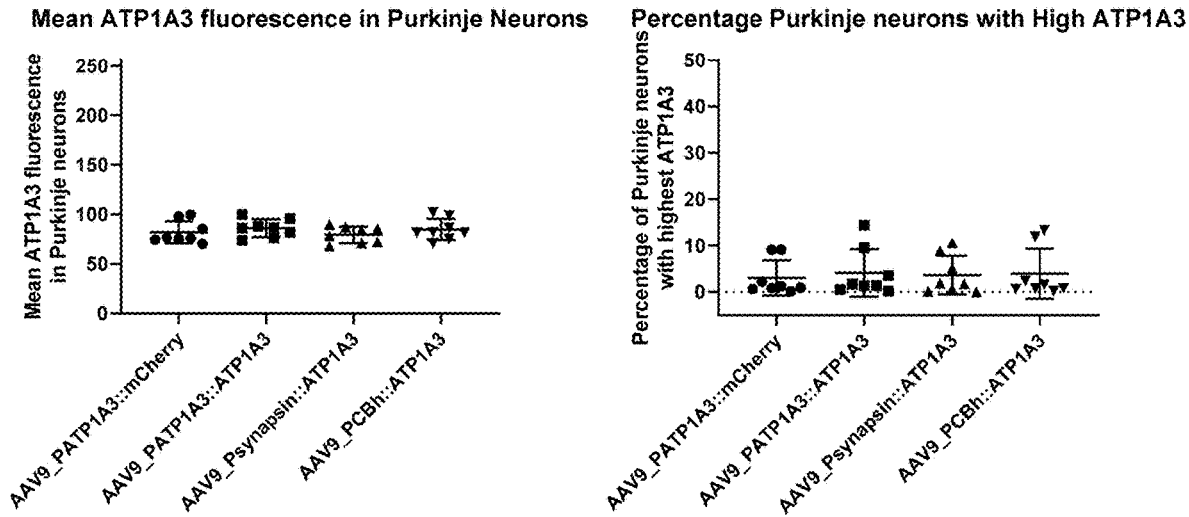
FIG. 22 depicts graphical representations of mean ATP1A3 intensity in Purkinje Neurons and percentage of Purkinje neurons with high ATP1A3 intensity. The left graft shows mean intensity in Purkinje Neurons, and the right graph shows the percentage of Purkinje neurons with High ATP1A3 intensity.
Figure 23:
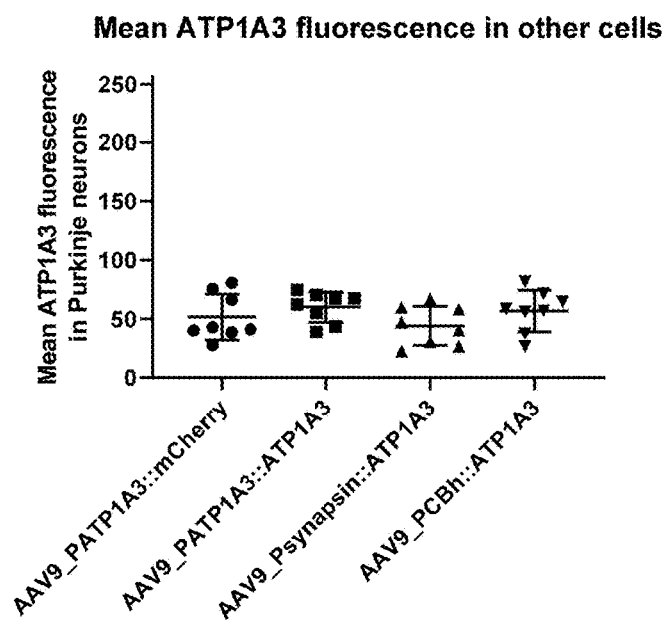
FIG. 23 depicts graphical representations of mean ATP1A3 intensity in cerebellar cells other than Purkinje neurons.
Figure 24:
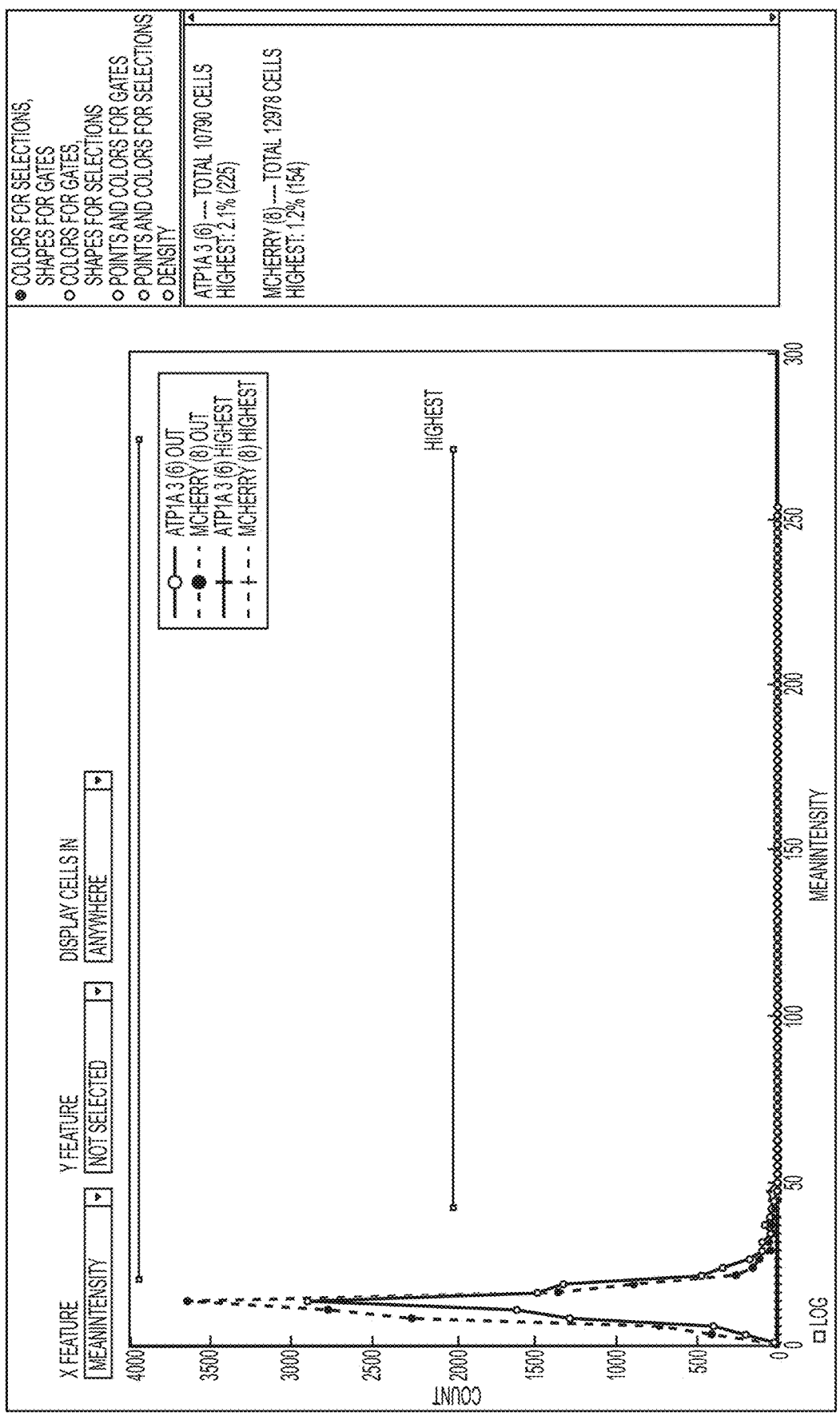
FIG. 24 depicts a histogram of the mean intensity of mCherry in the mCherry group and animals from ATP1A3 infected groups, with gate for highest fluorescence levels.
Figure 25:
FIG. 25 depicts an example of Purkinje cell detection showing cells with higher mCherry levels (cells in Gate named Highest). Contours of detected cells are shown in black, and cells in gate are shown in dark shading.
Figure 26:
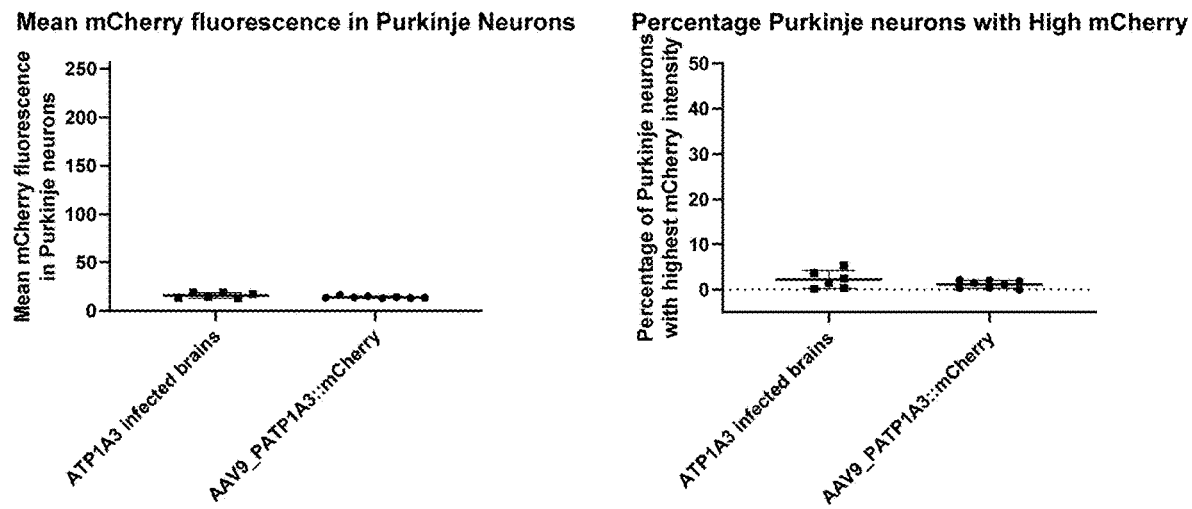
FIG. 26 depicts graphical representations of mean mCherry intensity in Purkinje Neurons and the percentage of Purkinje neurons with high mCherry intensity. The left graft shows the mean intensity in Purkinje Neurons. The right graph shows the percentage of Purkinje neurons with High mCherry intensity.
Figure 27:
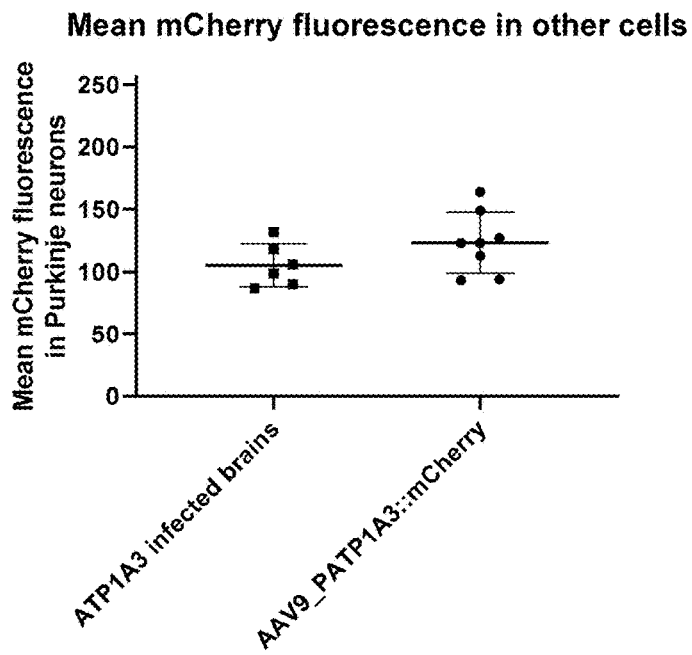
FIG. 27 depicts graphical representations of mean mCherry intensity in cerebellar cells other than Purkinje neuron.

Quantification of ATP1A3 in the different experimental groups shows that the use of ATP1A3 expressing AAV viruses did not increase ATP1A3 mean fluorescence in Purkinje neurons, nor the percentage of cells with increased ATP1A3 expression (FIG. 22). Similarly, no differences appeared in other cells that were analyzed (FIG. 23).

mCherry and Calbindin Staining in Cerebellum mCherry expression was used as a positive control of AAV injection and transgene expression. Cytometric analysis of mCherry intensity in Purkinje neurons showed a similar profile in mCherry infected mice compared to ATP1A3 infected mice (FIG. 24). A few cells with higher mCherry fluorescence were detected, but this was artificial as these higher signals appeared where creases in the tissue were present (FIG. 25). Quantifications support the absence of differences between treatment groups in Purkinje Neurons (FIG. 26) and other cells (FIG. 27).

6. Brainsstem Staining mCherry Staining in Brainstem

Figure 28:
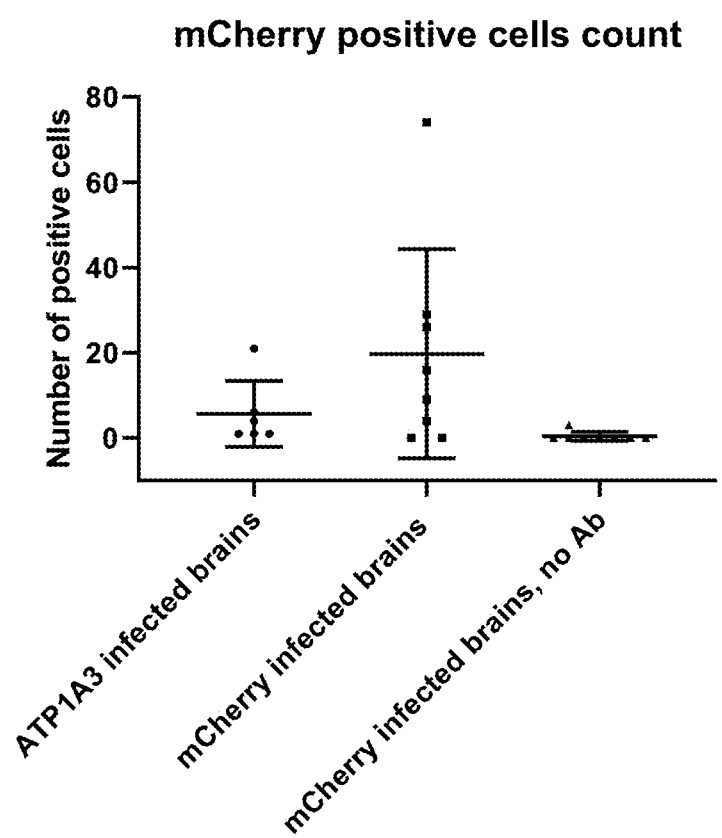
FIG. 28 depicts counts of mCherry positive cells in mCherry infected brainstems.

Depending on the slices, the brainstem was more or less preserved. mCherry staining was well detected in some brainstems of mCherry-AAV infected brains while no specific signals were present in ATP1A3-AAV infected brains. The pattern of mCherry expression was not widespread but instead focalized in discrete regions, which suggests that the injection site was not truly in the Cisterna Magna but rather in the brainstem itself. Moreover, in some brainstems, no mCherry expression could be detected (FIG. 28).

ATP1A3 Staining in Brainstem

Figure 29:
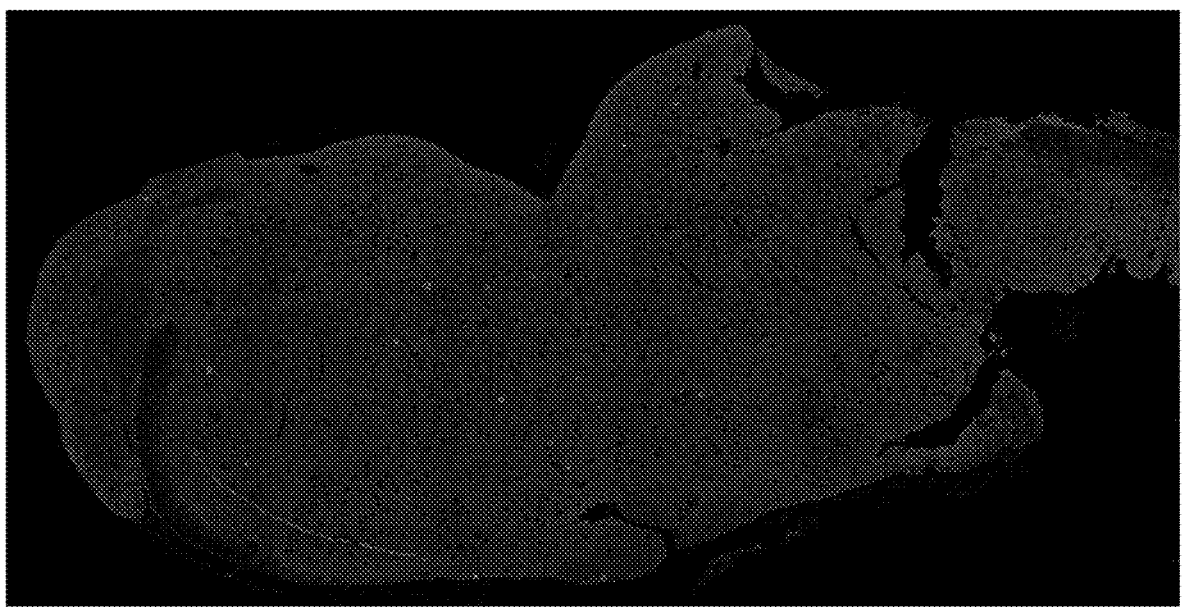
FIG. 29 depicts an example of cells with higher ATP1A3.
Figure 30:
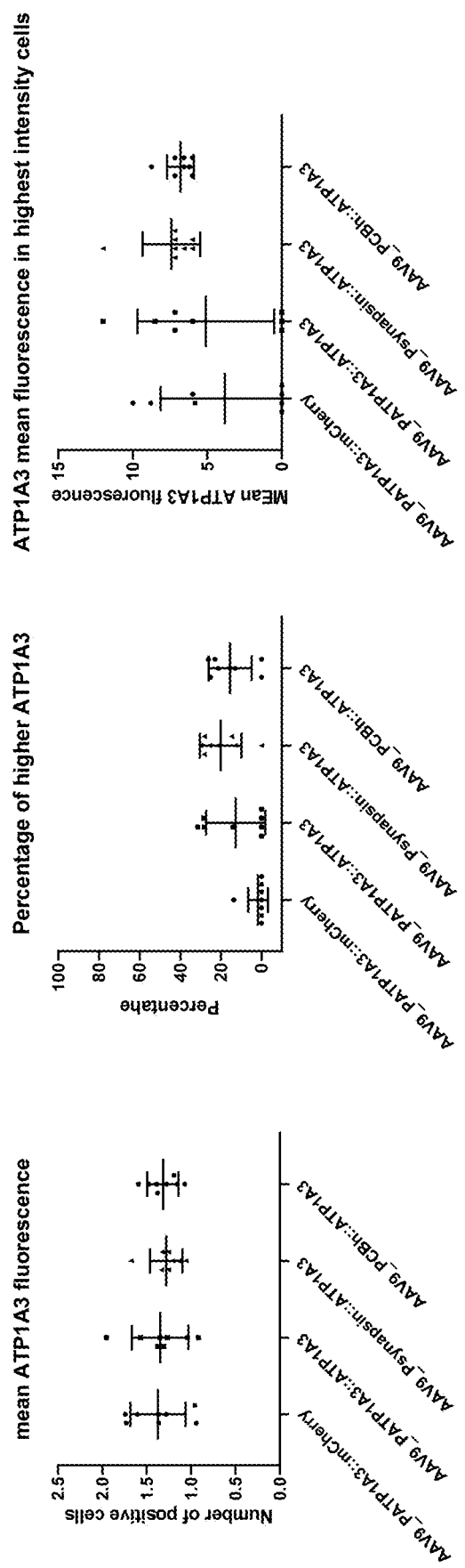
FIG. 30 depicts quantification of ATP1A3 immunofluorescence. The left graft shows ATP1A3 immunofluorescence at the surrounding of all detected cells. The middle graft shows the percentage of cells detected as higher expressing ATP1A3 after gating. The right graft shows mean fluorescence in cells in highest ATP1A3 gate.

Contrary to mCherry, there were no obvious localization of higher ATP1A3 signals in the brainstem. A few cells showed higher intensity but were spread in the brainstem. The staining intensity in general and staining intensity in highest intensity cells were not different for the different experimental groups and compared to the mCherry-infected group (FIG. 29). The interimage variability was higher than the intra image variability and quantifications do not show clear cut differences between ATP1A3 expressing AAV viruses (FIG. 30).

7. Data

Cerebellum Analysis:

| AAV9_PATP1A3::mCherry | AAV9_PATP1A3::ATP1A3 | AAV9_Psynapsin::ATP1A3 | AAV9_PCBh::ATP1A3 |
|---|---|---|---|
| Percentage Purkinje neurons with High ATP1A3 | | | |
| 9.08 | 0.534 | 8.91 | 13.3 |
| 0.957 | 0.212 | 0 | 2.4 |
| 1.19 | 9.57 | 10.6 | 0.742 |
| 0.668 | 1.39 | 5.05 | 1.52 |
| 0.838 | 3.56 | 1.77 | 0.775 |
| 0.175 | 1.72 | 0.114 | 0.644 |
| 2.21 | 14.4 | 1.86 | 0.204 |
| 9.08 | 1.36 | 0.629 | 11.9 |
| Mean ATP1A3 fluorescence in Purkinje Neurons | | | |
| 99.8 | 76.2 | 89.9 | 98.7 |
| 74.4 | 73.9 | 67.8 | 86.4 |
| 76.7 | 96 | 85.4 | 81.5 |
| 75.9 | 82 | 78.3 | 82.1 |
| 70.3 | 88 | 87.1 | 75.3 |
| 75.2 | 86.1 | 71.2 | 81.5 |
| 85.2 | 100 | 84.4 | 71 |
| 97.9 | 86.8 | 72.3 | 102 |
| Mean ATP1A3 fluorescence in other cells | | | |
| 80.7 | 43.7 | 58.2 | 71.6 |
| 38.6 | 38.9 | 22.5 | 64.7 |
| 42.9 | 74.6 | 47.1 | 55.9 |
| 40.3 | 55.2 | 40.4 | 56.9 |
| 27.8 | 67.4 | 66.8 | 37.3 |
| 41.1 | 62.2 | 26.6 | 58.6 |

-continued

| | | | |
|---|---|---|---|
| 66.3 | 70.2 | 59.6 | 26.7 |
| 75.5 | 67.5 | 30.6 | 81.7 |

| AAV9_PATP1A3::mCherry | ATP1A3 infected brains |
|---|---|
| Percentage Purkinje neurons with High mCherry | |
| 2.14 | 0.358 |
| 2.08 | 5.27 |
| 1.93 | 2.43 |
| 0.303 | 3.66 |
| 0 | 1.44 |
| 1.44 | 0.149 |
| 1.11 | |
| 0.366 | |
| Mean mCherry fluorescence in Purkinje Neurons | |
| 16.3 | 13.5 |
| 13.4 | 19 |
| 15.1 | 18.6 |
| 13.8 | 17.1 |
| 14 | 14.5 |
| 13.4 | 12.7 |
| 13 | |
| 13.2 | |
| Mean mCherry fluorescence in other cells | |
| 127 | 98.6 |
| 123 | 132 |
| 93.9 | 106 |
| 164 | 118 |
| 113 | 90.2 |
| 93.3 | 86.9 |
| 149 | |
| 123 | |

Brainstem Analysis:

| ATP1A3 infected brains | mCherry infected brains | mCherry infected brains, no Ab |
|---|---|---|
| Number of mCherry positive cells in brainstem | | |
| 1 | 9 | 0 |
| 1 | 74 | 0 |
| 21 | 26 | 0 |
| 1 | 16 | 0 |
| 6 | 4 | 0 |
| 4 | 29 | 3 |
| | 0 | 0 |
| | 0 | 0 |

| AAV9_PATP1A3::mCherry | AAV9_PATP1A3::ATP1A3 | AAV9_Psynapsin::ATP1A3 | AAV9_PCBh::ATP1A3 |
|---|---|---|---|
| Mean ATP1A3 fluorescence in all cells | | | |
| 0.9594657 | 1.5719883 | 1.6757175 | 1.2800999 |
| 1.2781088 | 1.3089229 | 1.0601813 | 1.5957804 |
| 1.3683764 | 1.9546749 | 1.2545795 | 1.3809592 |
| 1.7401803 | 1.2677235 | 1.3345006 | 1.0735391 |
| 0.9455498 | 1.3787239 | 1.2546315 | 1.1570685 |
| 1.7301957 | 1.3529171 | 1.3236297 | 1.4783155 |
| 1.3649146 | 1.0431079 | 1.2071395 | 1.192403 |
| 1.6091142 | 0.919077 | 1.1412062 | 1.3906967 |
| Percentage of cells with higher ATP1A3 expression | | | |
| 0 | 0.0141583 | 0.0179856 | 22.941409 |
| 13.759039 | 14.096621 | 25.746196 | 0.0182615 |
| 0.0386548 | 0 | 21.581866 | 13.021047 |
| 0.066357 | 28.1575 | 13.068149 | 26.281911 |

-continued

| | | | |
|---|---|---|---|
| 0.0786164 | 31.462178 | 29.967949 | 25.172961 |
| 0 | 0 | 14.827064 | 0.067128 |
| 0 | 28.490776 | 28.233045 | 21.261966 |
| 0 | 0 | 28.181818 | 15.526353 |
| ATP1A3 mean fluorescence in subpopulation with higher ATP1A3 | | | |
| 0 | 12 | 12 | 6.579797 |
| 5.997402 | 5.9995585 | 7.1953383 | 8.75 |
| 5.848485 | 0 | 6.5679874 | 6.0148131 |
| 8.8166668 | 7.1851386 | 6.0072859 | 7.1872419 |
| 10 | 7.1648367 | 7.183503 | 7.1800464 |
| 0 | 0 | 6.0020599 | 6.1937063 |
| 0 | 8.5209115 | 7.1846988 | 6.5676226 |
| 0 | 0 | 7.177844 | 6.0161244 |

We claim:

1. A composition comprising a recombinant adeno-associated virus (AAV) vector comprising a nucleic acid sequence encoding an ATP1A3 (sodium/potassium- transporting ATPase subunit alpha-3) protein, and a promoter sequence that renders the expression of the ATP1A3-coding nucleic acid sequence specific to the central nervous system, wherein the recombinant MV vector comprises one of SEQ ID Nos: 3-5 and wherein the AAV vector is AAV2, AAV9, or AAVrh10.

2. The composition of claim 1, wherein the AAV vector is AAV9.

3. The composition of claim 2, further comprising one or more nucleic acid regulatory sequences, linked directly or indirectly to the ATP1A3-coding nucleic acid sequence.

4. The composition of claim 1, wherein the promoter sequence is neuron-specific or glia-specific.

5. The composition of claim 3, wherein the nucleic acid regulatory sequence comprises a sequence to regulate ribosome binding and/or translation efficiency of the ATP1A3 gene.

6. The composition of claim 5, wherein the sequence to regulate ribosome binding and/or translation efficiency is a Kozak sequence.

7. The composition of claim 3, wherein the nucleic acid regulatory sequence comprises a 3'-UTR sequence that contains a polyadenylation sequence.

8. The composition of claim 7, wherein the 3'-UTR sequence is a rabbit beta globin polyadenylation sequence (rBGpA).

9. The composition of claim 3, wherein the recombinant AAV vector comprises AAV9/$P_{CBh}$-ATP1A3 cDNA-rBGpA, AAV9/$P_{hSyn}$-ATP1A3 cDNA-rBGpA, or AAV9/$P_{ATP1A3}$-ATP1A3 cDNA-rBGpA.

10. The composition of claim 2, wherein the AAV9 vector has a single-stranded DNA genome.

11. The composition of claim 1, wherein the recombinant AAV vector comprises SEQ ID No: 3.

12. The composition of claim 1, wherein the recombinant AAV vector comprises SEQ ID No: 4.

13. The composition of claim 1, wherein the recombinant AAV vector comprises SEQ ID No: 5.

\* \* \* \* \*

UNITED STATES PATENT AND TRADEMARK OFFICE
CERTIFICATE OF CORRECTION

| | |
|---|---|
| PATENT NO. | : 11,738,093 B2 |
| APPLICATION NO. | : 16/379440 |
| DATED | : August 29, 2023 |
| INVENTOR(S) | : Simon Frost et al. |

It is certified that error appears in the above-identified patent and that said Letters Patent is hereby corrected as shown below:

In the Claims

In Claim 1, Column 49, Line 35, please delete "wherein the recombinant MV vector" and replace it with "wherein the recombinant AAV vector"

Signed and Sealed this
Twenty-fourth Day of October, 2023

Katherine Kelly Vidal
*Director of the United States Patent and Trademark Office*